(12) United States Patent
Kolesnikov et al.

(10) Patent No.: US 9,162,986 B2
(45) Date of Patent: *Oct. 20, 2015

(54) 2-(2-HYDROXYBIPHENYL-3-YL)-1H-BENZOIMIDAZOLE-5-CARBOXAMIDINE DERIVATIVES AS FACTOR VIIA INHIBITORS

(71) Applicant: PHARMACYCLICS LLC, Sunnyvale, CA (US)

(72) Inventors: Aleksandr Kolesnikov, San Francisco, CA (US); Roopa Rai, San Carlos, CA (US); William Dvorak Shrader, Belmont, CA (US); Steven M. Torkelson, San Mateo, CA (US); Kieron E. Wesson, Burlingame, CA (US); Wendy B. Young, San Mateo, CA (US)

(73) Assignee: PHARMACYCLICS LLC, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/317,755

(22) Filed: Jun. 27, 2014

(65) Prior Publication Data

US 2014/0378453 A1  Dec. 25, 2014

Related U.S. Application Data

(60) Continuation of application No. 13/607,402, filed on Sep. 7, 2012, now Pat. No. 8,778,625, which is a continuation of application No. 13/100,107, filed on May 3, 2011, now Pat. No. 8,299,110, which is a continuation of application No. 12/255,540, filed on Oct. 21, 2008, now abandoned, which is a division of application No. 10/537,115, filed as application No. PCT/US03/38635 on Dec. 3, 2003, now Pat. No. 7,479,502.

(60) Provisional application No. 60/430,981, filed on Dec. 3, 2002.

(51) Int. Cl.
| | | |
|---|---|---|
| *C07D 235/18* | (2006.01) | |
| *C07D 401/12* | (2006.01) | |
| *C07D 403/10* | (2006.01) | |
| *C07D 235/12* | (2006.01) | |
| *C07D 235/16* | (2006.01) | |
| *C07F 9/09* | (2006.01) | |
| *C07F 9/12* | (2006.01) | |
| *C07F 9/6512* | (2006.01) | |
| *C12Q 1/56* | (2006.01) | |

(52) U.S. Cl.
CPC ............ *C07D 235/18* (2013.01); *C07D 235/12* (2013.01); *C07D 235/16* (2013.01); *C07D 401/12* (2013.01); *C07D 403/10* (2013.01); *C07F 9/094* (2013.01); *C07F 9/12* (2013.01); *C07F 9/65128* (2013.01); *C12Q 1/56* (2013.01)

(58) Field of Classification Search
CPC ..... C07D 235/18; C07D 403/10; C07D 401/12
See application file for complete search history.

(56) References Cited

U.S. PATENT DOCUMENTS

| | | | |
|---|---|---|---|
| 6,867,200 B1 | 3/2005 | Allen et al. | |
| 7,479,502 B2 | 1/2009 | Kolesnikov et al. | |
| 8,299,110 B2 * | 10/2012 | Kolesnikov et al. | 514/394 |
| 8,415,328 B2 | 4/2013 | Dickman et al. | |
| 8,552,046 B2 | 10/2013 | Loury et al. | |
| 8,729,117 B2 | 5/2014 | Dickman et al. | |
| 8,748,468 B2 | 6/2014 | Loury et al. | |
| 8,778,625 B2 * | 7/2014 | Kolesnikov et al. | 435/13 |
| 2003/0114457 A1 | 6/2003 | Hu et al. | |
| 2005/0176797 A1 | 8/2005 | Hu et al. | |
| 2005/0203094 A1 | 9/2005 | Kolesnikov | |
| 2007/0049523 A1 | 3/2007 | Hansen et al. | |
| 2008/0275250 A1 | 11/2008 | Dickman et al. | |
| 2009/0054432 A1 | 2/2009 | Kolesnikov et al. | |
| 2013/0157298 A1 | 6/2013 | Kolesnikov et al. | |
| 2014/0039022 A1 | 2/2014 | Loury et al. | |
| 2014/0221667 A1 | 8/2014 | Dickman et al. | |

FOREIGN PATENT DOCUMENTS

| | | |
|---|---|---|
| EP | A-0834508 | 4/1998 |
| JP | A-2002-532479 | 7/2004 |
| RU | 2297216 | 4/2007 |
| WO | WO-00-35886 | 6/2000 |
| WO | WO-01-39773 | 6/2001 |
| WO | WO-02-14274 A1 | 2/2002 |
| WO | WO-02-14307 A1 | 2/2002 |
| WO | WO-0214307 A1 | 2/2002 |
| WO | WO-03-006011 A1 | 1/2003 |
| WO | WO-03-006670 A2 | 1/2003 |
| WO | WO-03-006670 A3 | 1/2003 |
| WO | WO-03-068756 A1 | 8/2003 |
| WO | WO-2004-050637 | 6/2004 |
| WO | WO-2004-062661 | 7/2004 |
| WO | WO-2005-118554 | 12/2005 |
| WO | WO-2005-121102 A2 | 12/2005 |
| WO | WO-2005-121102 A3 | 12/2005 |
| WO | WO-2009-052323 A2 | 4/2009 |
| WO | WO-2009-052323 A3 | 4/2009 |

OTHER PUBLICATIONS

Cancer, http://www.hlm.nih.gove/medlineplus/cancer.html, 2009, [retrieved from the Internet on Mar. 17, 2009].

(Continued)

*Primary Examiner* — Yong Chu
(74) *Attorney, Agent, or Firm* — Wilson Sonsini Goodrich & Rosati

(57) ABSTRACT

The present invention relates to novel inhibitors of Factors VIIa, IXa, Xa, XIa, in particular Factor VIIa, pharmaceutical compositions comprising these inhibitors, and methods for using these inhibitors for treating or preventing thromboembolic disorders, cancer or rheumatoid arthritis. Processes for preparing these inhibitors are also disclosed.

3 Claims, No Drawings

(56) References Cited

OTHER PUBLICATIONS

Golub et al. Molecular Classification of Cancer: Class Discovery and Class Prediction by Gene Expression Monitoring. Science 286:521-537 (1999).
Katz et al. A novel serine protease inhibition motif involving a multi-centered short hydrogen bonding network at the active site. J. Mol. Biol. 307(5):1451-1486 (2001).
Katz et al. Engineering inhibitors highly selective for the S1 sites of Ser190 trypsin-like serine protease drug targets. Chem. Biol. 8(11):1107-1121 (2001).
Kolesnikov et al. STN International HCAPLUS database. (Columbus, OH). Accession No. 2004:493686.
Kolesnikov et al. STN International HCAPLUS database. (Columbus, OH). Accession No. 2004:610079.
Lala et al. Role of nitric oxide in tumor progression: Lessons from experimental tumors. Cancer Metastasis Reviews 17(1):91-106 (1998).
Loury et al. STN International HCAPLUS database. (Columbus, OH). Accession No. 2009:486977.
PCT/US2003/038635 Search Report mailed Sep. 2, 2004.
PCT/US2005/019394 International Search Report dated Jan. 16, 2006.
PCT/US2005/019394 IPRP dated Dec. 4, 2006.
PCT/US2008/80221 International Search Report and Written Opinion dated Jul. 29, 2009.
PCT/US2008/80221 IPRP dated Apr. 20, 2010.
Sausville et al. Contributions of Human Tumor Xenografts to Anticancer Drug Development. Cancer Res 66(7):3351-3354 (2006).
Sendzik and Hui. Environmentally friendly and efficient: iron-mediated reduction of 3-methyl-5-aryl-1,2,4-oxadiazoles to benzamidines. Tetrahedron Letters 44:8697-8700 (2003).
Stella. Chemical and physical bases determining the instability and incompatibility of formulated injectable drugs. J. Parenteral Sci. Tech. 40(4):142-163 (1996).
U.S. Appl. No. 10/537,115 Office Action dated Aug. 29, 2007.
U.S. Appl. No. 11/597,335 Office Action dated Feb. 3, 2011.
U.S. Appl. No. 11/597,335 Office Action dated Oct. 28, 2010.
U.S. Appl. No. 12/255,540 Office Action dated Jul. 27, 2011.
U.S. Appl. No. 12/738,372 Office Action dated Jan. 15, 2013.
U.S. Appl. No. 13/100,058 Office Action dated May 24, 2012.
U.S. Appl. No. 13/100,107 Office Action dated Dec. 7, 2011.
U.S. Appl. No. 13/607,402 Office Action mailed Sep. 25, 2013.
U.S. Appl. No. 13/623,578 Final Office Action mailed Oct. 31, 2013.
U.S. Appl. No. 13/623,578 Office Action mailed Jul. 26, 2013.
U.S. Appl. No. 13/668,167 Office Action mailed May 6, 2013.
U.S. Appl. No. 13/668,167 Office Action mailed Nov. 25, 2013.
Verner et al. Development of serine protease inhibitors displaying multicentered short (<2.3 ANG) hydrogen bond binding mode: Inhibitors of urokinase-type plasminogen activator and factor Xa. J. Med. Chem. 44:2753-2771 (2001).
Young et al. Optimization of a screening lead for factor VIIa/TF. Bioorg. Med. Chem. Ltrs. 11(17):2253-2256 (2001).
U.S. Appl. No. 14/049,143 Non-Final Office Action mailed Mar. 16, 2015.
U.S. Appl. No. 14/250,936 Office Action dated Apr. 27, 2015.

* cited by examiner

2-(2-HYDROXYBIPHENYL-3-YL)-1H-BENZOIMIDAZOLE-5-CARBOXAMIDINE DERIVATIVES AS FACTOR VIIA INHIBITORS

CROSS-REFERENCE

This application is a continuation of U.S. patent application Ser. No. 13/607,402, filed Sep. 7, 2012, now U.S. Pat. No. 8,778,625, issued on Jul. 15, 2014, which is a continuation of U.S. patent application Ser. No. 13/100,107, now U.S. Pat. No. 8,299,110, issued on Oct. 30, 2012, which is a continuation of U.S. patent application Ser. No. 12/255,540, filed Oct. 21, 2008, which is divisional of U.S. patent application Ser. No. 10/537,115, now U.S. Pat. No. 7,479,502, issued on Jan. 20, 2009, which is the National Phase entry of International Application No. PCT/US2003/038635, filed on Dec. 3, 2003, which claims the benefit of U.S. Provisional Application No. 60/430,981, filed on Dec. 3, 2002, all of which are incorporated herein by reference in their entireties.

BACKGROUND OF THE INVENTION

1. Field of Invention

The present invention relates to novel inhibitors of Factors VIIa, IXa, Xa, XIa, in particular Factor VIIa, pharmaceutical compositions comprising these inhibitors, and methods for using these inhibitors for treating or preventing thromboembolic disorders. Processes for preparing these inhibitors are also disclosed.

2. State of the Art

Thrombosis results from a complex sequence of biochemical events, known as the coagulation cascade. A triggering event in coagulation is the binding of the serine protease Factor VIIa (FVIIa) found in the circulation, to tissue factor (TF), a receptor which is found on the surface of blood vessels after damage or inflammation. Once bound to TF, Factor VIIa catalyzes the formation of the serine protease Factor Xa, which subsequently forms the final protease in the cascade, thrombin.

The clinical manifestations of thrombosis range from acute myocardial infarction (AMI or heart attack) and unstable angina (UA) which occur in the key blood vessels of the heart (coronary vasculature) to deep vein thrombosis (DVT) which is the formation of blood clots in lower extremities which often follows orthopedic surgery on the hip and knee, as well as general abdominal surgery and paralysis. Formation of DVT is a risk factor for the development of pulmonary embolism (PE) in which part of a blood clot formed in the lower extremities, breaks off and travels to the lung where it blocks the flow of blood. The unpredictable development of PE often leads to a fatal outcome. Thrombosis can also be generalized systemically, with microclot formation occurring throughout the vascular system. This condition, known as disseminated intravascular coagulation (DIC), can be a consequence of certain viral diseases such as Ebola, certain cancers, sepsis and rheumatoid arthritis. Severe DIC can lead to a dramatic reduction in the coagulation factors due to the excessive activation of the clotting response which may result in multiple organ failure, hemorrhage and death.

The formation or embolization of blood clots in the blood vessels of the brain is the key event resulting in ischemic stroke. Triggering factors that lead to stroke are atrial fibrillation or abnormal rhythm of the atria of the heart and atherosclerosis followed by thrombosis in the main artery leading from the heart to the brain (carotid artery). Over 600,000 individuals suffer strokes each year in the U.S. Two-thirds of these stroke victims suffer some disability, and one-third suffer permanent and severe disability. Accordingly, there is a need for antithrombotic agents for the treatment of a variety of thrombotic conditions. The present invention fulfills this and related needs.

SUMMARY OF THE INVENTION

In one aspect this invention is directed to a compound of Formula I:

wherein:

$X^1$, $X^2$, $X^3$, and $X^4$ are independently —N— or —$CR^5$— wherein $R^5$ is hydrogen, alkyl, or halo with the proviso that not more than three of $X^1$, $X^2$, $X^3$ and $X^4$ are —N—;

$R^1$ is hydrogen, alkyl, halo, carboxy or aminocarbonyl;

$R^2$ is hydrogen, alkyl, or halo;

$R^3$ is hydrogen, halo, alkyl, alkoxy, haloalkyl, haloalkoxy, haloalkylthio, haloalkylsulfonyl, cyanoalkyl, tetrazol-5-yl, -(alkylene)-tetrazol-5-yl, hydroxyalkylcarbonyl, aminosulfonyl, alkylaminosulfonyl, dialkylaminosulfonyl, —$NHSO_2R$ (where R is alkyl, aryl, aralkyl, heteroaryl, heteroaralkyl, cycloalkyl, cycloalkylalkyl, heterocycloalkyl or heterocycloalkylalkyl), —$SO_2NHCOR^6$ (where $R^6$ is alkyl, aryl, aralkyl, heteroaryl, heteroaralkyl, heterocycloalkyl, or heterocycloalkylalkyl), —$SO_3H$, -(alkylene)-$SO_3H$, —$CONR^7R^8$ (where $R^7$ is hydrogen, alkyl, hydroxyalkyl, alkoxyalkyl and $R^8$ is hydrogen, alkyl, hydroxyalkyl, alkoxyalkyl, aminoalkyl, aryl, aralkyl, heteroaryl, heteroaralkyl, or hetereocycloalkylalkyl, or $R^7$ and $R^8$ together with the nitrogen atom to which they are attached form heterocycloalkylamino), -(alkylene)-$CONR^9R^{10}$ (where $R^9$ is hydrogen, alkyl, hydroxyalkyl, alkoxyalkyl and $R^{10}$ is hydrogen, alkyl, hydroxyalkyl, alkoxyalkyl, aminoalkyl, aryl, aralkyl, heteroaryl, heteroaralkyl, or heterocycloalkylalkyl, or $R^9$ and $R^{10}$ together with the nitrogen atom to which they are attached form heterocycloalkylamino), —$CONHSO_2R^{11}$ (where $R^{11}$ is alkyl, aryl, aralkyl, heteroaryl, heteroaralkyl, heterocyclalkyl, or heterocycloalkylalkyl), -(alkylene)-$CONHSO_2R^{11}$ (where $R^{11}$ is alkyl, aryl, aralkyl, heteroaryl, heteroaralkyl, heterocycloalkyl, or heterocycloalkylalkyl), aminoalkyloxy, carboxyalkyloxy, aminocarbonylalkyloxy, hydroxyalkyloxy, —O—$(CH_2CH_2$—O$)_n$—$OR^b$ (where n is an integer from 1 to 6 and $R^b$ is hydrogen or alkyl), —NHCO-(alkylene)-$R^a$ (where $R^a$ is hydroxy, alkoxy, or —$NR^7R^8$ where $R^7$ and $R^8$ are as defined above), —$OPO_3H_2$, or -(alkylene)-$OPO_3H_2$;

$R^x$ is hydrogen, alkyl, alkylthio, halo, hydroxy, hydroxyalkyl, alkoxy, aminosulfonyl, alkylaminosulfonyl, dialkylaminosulfonyl, or nitro;

$R^y$ is hydrogen, alkyl, or halo;

$R^z$ is hydrogen, alkyl, haloalkyl, cycloalkyl, alkylthio, halo, hydroxy, hydroxyalkyl, nitro, cyano, alkoxy, alkoxyalkyl, alkoxyalkyloxy, hydroxyalkyloxy, aminoalkyloxy, carboxyalkyloxy, aminocarbonylalkyloxy, haloalkoxy, carboxy, carboxyalkyl, alkoxycarbonyl, alkoxycarbonylalkyl, cyanoalkyl, alkylsulfonyl, alkylsulfonylalkyl, arylsulfonyl, heteroarylsulfonyl, carbamimidoyl, hydroxycarbamimidoyl, alkoxycarbamimidoyl, alkylsulfonylamino, alkylsulfonylaminoalkyl, alkoxysulfonylamino, alkoxysulfonylaminoalkyl, heterocycloalkylalkylaminocarbonyl, hydroxyalkoxyalkylaminocarbonyl, heterocycloalkylcarbonyl, heterocycloalkylcarbonylalkyl, heterocycloalkyl, heterocycloalkylalkyl, oxoheterocycloalkyl, oxoheterocycloalkylalkyl, heteroaryl, heteroaralkyl, ureido, alkylureido, dialkylureido, ureidoalkyl, alkylureidoalkyl, dialkylureidoalkyl, thioureido, thioureidoalkyl, —$COR^{12}$ (where $R^{12}$ is alkyl, haloalkyl, hydroxyalkyl, alkoxyalkyl, or aminoalkyl), -(alkylene)-$COR^{12}$ (where $R^{12}$ is alkyl, haloalkyl, hydroxyalkyl, alkoxyalkyl, or aminoalkyl), —$CONR^{14}R^{15}$ (where $R^{14}$ is hydrogen or alkyl and $R^{15}$ is hydrogen, alkyl, hydroxyalkyl, alkoxyalkyl, aryl, aralkyl, heteroaryl, or heteroaralkyl), -(alkylene)-$CONR^{16}R^{17}$ (where $R^{16}$ is hydrogen, alkyl or hydroxyalkyl and $R^{17}$ is hydrogen, alkyl, hydroxyalkyl, alkoxyalkyl, aryl, aralkyl, heteroaryl, or heteroaralkyl), —$NR^{18}R^{19}$ (where $R^{18}$ is hydrogen or alkyl and $R^{19}$ is hydrogen, alkyl, acyl, aryl, aralkyl, heteroaryl, or heteroaralkyl), -(alkylene)-$NR^{20}R^{21}$ (where $R^{20}$ is hydrogen, alkyl, or hydroxyalkyl and $R^{21}$ is hydrogen, alkyl, acyl, alkoxycarbonyl, hydroxyalkyl, alkoxyalkyl, aryl, aralkyl, heteroaryl, or heteroaralkyl), —$SO_2NR^{22}R^{23}$ (where $R^{22}$ is hydrogen or alkyl and $R^{23}$ is hydrogen, alkyl, aryl, aralkyl, heteroaryl, or heteroaralkyl, or $R^{22}$ and $R^{23}$ together with the nitrogen atom to which they are attached from heterocycloamino), -(alkylene)-$SO_2NR^{24}R^{25}$ (where $R^{24}$ is hydrogen or alkyl and $R^{25}$ is hydrogen, alkyl, aryl, aralkyl, heteroaryl, or heteroaralkyl or $R^{24}$ and $R^{25}$ together with the nitrogen atom to which they are attached from heterocycloamino), —$NR^{26}SO_2NR^{27}R^{28}$ (where $R^{26}$ and $R^{27}$ are independently hydrogen or alkyl, and $R^{28}$ is hydrogen, alkyl, aryl, aralkyl, heteroaryl, or heteroaralkyl or $R^{27}$ and $R^{28}$ together with the nitrogen atom to which they are attached from heterocycloamino), -(alkylene)-$NR^{29}SO_2NR^{30}R^{31}$ (where $R^{29}$ and $R^{30}$ are independently hydrogen or alkyl, and $R^{31}$ is hydrogen, alkyl, aryl, aralkyl, heteroaryl, or heteroaralkyl or $R^{30}$ and $R^{31}$ together with the nitrogen atom to which they are attached from heterocycloamino), —CONH-(alkylene)-$NR^{32}R^{33}$ where $R^{32}$ is hydrogen or alkyl and $R^{33}$ is alkyl), or aralkyl; and $R^{13}$ is hydrogen, hydroxy, $(C_{1-10})$alkoxy, —$C(O)R^{35}$ where $R^{35}$ is alkyl, aryl, haloalkyl, or cyanoalkyl, or —$C(O)OR^{36}$ where $R^{36}$ is alkyl, hydroxyalkyl, alkoxyalkyl, alkoxycarbonylalkyl, acyl, aryl, or haloalkyl; and individual isomers, mixture of isomers, or a pharmaceutically acceptable salt thereof, provided that when $R^3$ is hydrogen, halo, alkyl, alkoxy, haloalkyl, haloalkoxy, —$NHSO_2R$, tetrazol-5-yl, -(alkylene)-tetrazol-5-yl, —$CONR^7R^8$ (where $R^7$ is hydrogen or alkyl, and $R^8$ is hydrogen or alkyl), -(alkylene)-$CONR^9R^{10}$ (where $R^9$ and $R^{10}$ together with the nitrogen atom to which they are attached form pyrrolidinyl, aminoalkyloxy, carboxyalkyloxy, or aminocarbonylalkyloxy; and $R^z$ is hydrogen, alkyl, haloalkyl, halo, nitro, alkoxy, haloalkyl, carboxy, alkoxycarbonyl, —$NR^{18}R^{19}$ (where $R^{18}$ is hydrogen or alkyl and $R^{19}$ is hydrogen, alkyl, aryl or aralkyl), pyrrolidinylcarbonyl, —$SO_2NR^{22}R^{23}$ (where $R^{22}$ and $R^{23}$ are alkyl), carbamimidoyl, alkylsulfonylamino, alkylthio, ureido, —$NHC(S)NH_2$ or heterocycloamino, then $R^x$ is hydroxy or hydroxyalkyl.

In one aspect this invention is directed to a compound of Formula I:

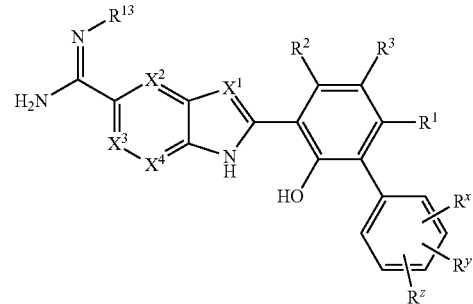

wherein:

$X^1$, $X^2$, $X^3$, and $X^4$ are independently —N— or —$CR^5$— wherein $R^5$ is hydrogen, alkyl, or halo with the proviso that not more than three of $X^1$, $X^2$, $X^3$ and $X^4$ are —N—;

$R^1$ is hydrogen, alkyl, halo, carboxy or aminocarbonyl;

$R^2$ is hydrogen, alkyl, or halo;

$R^3$ is hydrogen, halo, alkyl, alkoxy, haloalkyl, haloalkoxy, haloalkylthio, haloalkylsulfonyl, cyanoalkyl, tetrazol-5-yl, tetrazol-5-ylalkyl, hydroxyalkylcarbonyl, aminosulfonyl, alkylaminosulfonyl, dialkylaminosulfonyl, oxalyl, —$NHSO_2R$ (where R is alkyl, aryl, aralkyl, heteroaryl, heteroaralkyl, cycloalkyl, cycloalkylalkyl, heterocycloalkyl or heterocycloalkylalkyl), —$SO_2NHCOR^6$ (where $R^6$ is alkyl, aryl, aralkyl, heteroaryl, heteroaralkyl, heterocycloalkyl, or heterocycloalkylalkyl), —$SO_3H$, -(alkylene)-$SO_3H$, —$CONR^7R^8$, —$CHCF_3NR^7R^8$ or —$COCONR^7R^8$ (where $R^7$ is hydrogen, alkyl, hydroxyalkyl, alkoxyalkyl, carboxyalkyl, sulfoalkyl or phosphonoalkyl and $R^8$ is hydrogen, hydroxy, alkyl, hydroxyalkyl, alkoxyalkyl, aminoalkyl, carboxyalkyl, sulfoalkyl, phosphonoalkyl, aminocarboxyalkyl, aminocarbonylcarboxyalkyl, trimethylammonioalkyl, aminocarbonylalkyl, -(alkylene)-$(OCH_2CH_2)_n R^b$ (where n is an integer from 1 to 6 and $R^b$ is hydrogen, alkyl, hydroxy, alkoxy, amino or alkylcarbonylamino), aryl, aralkyl, heteroaryl, heteroaralkyl, hetereocycloalkylalkyl, hetereocycloalkylaminocarbonylalkyl or 3-heterocycloalkyl-2-hydroxypropyl or $R^7$ and $R^8$ together with the nitrogen atom to which they are attached form heterocycloalkylamino), -(alkylene)-$CONR^9R^{10}$ or -(alkylene)-$CHCF_3NR^9R^{10}$ (where $R^9$ is hydrogen, hydroxy, alkyl, hydroxyalkyl, alkoxyalkyl, aminoalkyl, carboxyalkyl, sulfoalkyl or phosphonoalkyl and $R^{10}$ is hydrogen, hydroxy, alkyl, hydroxyalkyl, alkoxyalkyl, aminoalkyl, carboxyalkyl, sulfoalkyl, phosphonoalkyl, aminocarboxyalkyl, aminocarbonylcarboxyalkyl, trimethylammonioalkyl, aminocarbonylalkyl, -(alkylene)-$(OCH_2CH_2)_n R^b$ (where n is an integer from 1 to 6 and $R^b$ is hydrogen, alkyl, hydroxy, alkoxy, amino or alkylcarbonylamino), aryl, aralkyl, heteroaryl, heteroaralkyl, hetereocycloalkylalkyl, hetereocycloalkylaminocarbonylalkyl or 3-heterocycloalkyl-2-hydroxypropyl or $R^9$ and $R^{10}$ together with the nitrogen atom to which they are attached form heterocycloalkylamino), —$CONHSO_2R^{11}$ (where $R^{11}$ is alkyl, aryl, aralkyl, heteroaryl, heteroaralkyl, heterocyclalkyl, or heterocycloalkylalkyl), -(alkylene)-$CONHSO_2R^{11}$ (where $R^{11}$ is alkyl, aryl, aralkyl, heteroaryl, heteroaralkyl, heterocycloalkyl, or heterocycloalkylalkyl), aminoalkyloxy, carboxyalkyloxy, aminocarbonylalkyloxy, hydroxyalkyloxy, -$(OCH_2CH_2)_n$—$R^b$ (where n is an integer from 1 to 6 and $R^b$ is hydrogen, alkyl, hydroxy, alkoxy, amino or alkylcarbonylamino), —NHCO-(alkylene)-$R^a$ (where $R^a$ is hydroxy, alkoxy, or —$NR^7R^8$ where $R^7$ and $R^8$ are as defined above), —$OPO_3H_2$, or -(alkylene)-$OPO_3H_2$;

$R^x$ is hydrogen, alkyl, alkylthio, halo, hydroxy, hydroxyalkyl, alkoxy, aminosulfonyl, alkylaminosulfonyl, dialkylaminosulfonyl, or nitro;

$R^y$ is hydrogen, alkyl, or halo;

$R^z$ is hydrogen, alkyl, haloalkyl, cycloalkyl, alkylthio, halo, hydroxy, hydroxyalkyl, nitro, cyano, alkoxy, alkoxyalkyl, alkoxyalkyloxy, hydroxyalkyloxy, aminoalkyloxy, carboxyalkyloxy, aminocarbonylalkyloxy, haloalkoxy, carboxy, carboxyalkyl, alkoxycarbonyl, alkoxycarbonylalkyl, cyanoalkyl, alkylsulfonyl, alkylsulfonylalkyl, arylsulfonyl, heteroarylsulfonyl, carbamimidoyl, hydroxycarbamimidoyl, alkoxycarbamimidoyl, alkylsulfonylamino, alkylsulfonylaminoalkyl, alkoxysulfonylamino, alkoxysulfonylaminoalkyl, heterocycloalkylalkylaminocarbonyl, hydroxyalkoxyalkylaminocarbonyl, heterocycloalkylcarbonyl, heterocycloalkylcarbonylalkyl, heterocycloalkyl, heterocycloalkylalkyl, oxoheterocycloalkyl, oxoheterocycloalkylalkyl, heteroaryl, heteroaralkyl, ureido, alkylureido, dialkylureido, ureidoalkyl, alkylureidoalkyl, dialkylureidoalkyl, thioureido, thioureidoalkyl, —$COR^{12}$ (where $R^{12}$ is alkyl, haloalkyl, hydroxyalkyl, alkoxyalkyl, or aminoalkyl), -(alkylene)-$COR^{12}$ (where $R^{12}$ is alkyl, haloalkyl, hydroxyalkyl, alkoxyalkyl, or aminoalkyl), —$CONR^{14}R^{15}$ (where $R^{14}$ is hydrogen or alkyl and $R^{15}$ is hydrogen, alkyl, hydroxyalkyl, alkoxyalkyl, aryl, aralkyl, heteroaryl or heteroaralkyl or $R^{14}$ and $R^{15}$ together with the nitrogen atom to which they are attached from heterocycloamino), -(alkylene)-$CONR^{16}R^{17}$ (where $R^{16}$ is hydrogen, alkyl or hydroxyalkyl and $R^{17}$ is hydrogen, alkyl, hydroxyalkyl, alkoxyalkyl, aryl, aralkyl, heteroaryl or heteroaralkyl or $R^{14}$ and $R^{15}$ together with the nitrogen atom to which they are attached from heterocycloamino), —$NR^{18}R^{19}$ (where $R^{18}$ is hydrogen or alkyl and $R^{19}$ is hydrogen, alkyl, acyl, aryl, aralkyl, heteroaryl, or heteroaralkyl), -(alkylene)-$NR^{20}R^{21}$ (where $R^{20}$ is hydrogen, alkyl, or hydroxyalkyl and $R^{21}$ is hydrogen, alkyl, acyl, alkoxycarbonyl, hydroxyalkyl, alkoxyalkyl, aryl, aralkyl, heteroaryl or heteroaralkyl), —$SO_2NR^{22}R^{23}$ (where $R^{22}$ is hydrogen or alkyl and $R^{23}$ is hydrogen, alkyl, aryl, aralkyl, heteroaryl or heteroaralkyl or $R^{22}$ and $R^{23}$ together with the nitrogen atom to which they are attached from heterocycloamino), -(alkylene)-$SO_2NR^{24}R^{25}$ (where $R^{24}$ is hydrogen or alkyl and $R^{25}$ is hydrogen, alkyl, aryl, aralkyl, heteroaryl or heteroaralkyl or $R^{24}$ and $R^{25}$ together with the nitrogen atom to which they are attached from heterocycloamino), —$NR^{26}SO_2NR^{27}R^{28}$ (where $R^{26}$ and $R^{27}$ are independently hydrogen or alkyl, and $R^{28}$ is hydrogen, alkyl, aryl, aralkyl, heteroaryl or heteroaralkyl or $R^{27}$ and $R^{28}$ together with the nitrogen atom to which they are attached from heterocycloamino), -(alkylene)-$NR^{29}SO_2NR^{30}R^{31}$ (where $R^{29}$ and $R^{30}$ are independently hydrogen or alkyl, and $R^{31}$ is hydrogen, alkyl, aryl, aralkyl, heteroaryl or heteroaralkyl or $R^{30}$ and $R^{31}$ together with the nitrogen atom to which they are attached from heterocycloamino), —CONH-(alkylene)-$NR^{32}R^{33}$ where $R^{32}$ is hydrogen or alkyl and $R^{33}$ is alkyl), or aralkyl; and $R^{13}$ is hydrogen, hydroxy, $(C_{1-10})$alkoxy, —$C(O)R^{35}$ where $R^{35}$ is alkyl, aryl, haloalkyl, or cyanoalkyl, or —$C(O)OR^{36}$ where $R^{36}$ is alkyl, hydroxyalkyl, alkoxyalkyl, alkoxycarbonylalkyl, acyl, aryl, or haloalkyl; and individual isomers, mixture of isomers, or a pharmaceutically acceptable salt thereof, provided that when $R^3$ is hydrogen, halo, alkyl, alkoxy, haloalkyl, haloalkoxy, —$NHSO_2R$, tetrazol-5-yl, tetrazol-5-ylalkyl, —$CONR^7R^8$ (where $R^7$ is hydrogen or alkyl, and $R^8$ is hydrogen or alkyl), -(alkylene)-$CONR^9R^{10}$ (where $R^9$ and $R^{10}$ together with the nitrogen atom to which they are attached form pyrrolidinyl), aminoalkyloxy, carboxyalkyloxy, or aminocarbonylalkyloxy;

and $R^z$ is hydrogen, alkyl, haloalkyl, halo, nitro, alkoxy, haloalkyl, carboxy, alkoxycarbonyl, —$NR^{18}R^{19}$ (where $R^{18}$ is hydrogen or alkyl and $R^{19}$ is hydrogen, alkyl, aryl or aralkyl), pyrrolidinylcarbonyl, —$SO_2NR^{22}R^{23}$ (where $R^{22}$ and $R^{23}$ are alkyl), carbamimidoyl, alkylsulfonylamino, alkylthio, ureido, —$NHC(S)NH_2$ or heterocycloamino, then $R^x$ is hydroxy or hydroxyalkyl.

In a second aspect, this invention is directed to a pharmaceutical composition comprising a pharmaceutically acceptable carrier and a therapeutically effective amount of a compound of Formula I or a pharmaceutically acceptable salt thereof. The pharmaceutical composition can contain individual stereoisomers or mixtures of stereoisomers of a compound of Formula I.

In a third aspect, this invention is directed to a method of treating a disease in an animal that is mediated by Factors VIIa, IXa, Xa and/or XIa, preferably VIIa, which method comprises administering to said animal a pharmaceutical composition comprising a pharmaceutically acceptable carrier and a therapeutically effective amount of a compound of Formula I or a pharmaceutically acceptable salt thereof. The pharmaceutical composition can contain individual stereoisomers or mixture of stereoisomers of a compound of Formula I. Preferably, the disorder is a thromboembolic disorder or cancer or rheumatoid arthritis, more preferably a thromboembolic disorder.

In a fourth aspect, this invention is directed to a method of treating a thromboembolic disorder in an animal which method comprises administering to said animal a pharmaceutical composition comprising a pharmaceutically acceptable carrier and a therapeutically effective amount of a compound of Formula I or a pharmaceutically acceptable salt thereof in combination with another anticoagulant agent(s) independently selected from a group consisting of a thrombin inhibitor, factor IXa inhibitor, factor Xa inhibitor, Aspirin®, and Plavix®.

In a fifth aspect, this invention is directed to a method for inhibiting the coagulation of a biological sample (e.g., stored blood products and samples) comprising the administration of a compound of Formula I or a pharmaceutically acceptable salt thereof.

In a sixth aspect, this invention directed to the use of a compound of Formula I or a pharmaceutically acceptable salt thereof in the preparation of a medicament for use in the treatment of a thromboembolic disorder or cancer or rheumatoid arthritis in an animal. Preferably, the disorder is a thromboembolic disorder.

In a seventh aspect, this invention is directed to an intermediate of Formula II:

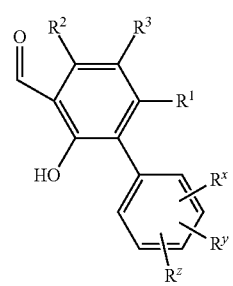

wherein $R^1$, $R^2$, $R^3$, $R^x$, $R^y$, and $R^z$ are as defined in their broadest terms for compounds of Formula I herein.

In an eighth aspect, this invention is directed to a process of preparing a compound of Formula I where $X^1$ is —N— comprising reacting a compound of Formula II with a compound of Formula III:

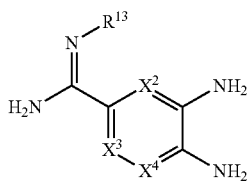

where $R^{13}$ is hydrogen;
optionally modifying any of the $R^1$, $R^2$, $R^3$, $R^x$, $R^y$, $R^z$, and $R^{13}$ groups;
optionally isolating individual isomers;
optionally preparing an acid addition salt; and
optionally preparing a free base.

In a ninth aspect, this invention is directed to a process of preparing a compound of Formula I where $X^1$ is —CH— and $R^{13}$ is hydrogen, comprising reacting a compound of Formula IV:

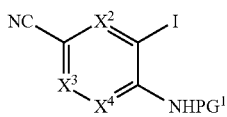

where $X^2$, $X^3$, $X^4$ are as defined in the Summary of the Invention and $PG^1$ is a suitable amino protecting group;
with a compound of Formula V

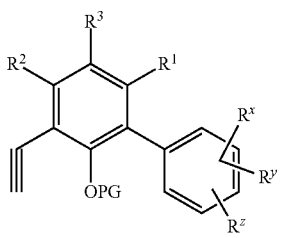

where $R^1$, $R^2$, $R^3$, $R^x$, $R^y$, and $R^z$ are as defined in the Summary of the Invention and PG is a suitable hydroxy protecting group; to give a compound of Formula VI:

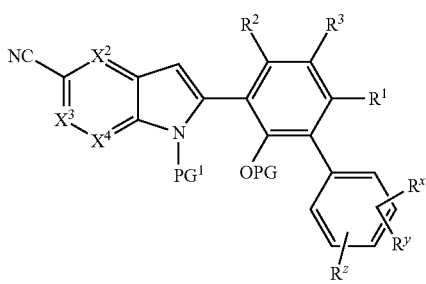

optionally removing the amino and/or hydroxy protecting group;
converting the cyano to a carbamimidoyl group;
optionally removing the amino and/or hydroxy protecting group;
optionally modifying any of the $R^1$, $R^2$, $R^3$, $R^x$, $R^y$, $R^z$, and $R^{13}$ groups;
optionally isolating individual isomers;
optionally preparing an acid addition salt; and
optionally preparing a free base.

DETAILED DESCRIPTION OF THE INVENTION

Definitions

The following terms, as used in the present specification and claims, are intended to have the meanings as defined below, unless indicated otherwise or used in naming a compound.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"Alkylene" means a linear saturated divalent hydrocarbon radical of one to six carbon atoms or a branched saturated divalent hydrocarbon radical of three to six carbon atoms e.g., methylene, ethylene, propylene, 1-methylpropylene, 2-methylpropylene, butylene, pentylene, and the like.

"Alkenylene" means a linear divalent hydrocarbon radical of two to six carbon atoms or a branched saturated divalent hydrocarbon radical of three to six carbon atoms containing one or two double bonds e.g., ethenylene, propenylene, 2-methylpropenylene, and the like.

"Alkylthio" means a radical —SR where R is alkyl as defined above, e.g., methylthio, ethylthio, propylthio (including all isomeric forms), butylthio (including all isomeric forms), and the like.

"Amino" means the radical —NRR' where R and R' are independently hydrogen, alkyl, or —COR$^a$ where R$^a$ is alkyl, e.g., —NH$_2$, methylaminoethyl, 1,3-diaminopropyl, acetylaminopropyl, and the like.

"Acyl" means a radical —COR' where R' is alkyl, alkoxy, haloalkyl, aminoalkyl, hydroxyalkyl, or alkoxyalkyl as defined herein, e.g., acetyl, trifluoroacetyl, hydroxymethylcarbonyl, and the like.

"Aminosulfonyl" or "sulfamoyl" means a radical —SO$_2$NH$_2$.

"Alkylaminosulfonyl" means a radical —SO$_2$NHR where R is alkyl as defined above, e.g., methylaminosulfonyl, ethylamino-sulfonyl, and the like.

"Alkylsulfonyl" means a radical —SO$_2$R where R is alkyl as defined above, e.g., methylsulfonyl, ethylsulfonyl, n- or iso-propylsulfonyl, and the like.

"Alkylsulfonylalkyl" means a radical -(alkylene)-SO$_2$R where R is alkyl as defined above, e.g., methylsulfonylmethyl, ethylsulfonylmethyl, n- or iso-propylsulfonylethyl, and the like.

"Alkylsulfonylamino" means a radical —NHSO$_2$R where R is alkyl as defined above, e.g., methylsulfonylamino, ethylsulfonylamino, n- or iso-propylsulfonylamino, and the like.

"Alkylsulfonylaminoalkyl" means a radical -(alkylene)-NHSO$_2$R where R is alkyl as defined above, e.g., methylsulfonylaminomethyl, ethylsulfonylaminomethyl, n- or iso-propylsulfonylaminoethyl, and the like.

"Alkoxysulfonylamino" means a radical —NHSO$_2$R where R is alkoxy as defined herein, e.g., methoxysulfonylamino, ethoxysulfonylamino, and the like.

"Alkoxysulfonylaminoalkyl" means a radical -(alkylene)-NHSO$_2$R where R is alkoxy as defined herein, e.g., methoxysulfonylaminomethyl, ethoxysulfonylaminomethyl, and the like.

"Alkoxy" means a radical —OR where R is alkyl as defined above, e.g., methoxy, ethoxy, propoxy, or 2-propoxy, n-, iso-, or tert-butoxy, and the like.

"Alkoxycarbonyl" means a radical —COOR where R is alkyl as defined above, e.g., methoxycarbonyl, ethoxycarbonyl, and the like.

"Alkoxycarbonylalkyl" means a radical -(alkylene)-COOR where R is alkyl as defined above, e.g., methoxycarbonylmethyl, ethoxycarbonylmethyl, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Aminoalkyl" means a linear monovalent hydrocarbon radical of one to six carbon atoms or a branched monovalent hydrocarbon radical of three to six carbons substituted with at least one, preferably one or two, —NRR' where R and R' are independently hydrogen, alkyl, or —COR$^a$ where R$^a$ is alkyl, e.g., aminomethyl, methylaminoethyl, 1,3-diaminopropyl, acetylaminopropyl, and the like.

"Aminocarboxyalkyl" means a linear monovalent hydrocarbon radical of one to six carbon atoms or a branched monovalent hydrocarbon radical of three to six carbons substituted with one —NRR' and —COOH where R and R' are independently hydrogen, alkyl, or —COR$^a$ where R$^a$ is alkyl, e.g., 1-amino-1-carboxypentyl, and the like.

"Aminocarbonylcarboxyalkyl" means a linear monovalent hydrocarbon radical of one to six carbon atoms or a branched monovalent hydrocarbon radical of three to six carbons substituted with one —CONRR' and —COOH where R and R' are independently hydrogen, alkyl, or —COR$^a$ where R$^a$ is alkyl, e.g., 1-aminocarbonyl-1-carboxypentyl, and the like.

"Aminocarbonylalkyl" means a linear monovalent hydrocarbon radical of one to six carbon atoms or a branched monovalent hydrocarbon radical of three to six carbons substituted with one or two —CONRR' where R and R' are independently hydrogen, alkyl, or —COR$^a$ where R$^a$ is alkyl, e.g., aminocarbonylmethyl, methylaminocarbonylmethyl, acetylaminocarbonylpropyl, and the like.

"Alkoxyalkyloxy" means a radical —OR where R is alkoxyalkyl, as defined above, e.g., 2-methoxyethyloxy, 1-, 2-, or 3-methoxypropyloxy, 2-ethoxyethyloxy, and the like.

"Aminoalkyloxy" means a radical —OR where R is aminoalkyl, as defined above, e.g., 2-aminoethyloxy, 1-, 2-, or 3-methylaminopropyloxy, and the like.

"Aminocarbonyl" or "carbamoyl" means a radical —CONH$_2$.

"Aminocarbonylalkyloxy" means a radical —O-alkylene-CONRR" where R and R' are independently hydrogen or alkyl, as defined above, e.g., 2-aminocarbonylethyloxy, aminocarbonylmethyloxy, and the like.

"Aminocarbonylalkyl" means a radical -(alkylene)-CONH$_2$, e.g., aminocarbonylmethyl, aminocarbonylethyl, 1-, 2-, or 3-aminocarbonylpropyl, and the like.

"Alkylureido" means a radical —NRCONHR' where R is hydrogen or alkyl and R' is alkyl, e.g., methylureidomethyl, and the like.

"Alkylureidoalkyl" means a radical -(alkylene)-NRCONHR' where R is hydrogen or alkyl and R' is alkyl, e.g., methylureidomethyl, and the like.

"Aryl" means a monovalent monocyclic or bicyclic aromatic hydrocarbon radical of 6 to 12 ring atoms, and optionally substituted independently with one or more substituents, preferably one, two, or three substituents, selected from alkyl, haloalkyl, alkoxy, alkylthio, halo, nitro, —COR (where R is alkyl), cyano, amino, alkylamino, dialkylamino, hydroxy, carboxy, or —COOR where R is alkyl. Representative examples include, but are not limited to, phenyl, biphenyl, 1-naphthyl, and 2-naphthyl and the derivatives thereof.

"Arylsulfonyl" means a radical —SO$_2$R where R is aryl as defined above, e.g., phenylsulfonyl, and the like.

"Aralkyl" means a radical -(alkylene)-R where R is an aryl group as defined above e.g., benzyl, phenylethyl, 3-(3-chlorophenyl)-2-methylpentyl, and the like.

"Alkoxycarbamimidoyl" means a radical —C(=NH)NHOR or —C(=NOR)NH$_2$ where R is alkyl as defined above, e.g., methoxycarbamimidoyl.

"Cycloalkyl" means a cyclic saturated monovalent hydrocarbon radical of three to six carbon atoms, e.g., cyclopropyl, cyclobutyl, and the like, preferably cyclopropyl.

"Carboxyalkyl" means a radical -(alkylene)-COOH, e.g., carboxymethyl, carboxyethyl, 1-, 2-, or 3-carboxypropyl, and the like.

"Carboxyalkyloxy" means a radical —O-(alkylene)-COOH, e.g., carboxymethyloxy, carboxyethyloxy, and the like.

"carbamimidoyl" means a radical —C(=NH)NH$_2$, or a protected derivative thereof.

"Cyanoalkyl" means a radical -(alkylene)-CN, e.g., cyanomethyl, cyanoethyl, cyanopropyl, and the like.

"Dialkylaminosulfonyl" means a radical —SO$_2$NRR' where R and R' are independently alkyl as defined above, e.g., dimethylaminosulfonyl, methylethylamino-sulfonyl, and the like.

"Dialkylureido" means a radical —NRCONR'R" where R is hydrogen or alkyl and R' and R" are independently alkyl, e.g., dimethylureido, and the like.

"Dialkylureidoalkyl" means a radical -(alkylene)-NRCONR'R" where R is hydrogen or alkyl and R' and R" are independently alkyl, e.g., dimethylureidomethyl, and the like.

"Guanidinoalkyl" means a linear monovalent hydrocarbon radical of one to six carbon atoms or a branched monovalent hydrocarbon radical of three to six carbons substituted with at least one, preferably one or two, —NRC(NRR')NRR' where R and R' are independently hydrogen, alkyl, or —COR$^a$ where R$^a$ is alkyl, e.g., guanidinomethyl, N'-methylaminoethyl, 2-(N',N',N",N"-tetramethyl-guanidino)-ethyl, and the like.

"Halo" means fluoro, chloro, bromo, and iodo, preferably fluoro or chloro.

"Haloalkyl" means alkyl substituted with one or more halogen atoms, preferably one to three halogen atoms, preferably fluorine or chlorine, including those substituted with different halogens, e.g., —CH$_2$Cl, —CF$_3$, —CHF$_2$, and the like.

"Haloalkoxy" means a radical —OR where R is haloalkyl as defined above, e.g., —OCH$_2$Cl, —OCF$_3$, —OCHF$_2$, and the like.

"Haloalkylthio" means a radial —SR where R is haloalkyl as defined above.

"Haloalkylsulfonyl" means a radial —SO$_2$R where R is haloalkyl as defined above.

"Hydroxyalkyl" means a linear monovalent hydrocarbon radical of one to six carbon atoms or a branched monovalent hydrocarbon radical of three to six carbons substituted with one to five hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Hydroxyalkyloxy" means a radical —OR where R is hydroxyalkyl as defined above, e.g., 2-hydroxyethyloxy, 3-hydroxypropyloxy, and the like.

"Hydroxyalkylcarbonyl" means a radical —COR where R is hydroxyalkyl as defined above. Representative examples include, but are not limited to, hydroxymethylcarbonyl, 2-hydroxyethylcarbonyl, and the like.

"Hydroxyalkoxyalkylaminocarbonyl" means a radical —CONH-(alkylene)-O-(alkylene)OH where alkylene is as defined above, e.g., —CONH—(CH$_2$)$_2$—O—(CH$_2$)$_2$OH and the like.

"Heterocycloalkyl" means a saturated or unsaturated monovalent cyclic group of 3 to 8 ring atoms in which one or two ring atoms are heteroatoms selected from N, O, or S(O)n, where n is an integer from 0 to 2, the remaining ring atoms being C. The heterocycloalkyl ring may be optionally substituted with one or more substituents, preferably one or two substituents, independently selected from alkyl, aryl, heteroaryl, aralkyl, 3,5,6-trihydroxy-2-hydroxymethyl-tetrahydropyran-3-yl, 4,5-dihydroxy-2-hydroxymethyl-6-(4,5,6-trihydroxy-2-hydroxymethyl-tetrahydro-pyran-3-yloxy)-tetrahydro-pyran-3-yl, heteroaralkyl, halo, haloalkyl, hydroxy, hydroxyalkyl, alkoxy, alkoxyalkyl, aminoalkyl, guanidinoalkyl, halo, cyano, carboxy, —COOR (where R is alkyl as define above), or —CONR$^a$R$^b$ (where R$^a$ and R$^b$ are independently hydrogen or alkyl), or a protected derivative thereof. More specifically the term heterocycloalkyl includes, but is not limited to, pyrrolidino, piperidino, morpholino, piperazino, tetrahydropyranyl, and thiomorpholino.

"Heterocycloalkylcarbonyl" means a radical —COR where R is heterocycloalkyl as defined above. More specifically the term heterocycloalkylcarbonyl includes, but is not limited to, 1-pyrrolidinocarbonyl, 1-piperidinocarbonyl, 4-morpholinocarbonyl, 1-piperazinocarbonyl, 2-tetrahydropyranylcarbonyl, and 4-thiomorpholinocarbonyl, and the derivatives thereof.

"Heterocycloalkylcarbonylalkyl" means a radical -(alkylene)-COR where R is heterocycloalkyl as defined above. More specifically the term heterocycloalkylcarbonyl includes, but is not limited to, 1-pyrrolidinocarbonylmethyl, 1-piperidinocarbonylmethyl, 4-morpholinocarbonylethyl, 1-piperazinocarbonylmethyl, and the derivatives thereof.

"Heterocycloalkylalkyl" means a radical -(alkylene)-R where R is heterocycloalkyl as defined above. More specifically the term heterocycloalkylalkyl includes, but is not limited to, pyrrolidin-1-ylmethyl, piperidin-1-ylmethyl, 2-morpholin-1-ylethyl, piperazin-1-ylethyl, and the derivatives thereof.

"Heterocycloalkylalkylaminocarbonyl" means a radical —CONH-(alkylene)-R where R is heterocycloalkyl as defined above. More specifically the term heterocycloalkylalkylamino-carbonyl includes, but is not limited to, 1-pyrrolidinoethyl-aminocarbonyl, 1-piperidinoethyl-aminocarbonyl, 4-morpholinoethylcarbonyl, 1-piperazinoethylaminocarbonyl, and 4-thiomorpholinopropylaminocarbonyl, and the derivatives thereof.

"Heteroaryl" means a monovalent monocyclic or bicyclic aromatic radical of 5 to 10 ring atoms containing one or more, preferably one or two ring heteroatoms selected from N, O, or S, the remaining ring atoms being carbon. The heteroaryl ring is optionally substituted with one or more substituents, preferably one or two substituents, independently selected from alkyl, haloalkyl, alkoxy, alkylthio, aminoalkyl, guanidinoalkyl, halo, nitro, cyano, amino, alkyl or dialkylamino, hydroxy, carboxy, or —COOR where R is alkyl as define above. More specifically the term heteroaryl includes, but is not limited to, pyridyl, pyrrolyl, imidazolyl, thienyl, furanyl, indolyl, quinolyl, pyrazine, pyrimidine, pyradizine, oxazole, isooxazolyl, benzoxazole, quinoline, isoquinoline, benzopyranyl, and thiazolyl.

"Heteroarylsulfonyl" means a radical —SO$_2$R where R is heteroaryl as defined above, e.g., pyridylsulfonyl, furanylsulfonyl, and the like.

"Heteroaralkyl" means a radical -(alkylene)-R where R is a heteroaryl group as defined above e.g., pyridylmethyl, furanylmethyl, indolylmethyl, pyrimidinylmethyl, and the like.

"Heterocycloamino" means a saturated or unsaturated monovalent cyclic group of 3 to 8 ring atoms in which one or two ring atoms are heteroatoms selected from N, O, or S(O)n, where n is an integer from 0 to 2, the remaining ring atoms being C provided that at least one of the heteroatom is nitrogen and wherein one or two carbon atoms are optionally replace by a carbonyl group. The heterocycloamino ring may be optionally substituted with one or more substituents, preferably one or two substituents, independently selected from alkyl, hydroxy, hydroxyalkyl, alkoxy, alkoxyalkyl, aminoalkyl, guanidinoalkyl, halo, haloalkyl, aryl, heteroaryl, aralkyl, heteroaralkyl, haloalkyl, halo, cyano, carboxy, —CONR$^a$R$^b$ (where R$^a$ and R$^b$ are independently hydrogen or alkyl), or —COOR where R is alkyl as define above. More specifically the term heterocycloamino includes, but is not limited to, pyrrolidino, piperidino, piperazino, and thiomorpholino, and the derivatives thereof.

"Hydroxycarbamimidoyl" means a radical —C(=NH)NHOH or —C(=NOH)NH$_2$.

The present invention also includes the prodrugs of compounds of Formula I. The term prodrug is intended to represent covalently bonded carriers, which are capable of releasing the active ingredient of Formula I, when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of Formula I include compounds wherein a hydroxy, carbamimidoyl, guanidino, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy functional groups in compounds of Formula I and the like. Prodrugs of compounds of Formula I are also within the scope of this invention.

The present invention also includes (derivatives and protected derivatives of compounds of Formula I. For example, when compounds of Formula I contain an oxidizable nitrogen atom (e.g., when a compound of Formula I contains a pyridine, amino, alkylamino, piperidino, piperazino, morpholino, or dialkylamino group), the nitrogen atom can be converted to an N-oxide by methods well known in the art.

Also when compounds of Formula I contain groups such as hydroxy, carboxy, carbonyl, thiol or any group containing a nitrogen atom(s), these groups can be protected with a suitable protecting groups. A comprehensive list of suitable protective groups can be found in T. W. Greene, *Protective*

Groups in Organic Synthesis, John Wiley & Sons, Inc. 1981, the disclosure of which is incorporated herein by reference in its entirety. The protected derivatives of compounds of Formula I can be prepared by methods well known in the art.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

The compounds of the present invention may have asymmetric centers. Compounds of the present invention containing an asymmetrically substituted atom may be isolated in optically active or racemic forms. It is well known in the art how to prepare optically active forms, such as by resolution of materials. Many geometric isomers of olefins, C=C double bonds, and the like can be present in the compounds described herein, and all such stable isomers are contemplated in the present invention. Cis and trans geometric isomers of the compounds of the present invention are described and may be isolated as a mixture of isomers or as separated isomeric forms. All chiral, enantiomeric, diastereomeric, racemic forms and all geometric isomeric forms of a structure (representing a compound of Formula I) are intended, unless the specific stereochemistry or isomeric form is specifically indicated.

Certain compounds of Formula I exist in tautomeric equilibrium. Compounds of Formula I, which exist as tautomers are named, illustrated or otherwise described in this application as one possible tautomer. However, it is to be understood that all possible tautomers are meant to be encompassed by such names, illustrations and descriptions and are within the scope of this invention. For example, in compound of Formula I, the group —C(=NR$^{13}$)NH$_2$ can tautomerize to —C(=NH)NHR$^{13}$ group. Additionally, as used herein the terms alkyl includes all the possible isomeric forms of said alkyl group albeit only a few examples are set forth. Furthermore, when the cyclic groups such as aryl, heteroaryl, heterocycloalkyl are substituted, they include all the positional isomers albeit only a few examples are set forth.

"Oxoheterocycloalkyl" means a saturated or unsaturated (provided that it is not aromatic) monovalent cyclic group of 3 to 8 ring atoms in which one or two ring atoms are heteroatoms selected from N, O, or S(O)n, where n is an integer from 0 to 2, the remaining ring atoms being C wherein one or two of the carbon atoms is/are replaced with an oxo (C=O) group. The oxoheterocycloalkyl ring may be optionally substituted with one or more substituents, preferably one or two substituents, independently selected from alkyl, aryl, heteroaryl, aralkyl, heteroaralkyl, haloalkyl, halo, hydroxy, hydroxyalkyl, alkoxyalkyl, aminoalkyl, guanidinoalkyl, alkoxy, cyano, carboxy, or —COOR where R is alkyl as define above. More specifically the term heterocycloalkyl; includes, but is not limited to, 2 or 3-oxopyrrolidin-1-yl, 2, 3, or 4-oxopiperidino, 3-oxomorpholino, 2-oxo-piperazino, 2-oxotetrahydropyranyl, 3-oxothiomorpholino, 2-imidazolidone, and the derivatives thereof.

"Oxoheterocycloalkylalkyl" means a radical -(alkylene)-R where R is a oxoheterocycloalkylalkyl group as defined above e.g., More specifically the term oxoheterocycloalkylalkyl; includes, but is not limited to, 2 or 3-oxopyrrolidin-1-yl-(methyl, ethyl, or propyl), 2, 3, or 4-oxopiperidin-1-yl-(methyl, ethyl, or propyl), 3-oxomorpholin4-yl-(methyl, ethyl, or propyl), 2-oxopiperazin-1-yl-(methyl, ethyl, or propyl), 2-oxotetrahydro-pyran-3-yl-(methyl, ethyl, or propyl), 3-oxothiomorpholin-4-yl-(methyl, ethyl, or propyl), 2-imidazolidon-1-yl-(methyl, ethyl, or propyl), and the derivatives thereof.

"Optional" or "optionally" means that the subsequently described event or circumstance may but need not occur, and that the description includes instances where the event or circumstance occurs and instances in which it does not. For example, "heterocycloalkyl group optionally mono- or di-substituted with an alkyl group" means that the alkyl may but need not be present, and the description includes situations where the heterocycloalkyl group is mono- or disubstituted with an alkyl group and situations where the heterocycloalkyl group is not substituted with the alkyl group.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Phosphoalkyl" means a linear monovalent hydrocarbon radical of one to six carbon atoms or a branched monovalent hydrocarbon radical of three to six carbons substituted with at least one, preferably one or two, —P(O)(OH)$_2$, e.g., phosphomethyl, 2-phosphoethyl, 1-methyl-2-phosphoethyl, 1,3-diphosphopropyl, and the like.

"Sulfoalkyl" means a linear monovalent hydrocarbon radical of one to six carbon atoms or a branched monovalent hydrocarbon radical of three to six carbons substituted with at least one, preferably one or two, —SOOH, e.g., sulfomethyl, 2-sulfoethyl, 1-methyl-2-sulfoethyl, 1,3-disulfopropyl, and the like.

"Treating" or "treatment" of a disease includes:
(1) preventing the disease, i.e. causing the clinical symptoms of the disease not to develop in a mammal that may be exposed to or predisposed to the disease but does not yet experience or display symptoms of the disease,
(2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound of Formula I that, when administered to a mammal for treating a disease, is sufficient to effect such treatment for the disease. The "therapeutically effective amount" will vary depending on the compound, the disease and its severity and the age, weight, etc., of the mammal to be treated.

"Thioureido" means a radical —NRC(S)NR'R" where R, R', and R" are independently hydrogen or alkyl.

"Thioureidoalkyl" means a radical -(alkylene)-NRC(S)NR'R" where alkylene is as defined above. Representative examples include but are not limited to thioureidomethyl, thioureidoethyl, and the like.

"Trimethylammonioalkyl" means a linear monovalent hydrocarbon radical of one to six carbon atoms or a branched monovalent hydrocarbon radical of three to six carbons substituted with one —N$^+$(CH$_3$), e.g., trimethylammoniomethyl, 2-ammonioethyl, and the like.

"Ureido" means a radical —NHCONH$_2$.

"Ureidoalkyl" means a radical -(alkylene)-NHCONH$_2$ where alkylene is as defined above. Representative examples include but are not limited to ureidomethyl, ureidoethyl, and the like.

The compounds of the present invention are numbered as follows:

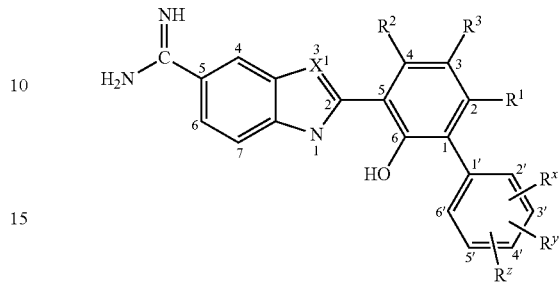

Representative compounds of Formula I where $R^1$, $R^2$ and $R^y$ are hydrogen; $X^1$ is —N—, $X^2$, $X^3$, and $X^4$ are carbon are disclosed in Table I below.

TABLE I

| Cpd. # | $R^3$ | Position, $R^x$ | Position, $R^z$ |
|---|---|---|---|
| 1 | —F | 2', —OH | 5', —CH$_2$NHCONH$_2$ |
| 2 | (N-acyl pyrrolidine-2-carboxamide, N,N-dimethyl) | 2', —OH | 5', —F |
| 3 | (N-(pyridin-4-ylmethyl)carbamoyl) | 2', —OH | 5', —F |
| 4 | (N-(pyridin-2-ylmethyl)carbamoyl) | 2', —OH | 5', —F |
| 5 | (4-hydroxypyrrolidine-1-carbonyl-2-carboxylic acid) | 2', —OH | 5', —F |

TABLE I-continued

[Core structure: 2-(2-hydroxy-3-R³-phenyl substituted biphenyl)-1H-benzimidazole-5-carboxamidine with positions labeled 1–6 on the central phenyl and 1'–6' on the pendant phenyl bearing Rx and Rz]

| Cpd. # | R³ | Position, Rx | Position, Rz |
|---|---|---|---|
| 6 | [furan-2-ylmethyl-NH-C(=O)–] | 2', —OH | 5', —F |
| 7 | [2-(pyridin-4-yl)ethyl-NH-C(=O)–] | 2', —OH | 5', —F |
| 8 | [pyrrolidine-2-carboxamide-1-yl-C(=O)–] | H | 3', —SO₂NH₂ |
| 9 | —CON(CH₃)₂ | H | 3', —SO₂NH₂ |
| 10 | —H | 2', —OH | 5', —CH₂NHCONH₂ |
| 11 | —H | 2', —OH | 5', —CH₂CONH₂ |
| 12 | —SO₂NH₂ | 2', —OH | 5', —CH₂NHCONH₂ |
| 13 | tetrazol-5-yl | 2', —OH | 5', —CH₂NHCONH₂ |
| 14 | —H | H | 3', —SO₂NH₂ |
| 15 | —CONHSO₂—(CH₂)₃CH₃ | H | 3', —SO₂NH₂ |
| 16 | [2-(pyridin-3-yl)ethyl-NH-C(=O)–] | 2', —OH | 5', —F |
| 17 | [2-(pyridin-2-yl)ethyl-NH-C(=O)–] | 2', —OH | 5', —F |
| 18 | [4-hydroxy-pyrrolidine-2-carboxylic acid methyl ester-1-yl-C(=O)–] | 2', —OH | 5', —F |
| 19 | —H | 2', —OCH₃ | 5', —F |
| 20 | —H | 2', —OH | 5', —F |
| 21 | —CH₂CN | 2', —OH | 5', —CH₂NHCONH₂ |
| 22 | [pyrrolidine-2-carboxamide-1-yl-C(=O)–] | 2', —OH | 5', —F |
| 23 | —CH₂CONHCH₃ | 2', —OH | 5', —CH₂NHCONH₂ |

TABLE I-continued

| Cpd. # | R³ | Position, Rx | Position, Rz |
|---|---|---|---|
| 24 | 3-phenylpropanoyl (PhCH₂CH₂C(=O)–) | 2', —OH | 5', —F |
| 25 | —CON(CH₃)₂ | 2', —OH | 5', —F |
| 26 | tetrazol-5-yl | H | 5', —CH₂NHCONHC(CH₃)₃ |
| 27 | tetrazol-5-ylmethyl | 2', —OH | 5', —CH₂NHCONH₂ |
| 28 | —(CH₂)₂CN | 2', —OH | 5', —CH₂NHCONH₂ |
| 29 | (1-acyl-pyrrolidine-2-carboxylic acid, L-prolyl) | 2', —OH | 5', —F |
| 30 | morpholinoethyl-NHC(=O)– | 2', —OH | 5', —F |
| 31 | —SO₂NHCOCH₃ | H | 3', —SO₂NH₂ |
| 32 | —SO₂NHCOCH₃ | H | 3', —NH₂ |
| 33 | (1-acyl-pyrrolidine-2-carboxylic acid, D-prolyl) | 2', OH | 5', —F |
| 34 | morpholine-4-carbonyl | 2', OH | 5', —F |
| 35 | pyrrolidine-1-carbonyl | 2', OH | 5', —F |
| 36 | 3-methylpiperazine-1-carbonyl | 2', OH | 5', —F |
| 37 | (2-acetylpyrrolidine-1-carbonyl) | 2', OH | 5', —F |

TABLE I-continued

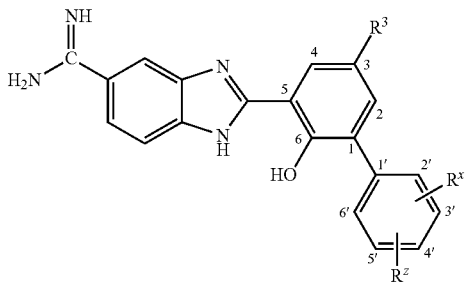

| Cpd. # | R³ | Position, Rx | Position, Rz |
|---|---|---|---|
| 38 | 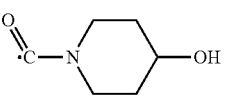 | 2', OH | 5', —F |
| 39 | 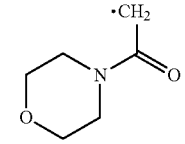 | 2', OH | 5', —F |
| 40 | 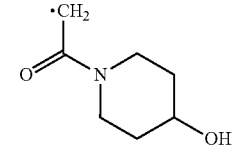 | 2', OH | 5', —F |
| 41 | 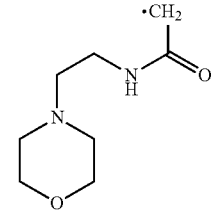 | 2', OH | 5', —F |
| 42 | tetrazol-5-yl | 2', OH | 5', —F |
| 43 | 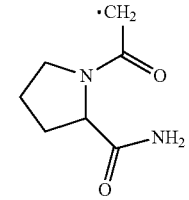 | 2', OH | 5', —F |
| 44 | —CH₂CON(CH₂CH₂OCH₃)₂ | 2', OH | 5', —F |
| 45 | —CH₂CONH(CH₂)₂OH | 2', OH | 5', —F |
| 46 | —CH₂CON(CH₂CH₂OH)₂ | 2', OH | 5', —F |
| 47 | —CH₂CONH(CH₂)₂OCH₃ | 2', OH | 5', —F |
| 48 | —CH₂CON(CH₃)₂ | 2', OH | 5', —F |
| 49 | —CH₂CONH(CH₂)₂N(CH₃)₂ | 2', OH | 5', —F |
| 50 | tetrazol-5-ylmethyl | H | 3', —SO₂NH₂ |
| 51 | —SO₂NH₂ | H | 3', —SO₂NH₂ |
| 52 | —CH₃ | H | 3', —SO₂NH₂ |
| 53 | —CH₂CN | H | 3', —SO₂NH₂ |
| 54 | tetrazol-5-yl | H | 3', —SO₂NH₂ |
| 55 | —Cl | 2', —OH | 5', —CH₂NHCONH₂ |
| 56 | tetrazol-5-yl | H | 5', —CH₂NHCONH₂ |
| 57 | tetrazol-5-ylmethyl | 2', —OH | 5', —CH₂NH₂ |
| 58 |  | 2', —OH | 5', —F |

TABLE I-continued

| Cpd. # | R³ | Position, Rx | Position, Rz |
|---|---|---|---|
| 59 | (3-carbamoylpiperidine-1-carbonyl) | H | 3', —SO₂NH₂ |
| 60 | (2-acetylpyrrolidine-1-carbonyl) | H | 3', —SO₂NH₂ |
| 61 | —CH₃ | 2', —OH | 5', —CH₂NHCONH₂ |
| 62 | —F | 2', —OH | 5', —CH₂NHCONH₂ |
| 63 | —Cl | 2', —OH | 5', HN-piperazine-C(O)-CH₂• |
| 64 | —CH₃ | 3', —Br | 4', —OH |
| 65 | —CH₃ | 2', —OH | 5', —CH₂COOH |
| 66 | —CH₃ | 2', —OH | 5', —CH₂CONH₂ |
| 67 | —H | 2', —OH | 5', —CH₂NHCOCH₃ |
| 68 | —H | 2', —OH | 5', —CH₂CONHCH₃ |
| 69 | (2-carboxypyrrolidine-1-carbonyl) | 2', —OH | 5', —F |
| 70 | (2-(methoxymethyl)pyrrolidine-1-carbonyl) | 2', —OH | 5', —F |
| 71 | —CON(CH₃)(CH₂CONH₂) | 2', —OH | 5', —F |
| 72 | (4-carboxythiazolidine-3-carbonyl) | 2', —OH | 5', —F |

TABLE I-continued

| Cpd. # | R³ | Position, Rx | Position, Rz |
|---|---|---|---|
| 73 | (pyridin-4-ylmethyl)carbamoyl | 2', —OH | 5', —F |
| 74 | 1-(N-methylcarbamoyl)pyrrolidine-2-carbonyl | 2', —OH | 5', —F |
| 75 | 4-hydroxy-2-carbamoylpyrrolidine-1-carbonyl | 2', —OH | 5', —F |
| 76 | 4-hydroxy-2-(methoxycarbonyl)pyrrolidine-1-carbonyl | 2', —OH | 5', —F |
| 77 | —CH₂CONHCH(CH₂OH)CH₂OH | 2', —OH | 5', —F |
| 78 | —H | 2', —OH | 5', —SO₂NH₂ |
| 79 | —H | 2', —OH | 5', —CH₂NHCOCH₂OH |
| 80 | —Cl | 2', —OH | 5', —CONH₂ |
| 81 | —H | 2', —OH | 5', —CONH₂ |
| 82 | —CH₃ | 2', —OH | 5', —CH₂NHCONH₂ |
| 83 | —H | 2', —OH | 5', —CH₂NHSO₂CH₃ |
| 84 | —H | 2', —OH | 5', —CH₂CON(CH₃)₂ |
| 85 | —Cl | 2', —OH | 5', —CH₂CONH₂ |
| 86 | —F | 2', —OH | 5', —CH₂COOH |
| 87 | —F | 2', —OH | 5', —CH₂CONH₂ |
| 88 | —CF₃ | 2', —OH | 5', —CONH₂ |
| 89 | —H | 2', —OH | 5', —CH₂NHCOOCH₃ |
| 90 | —H | 2', —F | 5', —CH₂NHCONH₂ |
| 91 | —H | 2', —OH | 5', —CH₂NHCON(CH₃)₂ |
| 92 | —OCH₃ | 2', —OH | 5', —CH₂NHCOCH₃ |
| 93 | —OCF₃ | 2', —OH | 5', —CH₂COOH |
| 94 | —SO₂N(CH₃)₂ | 2', —OH | 5', —CH₂NHCONH₂ |
| 95 | —H | 2', —OH | 5', —CH₂-(piperazin-1-yl-carbonyl) |
| 96 | —H | 2', —OH | 5', —CH₂CONH(CH₂)₂OH |

TABLE I-continued

| Cpd. # | R³ | Position, Rx | Position, Rz |
|---|---|---|---|
| 97 | —H | 2', —OH | 5', —CH₂-morpholine-C(O)- (morpholine carbonyl methyl) |
| 98 | N-C(O)- pyrrolidine-2-carboxamide | 2', —OH | 5', —CH₂NHCONH₂ |
| 99 | 3-carbamoyl-piperidine-1-carbonyl (H₂N-C(O)- piperidinyl-C(O)-) | 2', —OH | 5', —CH₂NHCONH₂ |
| 101 | —Cl | 2', —OH | 5', —CH₂-morpholine-C(O)- |
| 102 | —H | 2', —OH | 5', —CH₂OH |
| 103 | —OCH₃ | 2', —OH | 5', —CH₂COOH |
| 104 | —F | 2', —OH | 5', —CH₂NHC(O)CH₂OH |
| 105 | —CH₂C(O)NH(CH₂)₂N⁺(CH₃)₃ | 2', —OH | 5', —SO₂NH₂ |
| 106 | —C(O)N(CH₃)CH₂C(O)NH₂ | 2', —OH | 5', —SO₂NH₂ |
| 107 | 4-methylpiperazinyl-ethyl-NH-C(O)- | 2', —OH | 5', —SO₂NH₂ |
| 108 | 4-methylpiperazine-1-carbonyl | 2', —OH | 5', —SO₂NH₂ |
| 109 | piperazinyl-ethyl-NH-C(O)- | 2', —OH | 5', —SO₂NH₂ |
| 110 | morpholinyl-ethyl-NH-C(O)- | 2', —OH | 5', —SO₂NH₂ |
| 111 | —C(O)NH(CH₂)₂SO₃H | 2', —OH | 5', —SO₂NH₂ |
| 112 | —CH₂C(O)NH(CH₂)₄CH(NH₂)C(O)OH | 2', —OH | 5', —SO₂NH₂ |

TABLE I-continued

| Cpd. # | R³ | Position, Rx | Position, Rz |
|---|---|---|---|
| 113 | •CH₂—C(O)—N(piperazine)-N-methyl | 2', —OH | 5', —SO₂NH₂ |
| 114 | —S(O)₂—NH—C(O)—CH₂CH₂—phenyl | 2', —OH | —H |
| 115 | —S(O)₂—NH—C(O)—CH₂CH₂—phenyl | H | 3', —NO₂ |
| 116 | —S(O)₂—NH—C(O)—CH₂CH₂—(3-pyridyl) | H | 3', —NO2 |
| 117 | —S(O)₂—NH—C(O)—CH₂CH₂—(3-pyridyl) | H | 3', —NH₂ |
| 118 | —S(O)₂—NH—C(O)—CH₂CH₂—phenyl | H | 3', —NH₂ |
| 119 | —S(O)₂—NH—C(O)—CH₂CH₂—(3-pyridyl) | H | 3', —NHC(O)NH₂ |
| 120 | —S(O)₂—NH—C(O)—CH₂CH₂—(3-piperidyl) | H | 3', —NH₂ |

TABLE I-continued

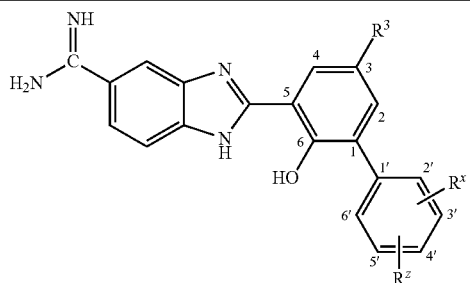

| Cpd. # | R³ | Position, Rx | Position, Rz |
|---|---|---|---|
| 121 | (structure: acetamido-asparagine-like, —CH₂-NH-C(O)-CH(C(O)NH₂)-... with COOH) | 2', —OH | 5', —SO₂NH₂ |
| 122 | —CH₂C(O)N(CH₂COOH)₂ | 2', —OH | 5', —SO₂NH₂ |
| 123 | (structure: acetamido-aspartic acid-like) | 2', —OH | 5', —SO₂NH₂ |
| 124 | (structure: •CH₂-C(O)-prolinamide) | 2', —OH | 5', —SO₂NH₂ |
| 125 | (structure: •CH₂-C(O)-4-hydroxyproline) | 2', —OH | 5', —SO₂NH₂ |
| 126 | —CH₂C(O)NH₂ | 2', —OH | 5', —SO₂NH₂ |
| 127 | —CH₂C(O)N(CH₃)₂ | 2', —OH | 5', —SO₂NH₂ |
| 128 | —CH₂C(O)NHCH(CH₂OH)₂ | 2', —OH | 5', —SO₂NH₂ |
| 129 | —CH₂C(O)NHCH₂COOH | 2', —OH | 5', —SO₂NH₂ |
| 130 | —CH₂C(O)NHCH₂CONH₂ | 2', —OH | 5', —SO₂NH₂ |
| 131 | —CH₂C(O)NHCH₂CH₂N(CH₃)₂ | 2', —OH | 5', —SO₂NH₂ |
| 132 | —CH₂C(O)NHCH₂CH₂CH₂N(CH₃)₂ | 2', —OH | 5', —SO₂NH₂ |
| 133 | —CH₂C(O)NHCH₂CH₂COOH | 2', —OH | 5', —SO₂NH₂ |
| 134 | (structure: CH₃NH-CH₂CH₂-O-CH₂CH₂-O-CH₂CH₂-N(CH₃)-C(O)-CH₂•) | 2', —OH | 5', —SO₂NH₂ |
| 135 | (structure: •CH₂-C(O)NH-CH₂-sugar (hexose with 4 OH)) | 2', —OH | 5', —SO₂NH₂ |

TABLE I-continued

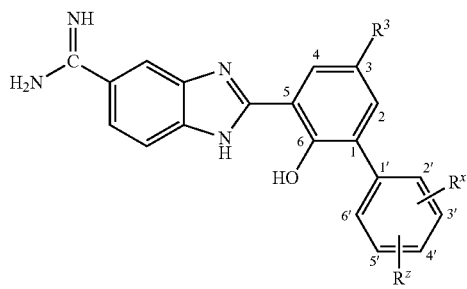

| Cpd. # | R³ | Position, Rx | Position, Rz |
|---|---|---|---|
| 136 | (2-acetamido-glucopyranose structure with OH, OH, HO, HO, NH, C(O)CH₂·) | 2', —OH | 5', —SO₂NH₂ |
| 137 | (N-methyl-N-acyl polyhydroxy chain: HO, HO, HO, OH, OH, N(CH₃)C(O)CH₂·) | 2', —OH | 5', —SO₂NH₂ |
| 138 | (tris(hydroxymethyl)methyl acetamide: HO, HO, OH, HN—C(O)CH₂·) | 2', —OH | 5', —SO₂NH₂ |
| 139 | —CH₂C(O)NHCH₃ | 2', —OH | 5', —SO₂NH₂ |
| 140 | (asparaginamide derivative: H₂N—C(O), C(O)NH₂, HN—C(O)CH₂·) | 2', —OH | 5', —SO₂NH₂ |
| 141 | ·CH₂—C(O)NH—CH₂—C(O)NH-(glucopyranose with OH, OH, OH, HO, CH₂OH) | 2', —OH | 5', —SO₂NH₂ |
| 142 | CH₃CH₂—O—CH₂CH₂—O—CH₂CH₂—O—CH₂CH₂CH₂—NH—C(O)CH₂· | 2', —OH | 5', —SO₂NH₂ |

TABLE I-continued

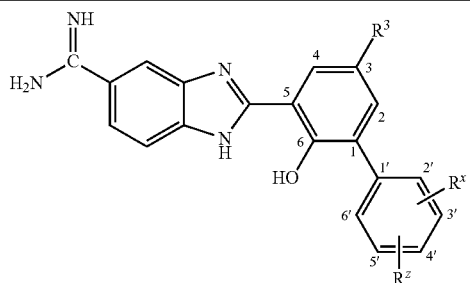

| Cpd. # | R³ | Position, Rx | Position, Rz |
|---|---|---|---|
| 143 | (HO)(PH)P(O)CH₂CH₂NHC(O)CH₂• | 2', —OH | 5', —SO₂NH₂ |
| 144 | [(HO)₂P(O)CH₂CH₂]₂NC(O)CH₂• | 2', —OH | 5', —SO₂NH₂ |
| 145 | H₂NC(O)CH₂CH(COOH)NHC(O)C(CH₃)₂• | 2', —OH | 5', —SO₂NH₂ |
| 146 | —C(CH₃)₂C(O)N(CH₂COOH)₂ | 2', —OH | 5', —SO₂NH₂ |
| 147 | —C(CH₃)₂C(O)NHCH(COOH)CH₂COOH | 2', —OH | 5', —SO₂NH₂ |
| 148 | prolinamide-C(O)C(CH₃)₂• | 2', —OH | 5', —SO₂NH₂ |
| 149 | 4-hydroxyproline-N—C(O)C(CH₃)₂• | 2', —OH | 5', —SO₂NH₂ |
| 150 | —C(CH₃)₂C(O)NH₂ | 2', —OH | 5', —SO₂NH₂ |
| 151 | —C(CH₃)₂C(O)N(CH₃)₂ | 2', —OH | 5', —SO₂NH₂ |
| 152 | —C(CH₃)₂C(O)NHCH(CH₂OH)₂ | 2', —OH | 5', —SO₂NH₂ |
| 153 | —C(CH₃)₂C(O)NHCH₂COOH | 2', —OH | 5', —SO₂NH₂ |
| 154 | —C(CH₃)₂C(O)NHCH₂CONH₂ | 2', —OH | 5', —SO₂NH₂ |
| 155 | —C(CH₃)₂C(O)NHCH₂CH₂N(CH₃)₂ | 2', —OH | 5', —SO₂NH₂ |
| 156 | —C(CH₃)₂C(O)NHCH₂CH₂CH₂N(CH₃)₂ | 2', —OH | 5', —SO₂NH₂ |
| 157 | —C(CH₃)₂C(O)NHCH₂CH₂COOH | 2', —OH | 5', —SO₂NH₂ |
| 158 | (CH₃)₂C(•)C(O)N(CH₃)CH₂CH₂OCH₂CH₂OCH₂CH₂NH(CH₃) | 2', —OH | 5', —SO₂NH₂ |

TABLE I-continued

| Cpd. # | R³ | Position, Rx | Position, Rz |
|---|---|---|---|
| 159 | (glucosamide-CH₂ linked carbonyl isopropyl) | 2', —OH | 5', —SO₂NH₂ |
| 160 | (glucosamine N-linked carbonyl isopropyl) | 2', —OH | 5', —SO₂NH₂ |
| 161 | (N-methyl-N-(polyhydroxyhexyl) carboxamide isopropyl) | 2', —OH | 5', —SO₂NH₂ |
| 162 | (tris(hydroxymethyl)methyl carboxamide isopropyl) | 2', —OH | 5', —SO₂NH₂ |
| 163 | —C(CH₃)₂C(O)NHCH₃ | 2', —OH | 5', —SO₂NH₂ |
| 164 | (asparaginamide N-linked carboxamide isopropyl) | 2', —OH | 5', —SO₂NH₂ |
| 165 | (glucosamine N-linked carboxamide isopropyl) | 2', —OH | 5', —SO₂NH₂ |

TABLE I-continued

Structure (parent):

Benzimidazole with 6-position carboxamidine (H₂N-C(=NH)-), 2-position connected to phenyl ring with positions labeled 1-6 (6-OH, 5-R³), and the phenyl at position 1 connected to another phenyl ring (positions 1'-6') bearing Rx and Rz substituents.

| Cpd. # | R³ | Position, Rx | Position, Rz |
|---|---|---|---|
| 166 | —C(CH₃)₂C(O)NH-CH₂CH₂CH₂-O-CH₂CH₂-O-CH₂CH₂-O-CH₂CH₃ | 2', —OH | 5', —SO₂NH₂ |
| 167 | —C(CH₃)₂C(O)NH-CH₂-P(O)(OH)₂ | 2', —OH | 5', —SO₂NH₂ |
| 168 | —C(CH₃)₂C(O)N[CH₂CH₂P(O)(OH)₂]₂ | 2', —OH | 5', —SO₂NH₂ |
| 169 | —C(CH₃)₂C(O)NH-CH(COOH)-CH₂-C(O)NH₂ (asparagine-like) | 2', —OH | 5', —CH₂NHC(O)NH₂ |
| 170 | —C(CH₃)₂C(O)N(CH₂COOH)₂ | 2', —OH | 5', —CH₂NHC(O)NH₂ |
| 171 | —C(CH₃)₂C(O)NHCH(COOH)CH₂COOH | 2', —OH | 5', —CH₂NHC(O)NH₂ |
| 172 | —C(CH₃)₂C(O)-[prolinamide] (1-acyl pyrrolidine-2-carboxamide) | 2', —OH | 5', —CH₂NHC(O)NH₂ |
| 173 | —C(CH₃)₂C(O)-[4-hydroxyproline] (1-acyl-4-hydroxypyrrolidine-2-carboxylic acid) | 2', —OH | 5', —CH₂NHC(O)NH₂ |
| 174 | —C(CH₃)₂C(O)NH₂ | 2', —OH | 5', —CH₂NHC(O)NH₂ |
| 175 | —C(CH₃)₂C(O)N(CH₃)₂ | 2', —OH | 5', —CH₂NHC(O)NH₂ |
| 176 | —C(CH₃)₂C(O)NHCH(CH₂OH)₂ | 2', —OH | 5', —CH₂NHC(O)NH₂ |
| 177 | —C(CH₃)₂C(O)NHCH₂COOH | 2', —OH | 5', —CH₂NHC(O)NH₂ |
| 178 | —C(CH₃)₂C(O)NHCH₂CONH₂ | 2', —OH | 5', —CH₂NHC(O)NH₂ |
| 179 | —C(CH₃)₂C(O)NHCH₂CH₂N(CH₃)₂ | 2', —OH | 5', —CH₂NHC(O)NH₂ |

TABLE I-continued

| Cpd. # | R³ | Position, Rx | Position, Rz |
|---|---|---|---|
| 180 | —C(CH₃)₂C(O)NHCH₂CH₂CH₂N(CH₃)₂ | 2', —OH | 5', —CH₂NHC(O)NH₂ |
| 181 | —C(CH₃)₂C(O)NHCH₂CH₂COOH | 2', —OH | 5', —CH₂NHC(O)NH₂ |
| 182 | [structure] | 2', —OH | 5', —CH₂NHC(O)NH₂ |
| 183 | [structure] | 2', —OH | 5', —CH₂NHC(O)NH₂ |
| 184 | [structure] | 2', —OH | 5', —CH₂NHC(O)NH₂ |
| 185 | [structure] | 2', —OH | 5', —CH₂NHC(O)NH₂ |
| 186 | [structure] | 2', —OH | 5', —CH₂NHC(O)NH₂ |
| 187 | —C(CH₃)₂C(O)NHCH₃ | 2', —OH | 5', —CH₂NHC(O)NH₂ |
| 188 | [structure] | 2', —OH | 5', —CH₂NHC(O)NH₂ |

TABLE I-continued
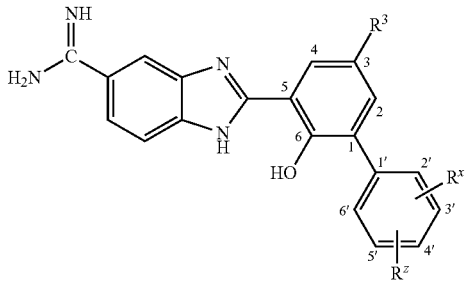
| Cpd. # | R³ | Position, Rx | Position, Rz |
|---|---|---|---|
| 189 | 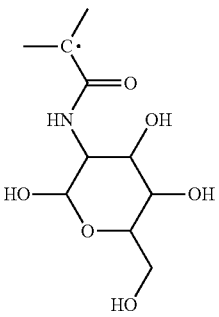 | 2', —OH | 5', —CH₂NHC(O)NH₂ |
| 190 | 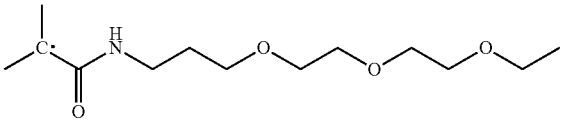 | 2', —OH | 5', —CH₂NHC(O)NH₂ |
| 191 | 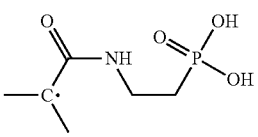 | 2', —OH | 5', —CH₂NHC(O)NH₂ |
| 192 | 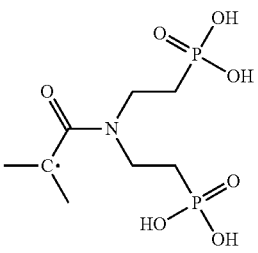 | 2', —OH | 5', —CH₂NHC(O)NH₂ |
| 193 | 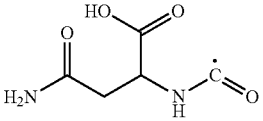 | 2', —OH | 5', —SO₂NH₂ |
| 194 | —C(O)N(CH₂COOH)₂ | 2', —OH | 5', —SO₂NH₂ |
| 195 | 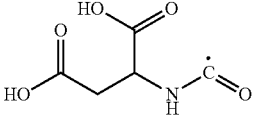 | 2', —OH | 5', —SO₂NH₂ |

TABLE I-continued
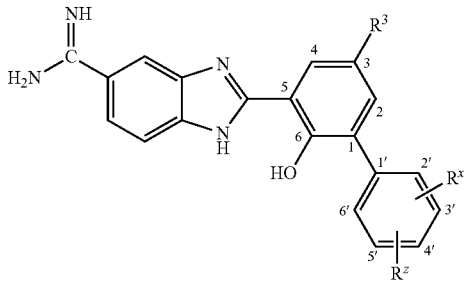
| Cpd. # | R³ | Position, Rx | Position, Rz |
|---|---|---|---|
| 196 | 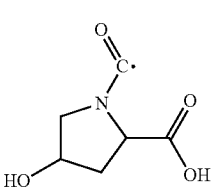 | 2', —OH | 5', —SO₂NH₂ |
| 197 | 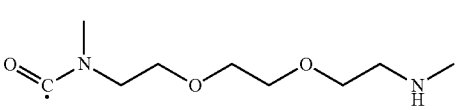 | 2', —OH | 5', —SO₂NH₂ |
| 198 | —C(O)NH₂ | 2', —OH | 5', —SO₂NH₂ |
| 199 | —C(O)N(CH₃)₂ | 2', —OH | 5', —SO₂NH₂ |
| 200 | —C(O)NHCH(CH₂OH)₂ | 2', —OH | 5', —SO₂NH₂ |
| 201 | —C(O)NHCH₂COOH | 2', —OH | 5', —SO₂NH₂ |
| 202 | —C(O)NHCH₂CONH₂ | 2', —OH | 5', —SO₂NH₂ |
| 203 | —C(O)NHCH₂CH₂N(CH₃)₂ | 2', —OH | 5', —SO₂NH₂ |
| 204 | —C(O)NHCH₂CH₂CH₂N(CH₃)₂ | 2', —OH | 5', —SO₂NH₂ |
| 205 | —C(O)NHCH₂CH₂COOH | 2', —OH | 5', —SO₂NH₂ |
| 206 | 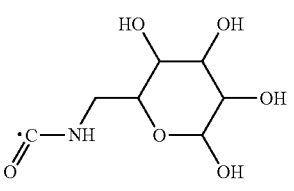 | 2', —OH | 5', —SO₂NH₂ |
| 207 | 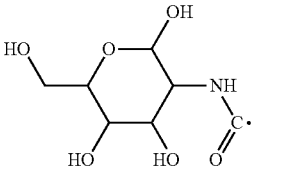 | 2', —OH | 5', —SO₂NH₂ |
| 208 | 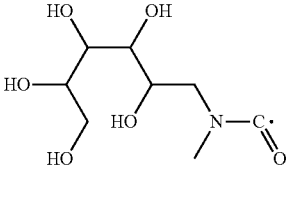 | 2', —OH | 5', —SO₂NH₂ |
| 209 |  | 2', —OH | 5', —SO₂NH₂ |

TABLE I-continued

| Cpd. # | R³ | Position, Rx | Position, Rz |
|---|---|---|---|
| 210 | (C(O)NH-C(CH₂OH)₃) | 2', —OH | 5', —SO₂NH₂ |
| 211 | —C(O)NHCH₃ | 2', —OH | 5', —SO₂NH₂ |
| 212 | (C(O)NH-CH(C(O)NH₂)-CH₂C(O)NH₂, asparagine-like) | 2', —OH | 5', —SO₂NH₂ |
| 213 | (C(O)NH-CH₂-C(O)NH-glucosamine) | 2', —OH | 5', —SO₂NH₂ |
| 214 | (C(O)NH-CH₂CH₂CH₂-O-CH₂CH₂-O-CH₂CH₂-O-CH₂CH₃) | 2', —OH | 5', —SO₂NH₂ |
| 215 | (C(O)NH-CH₂CH₂-P(O)(OH)₂) | 2', —OH | 5', —SO₂NH₂ |
| 216 | (C(O)-N(CH₂CH₂P(O)(OH)₂)₂) | 2', —OH | 5', —SO₂NH₂ |
| 217 | —C(O)N(CH₂CH₂OH) | 2', —OH | 5', —SO₂NH₂ |
| 218 | —C(O)NHCH₂CH₂N⁺(CH₃)₃ | 2', —OH | 5', —SO₂NH₂ |
| 219 | (C(O)-piperazine-CH₂CH₂NH₂) | 2', —OH | 5', —SO₂NH₂ |
| 220 | —C(O)NHCH₂CH₂CH₂CH₂CH(NH₂)COOH | 2', —OH | 5', —SO₂NH₂ |
| 221 | —C(O)NHOH | 2', —OH | 5', —SO₂NH₂ |
| 222 | —C(O)N(CH₃)₂ | 2', —OH | 5', —SO₂NH₂ |
| 223 | —C(O)NH₂ | 2', —OH | 5', —SO₂NH₂ |

TABLE I-continued

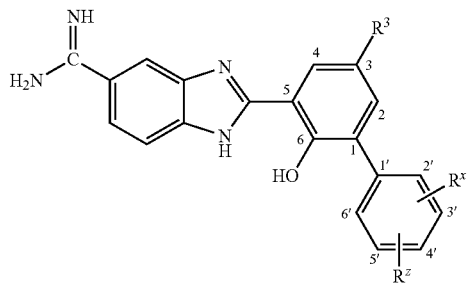

| Cpd. # | R³ | Position, Rx | Position, Rz |
|---|---|---|---|
| 224 | (pyrrolidine-1-carbonyl with 2-carboxamide) | 2', —OH | 5', —SO₂NH₂ |
| 225 | (morpholine-4-carbonyl) | 2', —OH | 5', —SO₂NH₂ |
| 226 | (pyrrolidine-1-carbonyl with 2-carboxylic acid) | 2', —OH | 5', —SO₂NH₂ |
| 228 | (tetramethylguanidinium-ethyl-piperazine carbonyl) | 2', —OH | 5', —SO₂NH₂ |
| 229 | —C(O)NHCH₃ | 2', —OH | 5', —SO₂NH₂ |
| 230 | (N-(2-hydroxy-3-morpholinopropyl)carbamoyl) | 2', —OH | 5', —SO₂NH₂ |
| 231 | (4-carbamoylpiperidine-1-carbonyl) | 2', —OH | 5', —SO₂NH₂ |
| 232 | (3-carbamoylpiperidine-1-carbonyl) | 2', —OH | 5', —SO₂NH₂ |
| 233 | (N-glucamine carbonyl) | 2', —OH | 5', —SO₂NH₂ |
| 234 | —CH₂C(O)NHCH₂CH₂S(O)₂OH | 2', —OH | 5', —SO₂NH₂ |

TABLE I-continued

| Cpd. # | R³ | Position, Rx | Position, Rz |
|---|---|---|---|
| 235 | (CH₂-NH-C(O)-CH₂-N-morpholine) | 2', —OH | 5', —SO₂NH₂ |
| 236 | —CH₃ | H | 4', —OH |
| 237 | (cyclopentane with C(O), CO₂H, OH substituents) | 2', —OH | 5', —F |
| 238 | —C(CH₃)₂C(O)NH₂ | 2', —OH | 5', —CH₂NHC(O)NH₂ |

Representative compounds of Formula I where $R^1$, $R^2$ and $R^y$ are hydrogen; $X^2$ is —N—, $X^1$, $X^3$, and $X^4$ are carbon are disclosed in Table II below.

TABLE II

| Cpd. # | R³ | Position, Rx | Position, Rz |
|---|---|---|---|
| 239 | —H | 2', —OH | 5', CONH₂ |
| 240 | —H | 2', —OH | 5', —NHCONH₂ |

The compounds of Formula I and the intermediates and starting materials used in their preparation are named generally by AutoNom 4.0 (Beilstein Information Systems, Inc.).

Preferred Embodiments

While the broadest definition of this invention is set forth in the Summary of the Invention, certain compounds of Formula I are preferred. For example:

(I) One preferred group of compounds is represented by the Formula Ia:

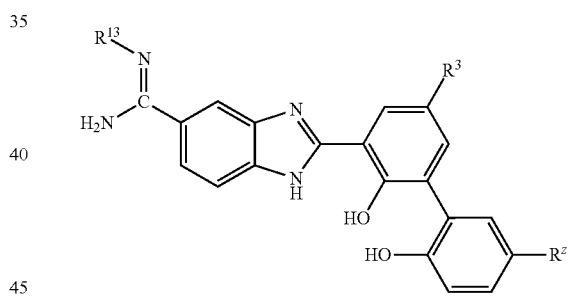

Ia wherein:

$R^3$ is hydrogen, halo, alkyl, alkoxy, haloalkyl, haloalkoxy, cyanoalkyl, tetrazol-5-yl, tetrazol-5-ylalkyl, hydroxyalkylcarbonyl, aminosulfonyl, alkylaminosulfonyl, dialkylaminosulfonyl, —NHSO₂R (where R is alkyl, aryl, aralkyl, heteroaryl, heteroaralkyl, cycloalkyl, cycloalkylalkyl, heterocycloalkyl or heterocycloalkylalkyl), —SO₂NHCOR⁶ (where $R^6$ is alkyl, aryl, aralkyl, heteroaryl, heteroaralkyl, heterocycloalkyl, or heterocycloalkylalkyl), —CONR⁷R⁸ or —COCONR⁷R⁸ (where $R^7$ is hydrogen, alkyl, alkoxyalkyl, carboxyalkyl, hydroxyalkyl or phosphonoalkyl and $R^8$ is hydrogen, alkyl, alkoxyalkyl, -(alkylene)-(OCH₂CH₂)ₙ $R^b$ (where n is an integer from 1 to 6 and $R^b$ is hydrogen, alkyl, hydroxy, alkoxy, amino or alkylcarbonylamino), aminoalkyl, aminocarbonylalkyl, aminocarbonylcarboxyalkyl, aminocarboxyalkyl, carboxyalkyl, hydroxyalkyl, phosphonoalkyl, sulfoalkyl, trimethylammonioalkyl, aryl, aralkyl, heteroaryl, heteroaralkyl or hetereocycloalkylalkyl or $R^7$ and $R^8$ together with the nitrogen atom to which they are attached form heterocycloalkylamino), -(alkylene)-CONR⁹R¹⁰ (where $R^9$ is hydrogen, alkyl, alkoxyalkyl, carboxyalkyl, hydroxyalkyl or phosphonoalkyl and $R^{10}$ is hydrogen, alkyl, alkoxyalkyl, -(alkylene)-(OCH$_2$CH$_2$)$_n$ R$^b$ (where n is an integer from 1 to 6 and R$^b$ is hydrogen, alkyl, hydroxy, alkoxy, amino or alkylcarbonylamino), aminoalkyl, aminocarbonylalkyl, aminocarbonylcarboxyalkyl, aminocarboxyalkyl, carboxyalkyl, hydroxyalkyl, phosphonoalkyl, sulfoalkyl, trimethylammonioalkyl, aryl, aralkyl, heteroaryl, heteroaralkyl, or heterocycloalkylalkyl or R$^9$ and R$^{10}$ together with the nitrogen atom to which they are attached form heterocycloalkylamino), —CONHSO$_2$R$^{11}$ (where R$^{11}$ is alkyl, aryl, aralkyl, heteroaryl, heteroaralkyl, heterocyclalkyl, or heterocycloalkylalkyl), or -(alkylene)-CONHSO$_2$R$^{11}$ (where R$^{11}$ is alkyl, aryl, aralkyl, heteroaryl, heteroaralkyl, heterocycloalkyl, or heterocycloalkylalkyl), wherein any rings comprising R$^3$ are optionally substituted with one to six groups independently selected from hydroxy, hydroxyalkyl, alkoxyalkyl, carboxy, alkoxycarbonyl, aminoalkyl, guanidinoalkyl, alkyl or —CONR$^a$R$^b$ where R$^a$ and R$^b$ are independently hydrogen or alkyl; and R$^z$ is hydrogen, alkyl, haloalkyl, cycloalkyl, alkylthio, halo, hydroxy, hydroxyalkyl, nitro, cyano, alkoxy, alkoxyalkyl, alkoxyalkyloxy, hydroxyalkyloxy, aminoalkyloxy, carboxyalkyloxy, aminocarbonylalkyloxy, haloalkoxy, carboxy, carboxyalkyl, alkoxycarbonyl, alkoxycarbonylalkyl, cyanoalkyl, alkylsulfonyl, alkylsulfonylalkyl, arylsulfonyl, heteroarylsulfonyl, carbamimidoyl, hydroxycarbamimidoyl, alkoxycarbamimidoyl, alkylsulfonylamino, alkylsulfonylaminoalkyl, alkoxysulfonylamino, alkoxysulfonylaminoalkyl, heterocycloalkylalkylaminocarbonyl, hydroxyalkoxyalkylaminocarbonyl, heterocycloalkylcarbonyl, heterocycloalkylcarbonylalkyl, heterocycloalkyl, heterocycloalkylalkyl, oxoheterocycloalkyl, oxoheterocycloalkylalkyl, heteroaryl, heteroaralkyl, ureido, alkylureido, dialkylureido, ureidoalkyl, alkylureidoalkyl, dialkylureidoalkyl, thioureido, thioureidoalkyl, —COR$^{12}$ (where R$^{12}$ is alkyl, haloalkyl, hydroxyalkyl, alkoxyalkyl, or aminoalkyl), -(alkylene)-COR$^{12}$ (where R$^{12}$ is alkyl, haloalkyl, hydroxyalkyl, alkoxyalkyl, or aminoalkyl), —CONR$^{14}$R$^{15}$ (where R$^{14}$ is hydrogen or alkyl and R$^{15}$ is hydrogen, alkyl, hydroxyalkyl, alkoxyalkyl, aryl, aralkyl, heteroaryl or heteroaralkyl or R$^{14}$ and R$^{15}$ together with the nitrogen atom to which they are attached from heterocycloamino), -(alkylene)-CONR$^{16}$R$^{17}$ (where R$^{16}$ is hydrogen, alkyl or hydroxyalkyl and R$^{17}$ is hydrogen, alkyl, hydroxyalkyl, alkoxyalkyl, aryl, aralkyl, heteroaryl or heteroaralkyl or R$^{14}$ and R$^{15}$ together with the nitrogen atom to which they are attached from heterocycloamino), —NR$^{18}$R$^{19}$ (where R$^{18}$ is hydrogen or alkyl and R$^{19}$ is hydrogen, alkyl, acyl, aryl, aralkyl, heteroaryl, or heteroaralkyl), -(alkylene)-NR$^{20}$R$^{21}$ (where R$^{20}$ is hydrogen, alkyl, or hydroxyalkyl and R$^{21}$ is hydrogen, alkyl, acyl, alkoxycarbonyl, hydroxyalkyl, alkoxyalkyl, aryl, aralkyl, heteroaryl or heteroaralkyl), —SO$_2$NR$^{22}$R$^{23}$ (where R$^{22}$ is hydrogen or alkyl and R$^{23}$ is hydrogen, alkyl, aryl, aralkyl, heteroaryl or heteroaralkyl or R$^{22}$ and R$^{23}$ together with the nitrogen atom to which they are attached from heterocycloamino), -(alkylene)-SO$_2$NR$^{24}$R$^{25}$ (where R$^{24}$ is hydrogen or alkyl and R$^{25}$ is hydrogen, alkyl, aryl, aralkyl, heteroaryl or heteroaralkyl or R$^{24}$ and R$^{25}$ together with the nitrogen atom to which they are attached from heterocycloamino), —NR$^{26}$SO$_2$NR$^{27}$R$^{28}$ (where R$^{26}$ and R$^{27}$ are independently hydrogen or alkyl, and R$^{28}$ is hydrogen, alkyl, aryl, aralkyl, heteroaryl or heteroaralkyl or R$^{27}$ and R$^{28}$ together with the nitrogen atom to which they are attached from heterocycloamino), -(alkylene)-NR$^{29}$SO$_2$NR$^{30}$R$^{31}$ (where R$^{29}$ and R$^{30}$ are independently hydrogen or alkyl, and R$^{31}$ is hydrogen, alkyl, aryl, aralkyl, heteroaryl or heteroaralkyl or R$^{30}$ and R$^{31}$ together with the nitrogen atom to which they are attached from heterocycloamino), —CONH-(alkylene)-NR$^{32}$R$^{33}$ where R$^{32}$ is hydrogen or alkyl and R$^{33}$ is alkyl), or aralkyl; and R$^{13}$ is hydrogen, hydroxy, (C$_{1\text{-}10}$)alkoxy, —C(O)R$^{35}$ where R$^{35}$ is alkyl, aryl, haloalkyl, or cyanoalkyl, or —C(O) OR$^{36}$ where R$^{36}$ is alkyl, hydroxyalkyl, acyl, or haloalkyl; or a pharmaceutically acceptable salt thereof.

(a) Within the above group Ia, a more preferred group of compounds is that wherein R$^3$ is hydrogen.

(b) Within the above group Ia, another more preferred group of compounds is that wherein R$^3$ is halo, preferably chloro or fluoro, more preferably fluoro.

(c) Within the above group Ia, another more preferred group of compounds is that wherein R$^3$ is —SO$_2$NHCOR$^6$ where R$^6$ is as defined in its broadest terms in the Summary of the Invention. Preferably R$^6$ is alkyl, aralkyl, aryl, heteroaralkyl or heterocycloalkylalkyl. More preferably R$^3$ is aminosulfonyl, acetylaminosulfonyl, 2-phenyethylcarbonyl-aminosulfonyl, phenylcarbonylaminosulfonyl, 3-phenylpropylcarbonylaminosulfonyl, benzylcarbonylaminosulfonyl, 2-(3,4-dichlorophenyl)ethylcarbonylaminosulfonyl, 2-pyridin-3-ylethylcarbonylaminosulfonyl, 2-piperidin-3-ylethylcarbonylaminosulfonyl. Even more preferably R$^3$ is acetylaminosulfonyl.

(d) Within the above group Ia, yet another more preferred group of compounds is that wherein R$^3$ is —CONR$^7$R$^8$ (where R$^7$ is hydrogen, alkyl, hydroxyalkyl, or alkoxyalkyl and R$^8$ is hydrogen, alkyl, hydroxyalkyl, alkoxyalkyl, aminoalkyl, aryl, aralkyl, heteroaryl, heteroaralkyl, or hetereocycloalkylalkyl or R$^7$ and R$^8$ together with the nitrogen atom to which they are attached form heterocycloalkylamino), wherein any rings comprising R$^3$ are optionally substituted with one or two groups independently selected from hydroxy, hydroxyalkyl, carboxy, alkoxycarbonyl, alkyl, or —CONR$^a$R$^b$ where R$^a$ and R$^b$ are independently hydrogen or alkyl. Preferably R$^7$ is hydrogen or alkyl, and R$^8$ is hydrogen, alkyl, aralkyl, or heteroaralkyl, or R$^7$ and R$^8$ together with the nitrogen atom to which they are attached form heterocycloalkylamino optionally substituted with one or two groups independently selected from hydroxy, hydroxyalkyl, carboxy, alkoxycarbonyl, alkyl, or —CONR$^a$R$^b$ where R$^a$ and R$^b$ are independently hydrogen or alkyl. More preferably, R$^7$ and R$^8$ together with the nitrogen atom to which they are attached form optionally substituted heterocycloalkylamino. Even more preferably, R$^3$ is aminocarbonyl, dimethylaminocarbonyl, 2-morpholin-4-ylethylaminocarbonyl, 2-phenethylaminocarbonyl, methylaminocarbonyl, pyridin-2-ylmethylaminocarbonyl, furan-2-ylmethylaminocarbonyl, 2-pyridin-4-ylethylaminocarbonyl, 2-pyridin-3-ylethylaminocarbonyl, 2-pyridin-2-ylethylaminocarbonyl, pyridin-4-ylmethylamino-carbonyl, pyrrolidin-1-ylcarbonyl, piperidin-1-ylcarbonyl, morpholin-4-ylcarbonyl, piperazin-1-ylcarbonyl or thiazolidin-1-ylcarbonyl wherein any rings comprising R$^3$ are optionally substituted with one or two groups independently selected from hydroxy, hydroxyalkyl, carboxy, alkoxycarbonyl, alkyl, or —CONR$^a$R$^b$ where R$^a$ and R$^b$ are independently hydrogen or alkyl. Particularly, R$^3$ is 4-hydroxypiperidin-1-ylcarbonyl, piperidin-1-ylcarbonyl, 2-methoxycarbonylpyrrolidin-1-ylcarbonyl, 4-methylpiperazin-1-ylcarbonyl, pyrrolidin-1-ylcarbonyl, morpholin-4-ylcarbonyl, (2R) or (2S)-aminocarbonylpyrrolidin-1-ylcarbonyl, (2R) or (2S)-carboxypyrrolidin-1-ylcarbonyl, (2R) or (2S)-methoxycarbonyl, pyrrolidin-1-ylcarbonyl, dimethylaminocarbonyl, 3RS-aminocarbonylpiperidin-1-ylcarbonyl, 2S-methoxycarbonyl-4R-hydroxypyrrolidin-1-ylcarbonyl, (2R) or (2S)-dimethylaminocarbonylpyrrolidin-1- ylcarbonyl, 2-(S)-hydroxymethylpyrrolidin-1-ylcarbonyl, 3R-hydroxypyrrolidin-1-ylcarbonyl, 2S-methoxycarbonyl-4S-hydroxypyrrolidin-1-ylcarbonyl, 2S-carboxy-4R-hydroxypyrrolidin-1-ylcarbonyl, 2S-aminocarbonyl-4R-hydroxypyrrolidin-1-ylcarbonyl, 2S-carboxy-4S-hydroxypyrrolidin-1-ylcarbonyl, 2R-methoxycarbonyl-4R-hydroxypyrrolidin-1-ylcarbonyl or 2R-carboxy-4R-hydroxypyrrolidin-1-ylcarbonyl.

(e) Within the above group Ia, yet another more preferred group of compounds is that wherein $R^3$ is -(alkylene)-$CONR^9R^{10}$ (where $R^9$ is hydrogen, alkyl, hydroxyalkyl, alkoxyalkyl and $R^{10}$ is hydrogen, alkyl, hydroxyalkyl, alkoxyalkyl, aminoalkyl, aryl, aralkyl, heteroaryl, heteroaralkyl, or heterocycloalkylalkyl, or $R^9$ and $R^{10}$ together with the nitrogen atom to which they are attached form heterocycloalkylamino), wherein any rings comprising $R^3$ are optionally substituted with one or two groups independently selected from hydroxy, hydroxyalkyl, carboxy, alkoxycarbonyl, alkyl, or —$CONR^aR^b$ where $R^a$ and $R^b$ are independently hydrogen or alkyl.

(f) Within the above group Ia, yet another more preferred group of compounds is that wherein $R^3$ is haloalkyl or haloalkoxy, preferably trifluoromethyl or trifluoromethoxy.

(g) Within the above group Ia, yet another more preferred group of compounds is that wherein $R^3$ is alkyl or alkoxy, preferably methyl or methoxy.

(h) Within the above group Ia, yet another more preferred group of compounds is that wherein $R^3$ is tetrazol-5-y or tetrazol-5-ylmethyl.

(i) Within the above group Ia, another more preferred group of compounds is that wherein $R^3$ is aminosulfonyl or dimethylaminosulfonyl, preferably aminosulfonyl.

(j) Within the above group Ia, another more preferred group of compounds is that wherein $R^3$ is halo, —$CONR^7R^8$ (where $R^7$ is hydrogen or alkyl and $R^8$ is aminocarbonylalkyl or hetereocycloalkylalkyl or $R^7$ and $R^8$ together with the nitrogen atom to which they are attached form heterocycloalkylamino) or -(alkylene)-$CONR^9R^{10}$ (where $R^9$ is hydrogen or alkyl and $R^{10}$ is sulfoalkyl, carboxyaminoalkyl, ammonioalkyl, or heterocycloalkylalkyl, or $R^9$ and $R^{10}$ together with the nitrogen atom to which they are attached form heterocycloalkylamino), wherein any rings comprising $R^3$ are optionally substituted with one or two groups independently selected from hydroxy, hydroxyalkyl, carboxy, alkoxycarbonyl, alkyl or —$CONR^aR^b$ where $R^a$ and $R^b$ are independently hydrogen or alkyl. Preferably $R^3$ is fluoro, 2-morpholin-4-ylethylaminocarbonylmethyl, 2-sulfoethylaminocarbonylmethyl, 5-amino-5-carboxypentylaminocarbonylmethyl, 4-methylpiperazin-1-ylcarbonylmethyl, 2-ammonioethylaminocarbonylmethyl, aminocarbonyl.

(k) Within the above group Ia, another preferred group of compounds is that wherein $R^3$ is —$CONR^7R^8$, —$CH_2CONR^9R^{10}$ or —$C(CH_3)_2CONR^9R^{10}$ wherein $R^7$ and $R^8$ or $R^9$ and $R^{10}$ both are hydrogen, carboxymethyl, 2-hydroxyethyl or 2-phosphonoethyl or $R^7$ or $R^9$ is hydrogen or methyl and $R^8$ or $R^{10}$, respectively, is aminocarbonylmethyl, 1,2-aminocarbonylethyl, 2-aminocarbonyl-1-carboxyethyl, preferably 2S-aminocarbonyl-1-carboxyethyl, 5-amino-5-carboxypentyl, preferably 5S-amino-5-carboxypentyl, 2-carboxyethyl, carboxymethyl, 2-carboxy-3-[2-(2-ethoxy-ethoxy)-ethoxy]-propyl, dimethylaminomethyl, 3-dimethylaminopropyl, 2-hydroxy-1,1-bis-hydroxymethyl-ethyl, 2-hydroxy-1-hydroxymethylethyl, 1,2-dicarboxyethyl, preferably 1R,2-dicarboxyethyl, methyl, 2-[2-(2-methylaminoethoxy]ethoxy]ethyl, 2-(4-methylpiperazin-1-yl)ethyl, 2-morpholin-4-ylethyl, 2,3,4,5,6-pentahydroxy-hexyl, preferably 2R,3R,4R,5S,6-pentahydroxy-hexyl, 2-piperazin-1-ylethyl, 2-sulfoethyl, 3,4,5,6-tetrahydroxy-tetrahydro-pyran-2-ylmethyl, preferably 3S,4S,5R,6S-tetrahydroxy-tetrahydro-pyran-2R-ylmethyl, 2,4,5-trihydroxy-6-hydroxymethyl-tetrahydro-pyran-3-yl, preferably 2,4R,5S-trihydroxy-6R-hydroxymethyl-tetrahydro-pyran-3-yl, 2,4,5-trihydroxy-6-hydroxymethyl-tetrahydro-pyran-3-ylcarbamoyl-methyl, preferably 2,4R,5S-trihydroxy-6R-hydroxymethyl-tetrahydro-pyran-3-ylcarbamoyl-methyl, trimethylammonioethyl or 2-phosphonoethyl or $R^7$ and $R^8$ or $R^9$ and $R^{10}$ together with the nitrogen atom to which they are attached form 2-aminocarbonylpyrrolidin-1-yl, preferably 2R-aminocarbonylpyrrolidin-1-yl, 2-carboxy-4-hydroxypyrrolidin-1-yl, preferably 2S-carboxy-4-hydroxypyrrolidin-1-yl, or 4-methylpiperazin-1-yl.

Within the above preferred and more preferred groups (a-j), a particularly preferred group of compounds is that wherein:

$R^z$ is halo, hydroxyalkyl, alkylsulfonylamino, alkylsulfonylaminoalkyl, aminosulfonyl, heterocycloalkylcarbonylalkyl, oxoheterocycloalkyl, carboxyalkyl, oxoheterocycloalkylalkyl, heteroaralkyl, ureido, alkylureido, dialkylureido, ureidoalkyl, alkylureidoalkyl, dialkylureidoalkyl, thioureido, thioureidoalkyl, —$COR^{12}$ (where $R^{12}$ is alkyl, hydroxyalkyl, or haloalkyl), -(alkylene)-$COR^{12}$ (where $R^{12}$ is alkyl or haloalkyl), —$CONR^{14}R^{15}$ (where $R^{14}$ is hydrogen or alkyl and $R^{15}$ is hydrogen, alkyl, aryl, aralkyl, heteroaryl, or heteroaralkyl), -(alkylene)-$CONR^{16}R^{17}$ (where $R^{16}$ is hydrogen or alkyl and $R^{17}$ is hydrogen, alkyl, hydroxyalkyl, aryl, aralkyl, heteroaryl, or heteroaralkyl), —$NR^{18}R^{19}$ (where $R^{18}$ is hydrogen or alkyl and $R^{19}$ is hydrogen, alkyl, acyl, aryl, aralkyl, heteroaryl, or heteroaralkyl), -(alkylene)-$NR^{20}R^{21}$ (where $R^{20}$ is hydrogen or alkyl and $R^{21}$ is hydrogen, alkyl, acyl, aryl, aralkyl, heteroaryl, or heteroaralkyl), —$NR^{26}SO_2NR^{27}R^{28}$ (where $R^{26}$ and $R^{27}$ are independently hydrogen or alkyl, and $R^{28}$ is hydrogen, alkyl, aryl, aralkyl, heteroaryl, or heteroaralkyl or $R^{27}$ and $R^{28}$ together with the nitrogen atom to which they are attached form heterocycloamino), or -(alkylene)-$NR^{29}SO_2NR^{30}R^{31}$ (where $R^{29}$ and $R^{30}$ are independently hydrogen or alkyl, and $R^{31}$ is hydrogen, alkyl, aryl, aralkyl, heteroaryl, or heteroaralkyl or $R^{30}$ and $R^{31}$ together with the nitrogen atom to which they are attached from heterocycloamino).

Preferably, $R^z$ is aminosulfonyl, alkylsulfonylaminoalkyl, halo, carboxyalkyl, hydroxyalkyl, heterocycloalkylcarbonylalkyl, ureidoalkyl, alkylureidoalkyl, dialkylureidoalkyl, —$CONR^{14}R^{15}$ (where $R^{14}$ is hydrogen or alkyl and $R^{15}$ is hydrogen or alkyl), -(alkylene)-$CONR^{16}R^{17}$ (where $R^{16}$ is hydrogen or alkyl and $R^{17}$ is hydrogen, alkyl, or hydroxyalkyl), or -(alkylene)-$NR^{20}R^{21}$ (where $R^{20}$ is hydrogen or alkyl and $R^{21}$ is hydrogen, alkyl, hydroxyalkyl or acyl).

Preferably, $R^z$ is fluoro, aminosulfonyl, ureidomethyl, methylaminocarbonylmethyl, 2-tert-butylureidomethyl, 3,3-dimethylureidomethyl, aminomethyl, piperazin-1-ylcarbonylmethyl, carboxymethyl, hydroxymethylcarbonylaminomethyl, aminocarbonyl, acetylaminomethyl, aminocarbonylmethyl, methylaminocarbonylmethyl, dimethylaminocarbonylmethyl, 2-hydroxyethylaminocarbonylmethyl, morpholin-4-ylcarbonylmethyl, methoxycarbonylaminomethyl, hydroxymethyl, or methylsulfonylaminomethyl.

Within the above preferred, more preferred, and even more preferred groups, a particularly preferred group of compounds is that wherein:

$R^{13}$ is hydrogen, hydroxy, methoxy, or ethoxycarbonyl, more preferably hydrogen.

(II). Another preferred group of compounds is represented by the Formula Ib:

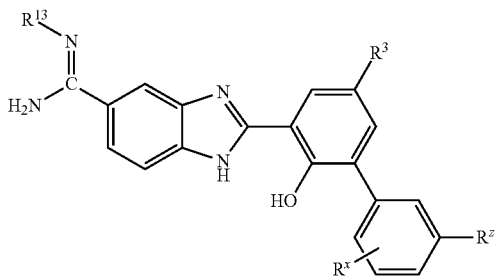

Ib wherein:

$R^3$ is hydrogen, halo, alkyl, alkoxy, haloalkyl, haloalkoxy, cyanoalkyl, tetrazol-5-yl, tetrazol-5-ylalkyl, hydroxyalkylcarbonyl, aminosulfonyl, alkylaminosulfonyl, dialkylaminosulfonyl, —NHSO$_2$R (where R is alkyl, aryl, aralkyl, heteroaryl, heteroaralkyl, cycloalkyl, cycloalkylalkyl, heterocycloalkyl or heterocycloalkylalkyl), —SO$_2$NHCOR$^6$ (where $R^6$ is alkyl, aryl, aralkyl, heteroaryl, heteroaralkyl, heterocycloalkyl, or heterocycloalkylalkyl), —CONR$^7$R$^8$ or —COCONR$^7$R$^8$ (where $R^7$ is hydrogen, alkyl, hydroxyalkyl, alkoxyalkyl and $R^8$ is hydrogen, alkyl, hydroxyalkyl, alkoxyalkyl, aminoalkyl, aryl, aralkyl, heteroaryl, heteroaralkyl, or hetereocycloalkylalkyl or $R^7$ and $R^8$ together with the nitrogen atom to which they are attached form heterocycloalkylamino), -(alkylene)-CONR$^9$R$^{10}$ (where $R^9$ is hydrogen, alkyl, hydroxyalkyl, alkoxyalkyl and $R^{10}$ is hydrogen, alkyl, hydroxyalkyl, alkoxyalkyl, aminoalkyl, aryl, aralkyl, heteroaryl, heteroaralkyl, or heterocycloalkylalkyl, or $R^9$ and $R^{10}$ together with the nitrogen atom to which they are attached form heterocycloalkylamino), —CONHSO$_2$R$^{11}$ (where $R^{11}$ is alkyl, aryl, aralkyl, heteroaryl, heteroaralkyl, heterocyclalkyl, or heterocycloalkylalkyl), or -(alkylene)-CONHSO$_2$R$^{11}$ (where $R^{11}$ is alkyl, aryl, aralkyl, heteroaryl, heteroaralkyl, heterocycloalkyl, or heterocycloalkylalkyl), wherein any rings comprising $R^3$ are optionally substituted with one or two groups independently selected from hydroxy, hydroxyalkyl, carboxy, alkoxycarbonyl, alkyl or —CONR$^a$R$^b$ where $R^a$ and $R^b$ are independently hydrogen or alkyl;

$R^x$ is hydrogen or halo; and $R^z$ is —SO$_2$NR$^{22}$R$^{23}$ (where $R^{22}$ is hydrogen or alkyl and $R^{23}$ is hydrogen, alkyl, aryl, aralkyl, heteroaryl, or heteroaralkyl, or $R^{22}$ and $R^{23}$ together with the nitrogen atom to which they are attached from heterocycloamino) or -(alkylene)-SO$_2$NR$^{24}$R$^{25}$ (where $R^{24}$ is hydrogen or alkyl and $R^{25}$ is hydrogen, alkyl, aryl, aralkyl, heteroaryl, or heteroaralkyl or $R^{24}$ and $R^{25}$ together with the nitrogen atom to which they are attached from heterocycloamino); and $R^{13}$ is hydrogen, hydroxy, (C$_{1-10}$)alkoxy, —C(O)R$^{35}$ where $R^{35}$ is alkyl, aryl, haloalkyl, or cyanoalkyl, or —C(O)OR$^{36}$ where $R^{36}$ is alkyl, hydroxyalkyl, acyl, or haloalkyl; or a pharmaceutically acceptable salt thereof.

(a) Within the above group Ib, a more preferred group of compounds is that wherein $R^3$ is hydrogen.

(b) Within the above group Ib, another more preferred group of compounds is that wherein $R^3$ is halo, preferably chloro or fluoro, more preferably fluoro.

(c) Within the above group Ib, another more preferred group of compounds is that wherein $R^3$ is —SO$_2$NHCOR$^6$ where $R^6$ is as defined in its broadest terms in the Summary of the Invention. Preferably $R^6$ is alkyl, aralkyl, aryl, heteroaralkyl or heterocycloalkylalkyl. More preferably $R^3$ is aminosulfonyl, —SO$_2$NHCOCH$_3$, 2-phenyethylcarbonyl-aminosulfonyl, phenylcarbonylaminosulfonyl, 3-phenylpropylcarbonylaminosulfonyl, benzylcarbonylaminosulfonyl, 2-(3,4-dichlorophenyl)ethylcarbonylaminosulfonyl, 2-pyridin-3-ylethylcarbonylaminosulfonyl, 2-piperidin-3-ylethylcarbonylaminosulfonyl. Even more preferably $R^3$ is —SO$_2$NHCOCH$_3$.

(d) Within the above group Ib, yet another more preferred group of compounds is that wherein $R^3$ is —CONR$^7$R$^8$ (where $R^7$ is hydrogen, alkyl, hydroxyalkyl, or alkoxyalkyl and $R^8$ is hydrogen, alkyl, hydroxyalkyl, alkoxyalkyl, aminoalkyl, aryl, aralkyl, heteroaryl, heteroaralkyl, or hetereocycloalkylalkyl or $R^7$ and $R^8$ together with the nitrogen atom to which they are attached form heterocycloalkylamino, wherein any rings comprising $R^3$ are optionally substituted with one or two groups independently selected from hydroxy, hydroxyalkyl, carboxy, alkoxycarbonyl, alkyl or —CONR$^a$R$^b$ where $R^a$ and $R^b$ are independently hydrogen or alkyl). Preferably $R^7$ is hydrogen or alkyl, and $R^8$ is hydrogen, alkyl, aralkyl, or heteroaralkyl, or $R^7$ and $R^8$ together with the nitrogen atom to which they are attached form heterocycloalkylamino. More preferably, $R^7$ and $R^8$ together with the nitrogen atom to which they are attached form heterocycloalkylamino, optionally substituted with one or two groups independently selected from hydroxy, hydroxyalkyl, carboxy, alkoxycarbonyl, alkyl or —CONR$^a$R$^b$ where $R^a$ and $R^b$ are independently hydrogen or alkyl. Even more preferably, $R^3$ is aminocarbonyl, dimethylaminocarbonyl, 2-morpholin-4-ylethylaminocarbonyl, 2-phenethylaminocarbonyl, methylaminocarbonyl, pyridin-2-ylmethylaminocarbonyl, furan-2-ylmethylaminocarbonyl, 2-pyridin-4-ylethylaminocarbonyl, 2-pyridin-3-ylethylaminocarbonyl, 2-pyridin-2-ylethylaminocarbonyl, pyridin-4-ylmethylamino-carbonyl, pyrrolidin-1-ylcarbonyl, piperidin-1-ylcarbonyl, morpholin-4-ylcarbonyl, piperazin-1-ylcarbonyl or thiazolidin-1-ylcarbonyl, wherein any rings comprising $R^3$ are optionally substituted with one or two groups independently selected from hydroxy, hydroxyalkyl, carboxy, alkoxycarbonyl, alkyl or —CONR$^a$R$^b$ where $R^a$ and $R^b$ are independently hydrogen or alkyl. Particularly, $R^3$ is 4-hydroxypiperidin-1-ylcarbonyl, piperidin-1-ylcarbonyl, 2-methoxycarbonylpyrrolidin-1-ylcarbonyl, 4-methylpiperazin-1-ylcarbonyl, pyrrolidin-1-ylcarbonyl, morpholin-4-ylcarbonyl, (2R) or (2S)-aminocarbonylpyrrolidin-1-ylcarbonyl, (2R) or (2S)-carboxypyrrolidin-1-ylcarbonyl, (2R) or (2S)-methoxycarbonyl, pyrrolidin-1-ylcarbonyl, dimethylaminocarbonyl, 3RS-aminocarbonylpiperidin-1-ylcarbonyl, 2S-methoxycarbonyl-4R-hydroxypyrrolidin-1-ylcarbonyl, (2R) or (2S)-dimethylaminocarbonylpyrrolidin-1-ylcarbonyl, 2-(S)-hydroxymethylpyrrolidin-1-ylcarbonyl, 3R-hydroxypyrrolidin-1-ylcarbonyl, 2S-methoxycarbonyl-4S-hydroxypyrrolidin-1-ylcarbonyl, 2S-carboxy-4R-hydroxypyrrolidin-1-ylcarbonyl, 2S-aminocarbonyl-4R-hydroxypyrrolidin-1-ylcarbonyl, 2S-carboxy-4S-hydroxypyrrolidin-1-ylcarbonyl, 2R-methoxycarbonyl-4R-hydroxypyrrolidin-1-ylcarbonyl or 2R-carboxy-4R-hydroxypyrrolidin-1-ylcarbonyl.

(e) Within the above group Ib, yet another more preferred group of compounds is that wherein $R^3$ is -(alkylene)-CONR$^9$R$^{10}$ (where $R^9$ is hydrogen, alkyl, hydroxyalkyl, alkoxyalkyl and $R^{10}$ is hydrogen, alkyl, hydroxyalkyl, alkoxyalkyl, aminoalkyl, aryl, aralkyl, heteroaryl, heteroaralkyl, or heterocycloalkylalkyl, or $R^9$ and $R^{10}$ together with the nitrogen atom to which they are attached form heterocycloalkylamino), wherein any rings comprising $R^3$ are optionally substituted with one or two groups independently selected from hydroxy, hydroxyalkyl, carboxy, alkoxycarbonyl, alkyl or —CONR$^a$R$^b$ where $R^a$ and $R^b$ are independently hydrogen or alkyl.

(f) Within the above group Ib, yet another more preferred group of compounds is that wherein $R^3$ is haloalkyl or haloalkoxy, preferably trifluoromethyl or trifluoromethoxy.
(g) Within the above group Ib, yet another more preferred group of compounds is that wherein $R^3$ is alkyl or alkoxy, preferably methyl or methoxy.
(h) Within the above group Ib, yet another more preferred group of compounds is that wherein $R^3$ is tetrazol-5-y or tetrazol-5-ylmethyl.
(i) Within the above group Ib, another more preferred group of compounds is that wherein $R^3$ is aminosulfonyl or dimethylaminosulfonyl, preferably aminosulfonyl.

Within the above preferred and more preferred groups (a-i), a particularly preferred group of compounds is that wherein:
$R^x$ is fluoro, chloro, or hydrogen, preferably hydrogen; and
$R^z$ is aminosulfonyl, methylaminosulfonyl, dimethylaminosulfonyl, aminosulfonylmethyl, methylaminosulfonylmethyl, or dimethylaminosulfonylmethyl.

Within the above preferred, more preferred, and even more preferred groups, a particularly preferred group of compounds is that wherein:
$R^{13}$ is hydrogen, hydroxy, methoxy, or ethoxycarbonyl, preferably hydrogen.

(III) Yet another preferred group of compounds of Formula I are those wherein the moiety:

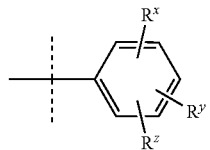

is 3'-acetylphenyl, 3'-hydroxyphenyl, 2'-hydroxyphenyl, 3'-aminocarbonylphenyl, 3'-cyanophenyl, 5'-fluoro-2'-hydroxyphenyl, 5'-chloro-2'-hydroxyphenyl, 2'-hydroxymethylphenyl, 2'-hydroxyphenyl, 5'-carboxy-2'-hydroxyphenyl, 2',5'-dihydroxyphenyl, 5'-cyano-2'-methoxyphenyl, 5'-aminocarbonyl-2'-methoxyphenyl, 2',6'-dihydroxyphenyl, 2'-hydroxy-5'-nitrophenyl, 2'-cyanophenyl, 3'-hydroxymethylphenyl, 5'-cyano-2'-hydroxyphenyl, 5'-aminocarbonyl-2'-hydroxyphenyl, 2',6'-dihydroxyphenyl, 5'-aminomethyl-2'-hydroxyphenyl, 2'-hydroxy-5'-ureidomethylphenyl, 2'-hydroxy-5'-imidazol-2-ylphenyl, 5'-amino-2'-hydroxyphenyl, 2'-hydroxy-5'-ureidophenyl, 2'-hydroxy-5'-(2-morpholin-4-ylethyl)aminocarbonyl-phenyl, 3'-bromo-2'-hydroxy-5'-hydroxymethylphenyl, 5'-(2-cyanoethyl)-2'-hydroxyphenyl, 3'-bromo-5'-carboxymethyl-2'-hydroxyphenyl, 5'-(2-carboxyethyl)-2'-hydroxyphenyl, 5'-aminocarbonylmethyl-2'-hydroxyphenyl, 3',5'-dichloro-2'-hydroxyphenyl, 2'-hydroxy-5'-[2-(2-hydroxyethoxyl)ethylaminocarbonyl]phenyl, 5'-dimethylaminosulfonylamino-2'-hydroxy-phenyl, 3'-bromo-5'-chloro-2'-hydroxyphenyl, 2'-hydroxy-5'-(4-methylpiperazin-1-ylcarbonyl)phenyl, 2'-hydroxy-5'-(4-methylpiperazin-1-ylemthyl)phenyl, 5'-carbamimidoyl-2'-hydroxyphenyl, 5'-(2-dimethylaminoethylaminocarbonyl)-2'-hydroxyphenyl, or 5'-aminocarbonyl-2'-hydroxyphenyl. Preferably 2'-hydroxyphenyl, 5'-fluoro-2'-hydroxyphenyl, 5'-chloro-2'-hydroxyphenyl, 2'-hydroxymethylphenyl, 2'-hydroxyphenyl, 5'-carboxy-2'-hydroxyphenyl, 2',5'-dihydroxyphenyl, 2',6'-dihydroxyphenyl, 2'-hydroxy-5'-nitrophenyl, 5'-cyano-2'-hydroxyphenyl, 5'-aminocarbonyl-2'-hydroxyphenyl, 2',6'-dihydroxyphenyl, 5'-aminomethyl-2'-hydroxyphenyl, 2'-hydroxy-5'-ureidomethylphenyl, 2'-hydroxy-5'-imidazol-2-ylphenyl, 5'-amino-2'-hydroxyphenyl, 2'-hydroxy-5'-ureidophenyl, 2'-hydroxy-5'-(2-morpholin-4-ylethyl)aminocarbonyl-phenyl, 3'-bromo-2'-hydroxy-5'-hydroxymethylphenyl, 5'-(2-cyanoethyl)-2'-hydroxyphenyl, 3'-bromo-5'-carboxymethyl-2'-hydroxyphenyl, 5'-(2-carboxyethyl)-2'-hydroxyphenyl, 5'-aminocarbonylmethyl-2'-hydroxyphenyl, 3',5'-dichloro-2'-hydroxyphenyl, 2'-hydroxy-5'-[2-(2-hydroxyethoxyl)ethylaminocarbonyl]phenyl, 5'-dimethylaminosulfonylamino-2'-hydroxy-phenyl, 3'-bromo-5'-chloro-2'-hydroxyphenyl, 2'-hydroxy-5'-(4-methylpiperazin-1-ylcarbonyl)phenyl, 2'-hydroxy-5'-(4-methylpiperazin-1-ylmethyl)phenyl, 5'-carbamimidoyl-2'-hydroxyphenyl, 5'-methylaminocarbonylmethyl-2'-hydroxyphenyl, 5'-(2-dimethylaminoethylaminocarbonyl)-2'-hydroxyphenyl, or 5'-aminocarbonyl-2'-hydroxyphenyl. More preferably, 2',6'-dihydroxyphenyl, 5'-fluoro-2'-hydroxyphenyl, 3'-aminosulfonylphenyl, 5'-aminocarbonyl-2'-hydroxyphenyl, 5'-aminocarbonylmethyl-2'-hydroxyphenyl, 5'-methylaminocarbonylmethyl-2'-hydroxyphenyl, 5'-hydroxymethyl-2'-hydroxyphenyl, 5'-acetylaminomethyl-2'-hydroxyphenyl, 2'-hydroxy-5'-ureidophenyl; 2'-hydroxy-5'-ureidomethylphenyl, 2'-hydroxy-5'-N-methylureidomethylphenyl, 2'-hydroxy-5'-N,N-dimethylureidomethylphenyl, or 5'-methylsulfonylamino-2'-hydroxyphenyl.

Within this group, a more preferred group of compounds is that wherein R and $R^2$ are hydrogen, $X^1$ is nitrogen, $X^2$-$X^4$ are carbon and $R^3$ is hydrogen, fluoro, chloro, methyl, trifluoromethyl, trifluoromethoxy, methoxy, aminocarbonyl, dimethylaminocarbonyl, tetrazol-5-yl, tetrazol-5-ylmethyl cyanomethyl, acetylaminosulfonyl, or aminosulfonyl.

(IV) Yet another preferred group of compounds of Formula I are those wherein the moiety:

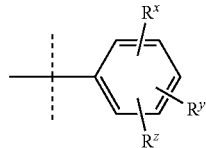

is a group of the formula:

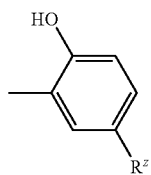

where $R^z$ is fluoro, aminosulfonyl, ureidomethyl, —$CH_2NHCONCH_3$, —$CH_2NHCON$-tert-butyl, N,N-dimethylureidomethyl, aminomethyl, piperazin-1-ylcarbonylmethyl, carboxymethyl, —$CH_2NHCOCH_2OH$, aminocarbonyl, acetylaminomethyl, aminocarbonylmethyl, methylaminocarbonylmethyl, dimethylaminocarbonylmethyl, 2-hydroxyethylaminocarbonylmethyl, morpholin-4-ylcarbonylmethyl, methoxycarbonylaminomethyl, hydroxymethyl, or methylsulfonylaminomethyl.

Reference to the preferred embodiments set forth above is meant to include all combinations of particular and preferred groups unless stated otherwise.

(V) Another preferred group of compounds of Formula I are the following:

2-{2-[5-(5-carbamimidoyl-1H-benzoimidazol-2-yl)-6,2'-dihydroxy-5'-sulfamoyl-biphenyl-3-yl]-acetylamino}-succinamic (Compound 121);

({2-[5-(5-carbamimidoyl-1H-benzoimidazol-2-yl)-6,2'-dihydroxy-5'-sulfamoyl-biphenyl-3-yl]-acetyl}-carboxymethyl-amino)-acetic acid (Compound 122);

2-{2-[5-(5-carbamimidoyl-1H-benzoimidazol-2-yl)-6,2'-dihydroxy-5'-sulfamoyl-biphenyl-3-yl]-acetylamino}-succinic acid (Compound 123);

1-{2-[5-(5-carbamimidoyl-1H-benzoimidazol-2-yl)-6,2'-dihydroxy-5'-sulfamoyl-biphenyl-3-yl]-acetyl}-pyrrolidine-2-carboxamide (Compound 124);

1-{2-[5-(5-carbamimidoyl-1H-benzoimidazol-2-yl)-6,2'-dihydroxy-5'-sulfamoyl-biphenyl-3-yl]-acetyl}-4-hydroxy-pyrrolidine-2-carboxylic acid (Compound 125);

2-[5-(5-carbamimidoyl-1H-benzoimidazol-2-yl)-6,2'-dihydroxy-5'-sulfamoyl-biphenyl-3-yl]-acetamide (Compound 126);

2-[5-(5-carbamimidoyl-1H-benzoimidazol-2-yl)-6,2'-dihydroxy-5'-sulfamoyl-biphenyl-3-yl]-N,N-dimethyl-acetamide (Compound 127);

2-[5-(5-carbamimidoyl-1H-benzoimidazol-2-yl)-6,2'-dihydroxy-5'-sulfamoyl-biphenyl-3-yl]-N-(2-hydroxy-1-hydroxymethyl-ethyl)-acetamide (Compound 128);

{2-[5-(5-carbamimidoyl-1H-benzoimidazol-2-yl)-6,2'-dihydroxy-5'-sulfamoyl-biphenyl-3-yl]-acetylamino}-acetic acid (Compound 129);

2-[5-(5-carbamimidoyl-1H-benzoimidazol-2-yl)-6,2'-dihydroxy-5'-sulfamoyl-biphenyl-3-yl]-N-carbamoylmethyl-acetamide (Compound 130);

2-[5-(5-carbamimidoyl-1H-benzoimidazol-2-yl)-6,2'-dihydroxy-5'-sulfamoyl-biphenyl-3-yl]-N-(2-dimethylamino-ethyl)-acetamide (Compound 131);

2-[5-(5-carbamimidoyl-1H-benzoimidazol-2-yl)-6,2'-dihydroxy-5'-sulfamoyl-biphenyl-3-yl]-N-(3-dimethylamino-propyl)-acetamide (Compound 132);

3-{2-[5-(5-carbamimidoyl-1H-benzoimidazol-2-yl)-6,2'-dihydroxy-5'-sulfamoyl-biphenyl-3-yl]-acetylamino}-propionic acid (Compound 133);

2-[5-(5-carbamimidoyl-1H-benzoimidazol-2-yl)-6,2'-dihydroxy-5'-sulfamoyl-biphenyl-3-yl]-N-methyl-N-{2-[2-(2-methylamino-ethoxy)-ethoxy]-ethyl}-acetamide (Compound 134);

2-[5-(5-carbamimidoyl-1H-benzoimidazol-2-yl)-6,2'-dihydroxy-5'-sulfamoyl-biphenyl-3-yl]-N—(S,4,5,6-tetrahydroxy-tetrahydro-pyran-2-ylmethyl)-acetamide (Compound 135);

2-[5-(5-carbamimidoyl-1H-benzoimidazol-2-yl)-6,2'-dihydroxy-5'-sulfamoyl-biphenyl-3-yl]-N-(2,4,5-trihydroxy-6-hydroxymethyl-tetrahydro-pyran-3-yl)-acetamide (Compound 136);

2-[5-(5-carbamimidoyl-1H-benzoimidazol-2-yl)-6,2'-dihydroxy-5'-sulfamoyl-biphenyl-3-yl]-N-methyl-N-(2,3,4,5,6-pentahydroxy-hexyl)-acetamide (Compound 137);

2-[5-(5-carbamimidoyl-1H-benzoimidazol-2-yl)-6,2'-dihydroxy-5'-sulfamoyl-biphenyl-3-yl]-N-(2-hydroxy-1,1-bis-hydroxymethyl-ethyl)-acetamide (Compound 138);

2-[5-(5-carbamimidoyl-1H-benzoimidazol-2-yl)-6,2'-dihydroxy-5'-sulfamoyl-biphenyl-3-yl]-N-methyl-acetamide (Compound 139);

2-{2-[5-(5-carbamimidoyl-1H-benzoimidazol-2-yl)-6,2'-dihydroxy-5'-sulfamoyl-biphenyl-3-yl]-acetylamino}-succinamide (Compound 140);

2-[5-(5-carbamimidoyl-1H-benzoimidazol-2-yl)-6,2'-dihydroxy-5'-sulfamoyl-biphenyl-3-yl]-N-[(2,4,5-trihydroxy-6-hydroxymethyl-tetrahydro-pyran-3-ylcarbamoyl)-methyl]-acetamide (Compound 141);

2-[5-(5-carbamimidoyl-1H-benzoimidazol-2-yl)-6,2'-dihydroxy-5'-sulfamoyl-biphenyl-3-yl]-N-{3-[2-(2-ethoxy-ethoxy)-ethoxy]-propyl}-acetamide (Compound 142);

(2-{2-[5-(5-carbamimidoyl-1H-benzoimidazol-2-yl)-6,2'-dihydroxy-5'-sulfamoyl-biphenyl-3-yl]-acetylamino}-ethyl)-phosphonic acid (Compound 143);

{2-[{2-[5-(5-carbamimidoyl-1H-benzoimidazol-2-yl)-6,2'-dihydroxy-5'-sulfamoyl-biphenyl-3-yl]-acetyl}-(2-phosphono-ethyl)-amino]-ethyl}-phosphonic acid (Compound 144);

2-{2-[5-(5-carbamimidoyl-1H-benzoimidazol-2-yl)-6,2'-dihydroxy-5'-sulfamoyl-biphenyl-3-yl]-2-methyl-propionylamino}-succinamic acid (Compound 145);

({2-[5-(5-carbamimidoyl-1H-benzoimidazol-2-yl)-6,2'-dihydroxy-5'-sulfamoyl-biphenyl-3-yl]-2-methyl-propionyl}-carboxymethyl-amino)-acetic acid (Compound 146);

2-{2-[5-(5-carbamimidoyl-1H-benzoimidazol-2-yl)-6,2'-dihydroxy-5'-sulfamoyl-biphenyl-3-yl]-2-methyl-propionylamino}-succinic acid (Compound 147);

1-{2-[5-(5-carbamimidoyl-1H-benzoimidazol-2-yl)-6,2'-dihydroxy-5'-sulfamoyl-biphenyl-3-yl]-2-methyl-propionyl}-pyrrolidine-2-carboxamide (Compound 148);

1-{2-[5-(5-carbamimidoyl-1H-benzoimidazol-2-yl)-6,2'-dihydroxy-5'-sulfamoyl-biphenyl-3-yl]-2-methyl-propionyl}-4-hydroxy-pyrrolidine-2-carboxylic acid (Compound 149);

2-[5-(5-carbamimidoyl-1H-benzoimidazol-2-yl)-6,2'-dihydroxy-5'-sulfamoyl-biphenyl-3-yl]-isobutyramide (Compound 150);

2-[5-(5-carbamimidoyl-1H-benzoimidazol-2-yl)-6,2'-dihydroxy-5'-sulfamoyl-biphenyl-3-yl]-N,N-dimethyl-isobutyramide (Compound 151);

2-[5-(5-carbamimidoyl-1H-benzoimidazol-2-yl)-6,2'-dihydroxy-5'-sulfamoyl-biphenyl-3-yl]-N-(2-hydroxy-1-hydroxymethyl-ethyl)-isobutyramide (Compound 152);

{2-[5-(5-carbamimidoyl-1H-benzoimidazol-2-yl)-6,2'-dihydroxy-5'-sulfamoyl-biphenyl-3-yl]-2-methyl-propionylamino}-acetic acid (Compound 153);

2-[5-(5-carbamimidoyl-1H-benzoimidazol-2-yl)-6,2'-dihydroxy-5'-sulfamoyl-biphenyl-3-yl]-N-carbamoylmethyl-isobutyramide (Compound 154);

2-[5-(5-carbamimidoyl-1H-benzoimidazol-2-yl)-6,2'-dihydroxy-5'-sulfamoyl-biphenyl-3-yl]-N-(2-dimethylamino-ethyl)-isobutyramide (Compound 155);

2-[5-(5-carbamimidoyl-1H-benzoimidazol-2-yl)-6,2'-dihydroxy-5'-sulfamoyl-biphenyl-3-yl]-N-(3-dimethylamino-propyl)-isobutyramide (Compound 156);

3-{2-[5-(5-carbamimidoyl-1H-benzoimidazol-2-yl)-6,2'-dihydroxy-5'-sulfamoyl-biphenyl-3-yl]-2-methyl-propionylamino}-propionic acid (Compound 157);

2-[5-(5-carbamimidoyl-1H-benzoimidazol-2-yl)-6,2'-dihydroxy-5'-sulfamoyl-biphenyl-3-yl]-N-methyl-N-{2-[2-(2-methylamino-ethoxy)-ethoxy]-ethyl}-isobutyramide (Compound 158);

2-[5-(5-carbamimidoyl-1H-benzoimidazol-2-yl)-6,2'-dihydroxy-5'-sulfamoyl-biphenyl-3-yl]-N-(3,4,5,6-tetrahydroxy-tetrahydro-pyran-2-ylmethyl)-isobutyramide (Compound 159);

2-[5-(5-carbamimidoyl-1H-benzoimidazol-2-yl)-6,2'-dihydroxy-5'-sulfamoyl-biphenyl-3-yl]-N-methyl-N-(2,3,4,5,6-pentahydroxy-hexyl)-isobutyramide (Compound 161);

2-[5-(5-carbamimidoyl-1H-benzoimidazol-2-yl)-6,2'-dihydroxy-5'-sulfamoyl-biphenyl-3-yl]-N-(2-hydroxy-1,1-bis-hydroxymethyl-ethyl)-isobutyramide (Compound 162);

2-[5-(5-carbamimidoyl-1H-benzoimidazol-2-yl)-6,2'-dihydroxy-5'-sulfamoyl-biphenyl-3-yl]-N-methyl-isobutyramide (Compound 163);

2S-{2-[5-(5-carbamimidoyl-1H-benzoimidazol-2-yl)-6,2'-dihydroxy-5'-sulfamoyl-biphenyl-3-yl]-2-methyl-propionylamino}-succinamide (Compound 164);

2-[5-(5-carbamimidoyl-1H-benzoimidazol-2-yl)-6,2'-dihydroxy-5'-sulfamoyl-biphenyl-3-yl]-N-[(2,4,5-trihydroxy-6-hydroxymethyl-tetrahydro-pyran-3-ylcarbamoyl)-methyl]-isobutyramide (Compound 165);

2-[5-(5-carbamimidoyl-1H-benzoimidazol-2-yl)-6,2'-dihydroxy-5'-sulfamoyl-biphenyl-3-yl]-N-{3-[2-(2-ethoxy-ethoxy)-ethoxy]-propyl}-isobutyramide (Compound 166);

(2-{2-[5-(5-carbamimidoyl-1H-benzoimidazol-2-yl)-6,2'-dihydroxy-5'-sulfamoyl-biphenyl-3-yl]-2-methyl-propionylamino}-ethyl)-phosphonic acid (Compound 167);

{2-[{2-[5-(5-carbamimidoyl-1H-benzoimidazol-2-yl)-6,2'-dihydroxy-5'-sulfamoyl-biphenyl-3-yl]-2-methyl-propionyl}-(2-phosphono-ethyl)-amino]-ethyl}-phosphonic acid (Compound 168);

2-{2-[5-(5-carbamimidoyl-1H-benzoimidazol-2-yl)-6,2'-dihydroxy-5'-ureidomethyl-biphenyl-3-yl]-2-methyl-propionylamino}-succinamic acid (Compound 169);

({2-[5-(5-carbamimidoyl-1H-benzoimidazol-2-yl)-6,2'-dihydroxy-5'-ureidomethyl-biphenyl-3-yl]-2-methyl-propionyl}-carboxymethyl-amino)-acetic acid (Compound 170);

2-{2-[5-(5-carbamimidoyl-1H-benzoimidazol-2-yl)-6,2'-dihydroxy-5'-ureidomethyl-biphenyl-3-yl]-2-methyl-propionylamino}-succinic acid (Compound 171);

1-{2-[5-(5-carbamimidoyl-1H-benzoimidazol-2-yl)-6,2'-dihydroxy-5'-ureidomethyl-biphenyl-3-yl]-2-methyl-propionyl}-pyrrolidine-2-carboxamide (Compound 172);

1-{2-[5-(5-carbamimidoyl-1H-benzoimidazol-2-yl)-6,2'-dihydroxy-5'-ureidomethyl-biphenyl-3-yl]-2-methyl-propionyl}-4-hydroxy-pyrrolidine-2-carboxylic acid (Compound 173);

2-[5-(5-carbamimidoyl-1H-benzoimidazol-2-yl)-6,2'-dihydroxy-5'-ureidomethyl-biphenyl-3-yl]-isobutyramide (Compound 174);

2-[5-(5-carbamimidoyl-1H-benzoimidazol-2-yl)-6,2'-dihydroxy-5'-ureidomethyl-biphenyl-3-yl]-N,N-dimethyl-isobutyramide (Compound 175);

2-[5-(5-carbamimidoyl-1H-benzoimidazol-2-yl)-6,2'-dihydroxy-5'-ureidomethyl-biphenyl-3-yl]-N-(2-hydroxy-1-hydroxymethyl-ethyl)-isobutyramide (Compound 176);

{2-[5-(5-carbamimidoyl-1H-benzoimidazol-2-yl)-6,2'-dihydroxy-5'-ureidomethyl-biphenyl-3-yl]-2-methyl-propionylamino}-acetic acid (Compound 177);

2-[5-(5-carbamimidoyl-1H-benzoimidazol-2-yl)-6,2'-dihydroxy-5'-ureidomethyl-biphenyl-3-yl]-N-carbamoylmethyl-isobutyramide (Compound 178);

2-[5-(5-carbamimidoyl-1H-benzoimidazol-2-yl)-6,2'-dihydroxy-5'-ureidomethyl-biphenyl-3-yl]-N-(2-dimethylamino-ethyl)-isobutyramide (Compound 179);

2-[5-(5-carbamimidoyl-1H-benzoimidazol-2-yl)-6,2'-dihydroxy-5'-ureidomethyl-biphenyl-3-yl]-N-(3-dimethylamino-propyl)-isobutyramide (Compound 180);

3-{2-[5-(5-carbamimidoyl-1H-benzoimidazol-2-yl)-6,2'-dihydroxy-5'-ureidomethyl-biphenyl-3-yl]-2-methyl-propionylamino}-propionic acid (Compound 181);

2-[5-(5-carbamimidoyl-1H-benzoimidazol-2-yl)-6,2'-dihydroxy-5'-ureidomethyl-biphenyl-3-yl]-N-(3,4,5,6-tetrahydroxy-tetrahydro-pyran-2-ylmethyl)-isobutyramide (Compound 182);

2-[5-(5-carbamimidoyl-1H-benzoimidazol-2-yl)-6,2'-dihydroxy-5'-ureidomethyl-biphenyl-3-yl]-N-methyl-N-{2-[2-(2-methylamino-ethoxy)-ethoxy]-ethyl}-isobutyramide (Compound 183);

2-[5-(5-carbamimidoyl-1H-benzoimidazol-2-yl)-6,2'-dihydroxy-5'-ureidomethyl-biphenyl-3-yl]-N-(2,4,5-trihydroxy-6-hydroxymethyl-tetrahydro-pyran-3-yl)-isobutyramide (Compound 184);

2-[5-(5-carbamimidoyl-1H-benzoimidazol-2-yl)-6,2'-dihydroxy-5'-ureidomethyl-biphenyl-3-yl]-N-methyl-N-(2,3,4,5,6-pentahydroxy-hexyl)-isobutyramide (Compound 185);

2-[5-(5-carbamimidoyl-1H-benzoimidazol-2-yl)-6,2'-dihydroxy-5'-ureidomethyl-biphenyl-3-yl]-N-(2-hydroxy-1,1-bis-hydroxymethyl-ethyl)-isobutyramide (Compound 186);

2-[5-(5-carbamimidoyl-1H-benzoimidazol-2-yl)-6,2'-dihydroxy-5'-ureidomethyl-biphenyl-3-yl]-N-methyl-isobutyramide (Compound 187);

2-{2-[5-(5-carbamimidoyl-1H-benzoimidazol-2-yl)-6,2'-dihydroxy-5'-ureidomethyl-biphenyl-3-yl]-2-methyl-propionylamino}-succinamide (Compound 188);

2-[5-(5-carbamimidoyl-1H-benzoimidazol-2-yl)-6,2'-dihydroxy-5'-ureidomethyl-biphenyl-3-yl]-N-[(2,4,5-trihydroxy-6-hydroxymethyl-tetrahydro-pyran-3-ylcarbamoyl)-methyl]-isobutyramide (Compound 189);

2-[5-(5-carbamimidoyl-1H-benzoimidazol-2-yl)-6,2'-dihydroxy-5'-ureidomethyl-biphenyl-3-yl]-N-{3-[2-(2-ethoxy-ethoxy)-ethoxy]-propyl}-isobutyramide (Compound 190);

(2-{2-[5-(5-carbamimidoyl-1H-benzoimidazol-2-yl)-6,2'-dihydroxy-5'-ureidomethyl-biphenyl-3-yl]-2-methyl-propionylamino}-ethyl)-phosphonic acid (Compound 191);

{2-[{2-[5-(5-carbamimidoyl-1H-benzoimidazol-2-yl)-6,2'-dihydroxy-5'-ureidomethyl-biphenyl-3-yl]-2-methyl-propionyl}-(2-phosphono-ethyl)-amino]-ethyl}-phosphonic acid (Compound 192);

2-{[5-(5-carbamimidoyl-1H-benzoimidazol-2-yl)-6,2'-dihydroxy-5'-sulfamoyl-biphenyl-3-carbonyl]-amino}-succinamic acid (Compound 193);

{[5-(5-carbamimidoyl-1H-benzoimidazol-2-yl)-6,2'-dihydroxy-5'-sulfamoyl-biphenyl-3-carbonyl]-carboxymethyl-amino}-acetic acid (Compound 194);

2-{[5-(5-carbamimidoyl-1H-benzoimidazol-2-yl)-6,2'-dihydroxy-5'-sulfamoyl-biphenyl-3-carbonyl]-amino}-succinic acid (Compound 195);

1-{2-[5-(5-carbamimidoyl-1H-benzoimidazol-2-yl)-6,2'-dihydroxy-5'-sulfamoyl-biphenyl-3-yl]-acetyl}-pyrrolidine-2-carboxylic acid (Compound 196);

1-{2-[5-(5-carbamimidoyl-1H-benzoimidazol-2-yl)-6,2'-dihydroxy-5'-sulfamoyl-biphenyl-3-yl]-acetyl}-4-hydroxy-pyrrolidine-2-carboxylic acid (Compound 197);

5-(5-carbamimidoyl-1H-benzoimidazol-2-yl)-6,2'-dihydroxy-5'-sulfamoyl-biphenyl-3-carboxamide (Compound 198);

5-(5-carbamimidoyl-1H-benzoimidazol-2-yl)-6,2'-dihydroxy-5'-sulfamoyl-biphenyl-N,N-dimethyl-3-carboxamide (Compound 199);

5-(5-carbamimidoyl-1H-benzoimidazol-2-yl)-6,2'-dihydroxy-N-(2-hydroxy-1-hydroxymethyl-ethyl)-5'-sulfamoyl-biphenyl-3-carboxamide (Compound 200);

{[5-(5-carbamimidoyl-1H-benzoimidazol-2-yl)-6,2'-dihydroxy-5'-sulfamoyl-biphenyl-3-carbonyl]-amino}-acetic acid (Compound 201);

5-(5-carbamimidoyl-1H-benzoimidazol-2-yl)-N-carbamoylmethyl-6,2'-dihydroxy-5'-sulfamoyl-biphenyl-3-carboxamide (Compound 202);

5-(5-carbamimidoyl-1H-benzoimidazol-2-yl)-6,2'-dihydroxy-N-(2-dimethylamino-ethyl)-5'-sulfamoyl-biphenyl-3-carboxamide (Compound 203);

3-{[5-(5-carbamimidoyl-1H-benzoimidazol-2-yl)-6,2'-dihydroxy-5'-sulfamoyl-biphenyl-3-carbonyl]-amino}-propionic acid (Compound 204);

5-(5-carbamimidoyl-1H-benzoimidazol-2-yl)-6,2'-dihydroxy-N-methyl-N-{2-[2-(2-methylamino-ethoxy)-ethoxy]-ethyl}-5'-sulfamoyl-biphenyl-3-carboxamide (Compound 205);

5-(5-carbamimidoyl-1H-benzoimidazol-2-yl)-6,2'-dihydroxy-N-(3,4,5,6-tetrahydroxy-tetrahydro-pyran-2-ylmethyl)-5'-sulfamoyl-biphenyl-3-carboxamide (Compound 206);

5-(5-carbamimidoyl-1H-benzoimidazol-2-yl)-6,2'-dihydroxy-N-(2,4,5-trihydroxy-6-hydroxymethyl-tetrahydropyran-3-yl)-5'-sulfamoyl-biphenyl-3-carboxamide (Compound 207);

5-(5-carbamimidoyl-1H-benzoimidazol-2-yl)-6,2'-dihydroxy-N-methyl-N-(2,3,4,5,6-pentahydroxy-hexyl)-5'-sulfamoyl-biphenyl-3-carboxamide (Compound 209);

5-(5-carbamimidoyl-1H-benzoimidazol-2-yl)-6,2'-dihydroxy-N-(2-hydroxy-1,1-bis-hydroxymethyl-ethyl)-5'-sulfamoyl-biphenyl-3-carboxamide (Compound 210);

5-(5-carbamimidoyl-1H-benzoimidazol-2-yl)-6,2'-dihydroxy-N-methyl-5'-sulfamoyl-biphenyl-3-carboxamide (Compound 211);

5-(5-carbamimidoyl-1H-benzoimidazol-2-yl)-6,2'-dihydroxy-N-[(2,4,5-trihydroxy-6-hydroxymethyl-tetrahydropyran-3-ylcarbamoyl)-methyl]-5'-sulfamoyl-biphenyl-3-carboxamide (Compound 213);

5-(5-carbamimidoyl-1H-benzoimidazol-2-yl)-6,2'-dihydroxy-N-{3-[2-(2-ethoxy-ethoxy)-ethoxy]-propyl}-5'-sulfamoyl-biphenyl-3-carboxamide (Compound 214);

(2-{[5-(5-carbamimidoyl-1H-benzoimidazol-2-yl)-6,2'-dihydroxy-5'-sulfamoyl-biphenyl-3-carbonyl]-amino}-ethyl)-phosphonic acid (Compound 214);

{2-[[5-(5-carbamimidoyl-1H-benzoimidazol-2-yl)-6,2'-dihydroxy-5'-sulfamoyl-biphenyl-3-carbonyl]-(2-phosphono-ethyl)-amino]-ethyl}-phosphonic acid (Compound 215);

5-(5-carbamimidoyl-1H-benzoimidazol-2-yl)-6,2'-dihydroxy-N,N-bis-(2-hydroxy-ethyl)-5'-methyl-biphenyl-3-carboxyamide (Compound 217);

(2-{[5-(5-carbamimidoyl-1H-benzoimidazol-2-yl)-6,2'-dihydroxy-5'-sulfamoyl-biphenyl-3-carbonyl]-amino}-ethyl)-trimethyl-ammonium (Compound 218);

2-{5-[4-(2-amino-ethyl)-piperazine-1-carbonyl]-2,2'-dihydroxy-5'-sulfamoyl-biphenyl-3-yl}-1H-benzoimidazole-5-carboxamidine (Compound 219);

2-amino-6-{[5-(5-carbamimidoyl-1H-benzoimidazol-2-yl)-6,2'-dihydroxy-5'-sulfamoyl-biphenyl-3-carbonyl]-amino}-hexanoic acid (Compound 220);

5-(5-carbamimidoyl-1H-benzoimidazol-2-yl)-6,2'-dihydroxy-N-hydroxy-5'-sulfamoyl-biphenyl-3-carboxamide (Compound 221);

5-(5-carbamimidoyl-1H-benzoimidazol-2-yl)-6,2'-dihydroxy-N,N-dimethyl-5'-sulfamoyl-biphenyl-3-carboxamide (Compound 222);

5-(5-carbamimidoyl-1H-benzoimidazol-2-yl)-6,2'-dihydroxy-5'-sulfamoyl-biphenyl-3-carboxamide (Compound 223);

1-[5-(5-carbamimidoyl-1H-benzoimidazol-2-yl)-6,2'-dihydroxy-5'-sulfamoyl-biphenyl-3-carbonyl]-pyrrolidine-2-carboxamide (Compound 224);

2-[2,2'-dihydroxy-5-(morpholine-4-carbonyl)-5'-sulfamoyl-biphenyl-3-yl]-1H-benzoimidazole-5-carboxamidine (Compound 225);

1-[5-(5-carbamimidoyl-1H-benzoimidazol-2-yl)-6,2'-dihydroxy-5'-sulfamoyl-biphenyl-3-carbonyl]-pyrrolidine-2-carboxylic acid (Compound 226);

[(2-{4-[5-(5-carbamimidoyl-1H-benzoimidazol-2-yl)-6,2'-dihydroxy-5'-sulfamoyl-biphenyl-3-carbonyl]-piperazin-1-yl}-ethylamino)-dimethylamino-methylene]-dimethyl-ammonium (Compound 228);

2-{2-[5-(5-carbamimidoyl-1H-benzoimidazol-2-yl)-6,2'-dihydroxy-5'-sulfamoyl-biphenyl-3-yl]-acetylamino}-ethanesulfonic acid (Compound 234);

2-[5-(5-carbamimidoyl-1H-benzoimidazol-2-yl)-6,2'-dihydroxy-5'-sulfamoyl-biphenyl-3-yl]-N-(2-morpholin-4-yl-ethyl)-acetamide (Compound 235);

2-[5-(5-carbamimidoyl-1H-benzoimidazol-2-yl)-6,2'-dihydroxy-5'-sulfamoyl-biphenyl-3-yl]-acetamide (Compound 238);

2-amino-6-{2-[5-(5-carbamimidoyl-1H-benzoimidazol-2-yl)-6,2'-dihydroxy-5'-sulfamoyl-biphenyl-3-yl]-acetylamino}-hexanoic acid (Compound 112);

2-{2,2'-dihydroxy-5-[2-(4-methyl-piperazin-1-yl)-2-oxo-ethyl]-5'-sulfamoyl-biphenyl-3-yl}-1H-benzoimidazole-5-carboxamidine (Compound 113);

(2-{2-[5-(5-carbamimidoyl-1H-benzoimidazol-2-yl)-6,2'-dihydroxy-5'-sulfamoyl-biphenyl-3-yl]-acetylamino}-ethyl)-trimethyl-ammonium (Compound 105);

5-(5-carbamimidoyl-1H-benzoimidazol-2-yl)-6,2'-dihydroxy-N-carbamoylmethyl-methyl-5'-sulfamoyl-biphenyl-3-carboxamide (Compound 106);

5-(5-carbamimidoyl-1H-benzoimidazol-2-yl)-6,2'-dihydroxy-N-(2-piperazin-1-yl-ethyl)-5'-sulfamoyl-biphenyl-3-carboxamide (Compound 107); and 5-(5-carbamimidoyl-1H-benzoimidazol-2-yl)-6,2'-dihydroxy-N-methyl-5'-sulfamoyl-biphenyl-3-carboxamide (Compound 229).

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula I in which $X^1$ is —N—, $R^{13}$ is hydrogen, $R^3$ is hydrogen, halo, alkyl, haloalkyl, cyanoalkyl, tetrazol-5-yl, tetrazol-5-ylalkyl, aminosulfonyl, —SO$_2$NHCOR$^6$, CONHSO$_2$R$^{11}$ or -(alkylene)-CONHSO$_2$R$^{11}$ where R$^6$ and R$^{11}$ are as described in the Summary of the Invention and $X^2$, $X^3$, $X^4$, $R^1$, $R^2$, $R^x$, $R^y$, and $R^z$ are as defined in the Summary of the Invention can be prepared as described in Scheme I below.

alkyl, haloalkyl, cyanoalkyl, tetrazol-5-yl, tetrazol-5-ylalkyl, aminosulfonyl, —SO$_2$NHCOR$^6$, —CONHSO$_2$R$^{11}$ or -(alkylene)-CONHSO$_2$R$^{11}$ where R$^6$ and R$^{11}$ are as described in the Summary of the Invention and X is halo, preferably bromo or iodo can be prepared as disclosed in method (a) above, by halogenating a compound of formula 1 (where R is hydrogen or hydroxy protecting group) with a suitable halogenating agent such as N-bromosuccinimide, N-iodosuccinimide, and the like. The reaction is carried out in a suitable organic solvent such as dimethylformamide.

Alternately, a compound of formula 4 can be prepared as disclosed in method (b) above, by formylating of a phenol derivative of formula 2 (where $R^1$ and $R^2$ are as defined in the Summary of the Invention and $R^3$ is hydrogen, halo, alkyl, haloalkyl, cyanoalkyl, tetrazol-5-yl, tetrazol-5-ylalkyl, or -(alkylene)-CONHSO$_2$R$^{11}$ where R$^6$ and R$^{11}$ are as described

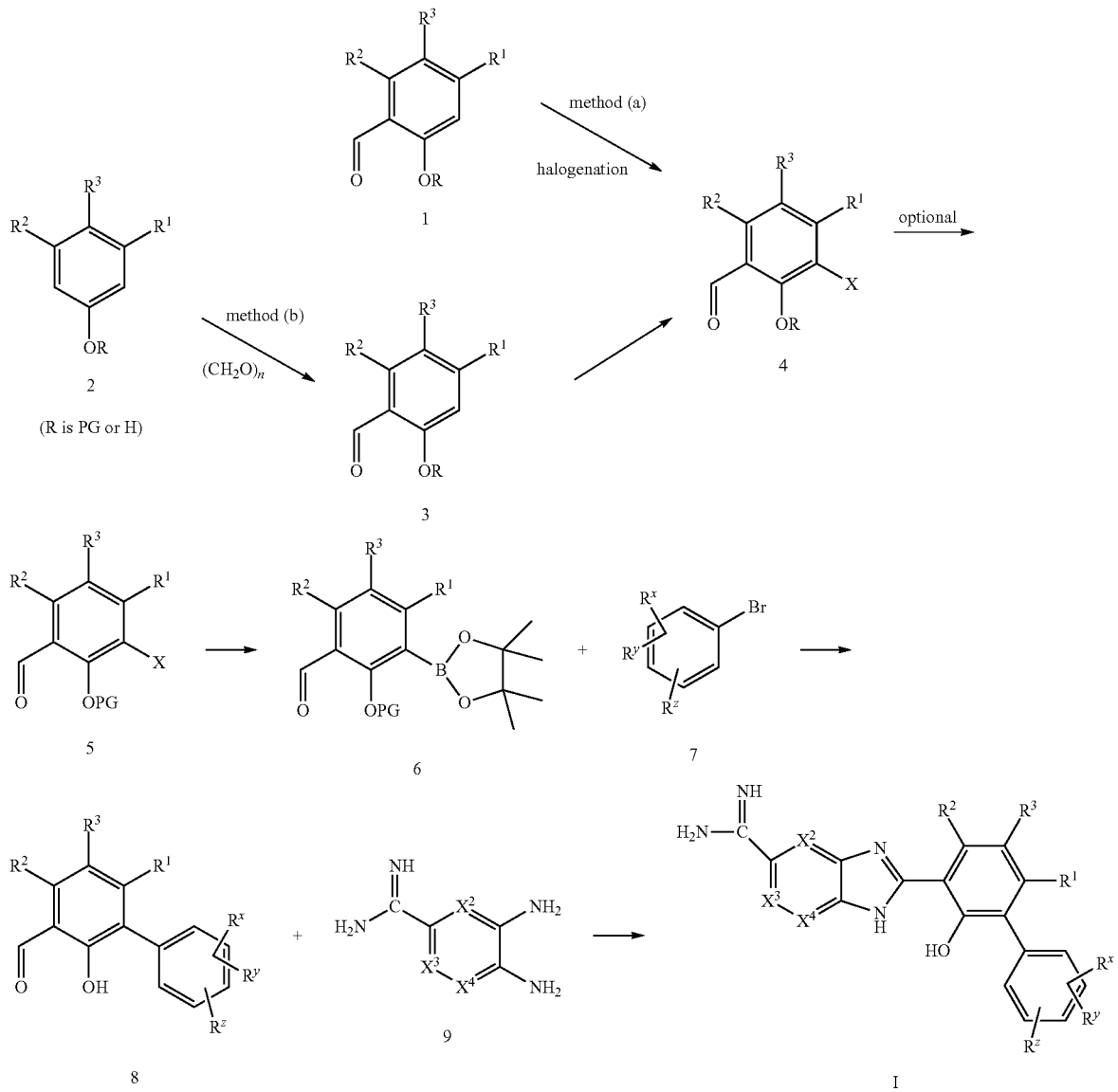

Scheme I

A compound of formula 4 where $R^1$ and $R^2$ are as defined in the Summary of the Invention and $R^3$ is hydrogen, halo, in the Summary of the Invention) to provide a compound of formula 3 which is then halogenated under the reaction conditions described in method (a) above. The formylation reaction is carried out in the presence of magnesium chloride and an organic base such as triethylamine, and the like and in a suitable organic solvent such as acetonitrile, and the like.

Compounds of formulae 1 and 2 are either commercially available or they can be prepared by methods well known in the art. For example, compounds of formula 1 such as 5-fluoro-2-hydroxybenzaldehyde, 5-methyl-2-hydroxybenzaldehyde, and salicylaldehyde are commercially available. Compounds of formula 2 such as 4-fluorophenol, phenol, p-cresol, and 4-hydroxybenzyl cyanide are commercially available. Compounds of formula 2 where $R^3$ is tetrazolyl or tetrazol-5-ylalkyl can be prepared from 4-hydroxybenzonitrile and 4-hydroxybenzyl cyanide respectively, by first protecting the hydroxy group with a suitable hydroxy protecting group and then treating the resulting compound with azidotributyltin in an aromatic organic solvent such as toluene, and the like. Compounds of formula 4 where $R^3$ is —CONHSO$_2$R$^{11}$ or -(alkylene)-CONHSO$_2$R$^{11}$ can be readily prepared from 3-formyl-4-methoxy-5-bromobenzoic acid and 2-(3-formyl-4-methoxy-5-bromophenyl)acetic acid by first converting the acid to an acid halide such as acid chloride with a suitable halogenating agent such as oxalyl chloride, and the like. Treatment of the acid halide with a sulfonamide of the formula $R^{11}SO_2NH_2$ where $R^{11}$ is as defined in the Summary of the Invention then provides the desired compound. 3-Formyl-4-methoxy-5-bromobenzoic acid and 2-(3-formyl-4-methoxy-5-bromophenyl)acetic acid can be prepared by the procedures disclosed in Applicants' patent application Ser. No. 10/190,147 the disclosure of which is incorporated herein by reference in its entirety. Compounds of formula 4 where $R^3$ is aminosulfonyl or —SO$_2$NHCOR$^6$ can be prepared as described in working Examples 12-14 below.

Protection of the hydroxy group in 4 (where R is hydrogen) with a suitable hydroxy protecting group such as alkyl, methoxyethoxymethyl, and the like, provides a compound of formula 5. A comprehensive list of suitable hydroxy protective groups can be found in T. W. Greene, *Protective Groups in Organic Synthesis*, John Wiley & Sons, Inc. 1981, the disclosure of which is incorporated herein by reference in its entirety. Preferred hydroxy protecting group is 2-methoxyethoxymethyl. The reaction is typically carried out in the presence of a base such as diisopropylethylamine, and the like and in a halogenated organic solvent such as dichloromethane, carbon tetrachloride, chloroform, and the like.

Compound 5 is converted into phenyl (4,4,5,5-tetramethyl-[1,3,2]dioxaborolanyl) derivative 6 by heating 5 with bispinacolato diboron in the presence of potassium acetate in the presence of Pd(dppf)Cl$_2$.

Treatment of 6 with a halobenzene of formula Ph(R$^x$, R$^y$, R$^z$)X where X is halo and R$^x$, R$^y$ and R$^z$ are as defined in the Summary of the Invention provides a biphenyl compound of formula 8. The reaction is carried out in the presence of a palladium catalyst such as tetrakis(triphenylphosphine)palladium and in a suitable organic solvent such as toluene or dimethoxyethane and a base such as aqueous sodium carbonate, potassium carbonate and the like. Compounds of formula 7 are either commercially available or they can be prepared by methods well known in the art. For example, 2-bromo-4-fluorophenol is commercially available. 1-(3-Bromo-4-methoxyethoxymethoxybenzyl)-3-tert-butyl urea can be prepared by treating 3-bromo-4-hydroxybenzonitrile with methoxyethoxymethyl chloride in the presence of a base such as diisopropylamine, and the like, followed by reduction of the resulting 3-bromo-4-methylethoxymethoxy)benzonitrile to 3-bromo-4-methoxyethoxymethoxybenzylamine with a suitable reducing agent such as diborane. Treatment of 3-bromo-4-methylethoxybenzylamine with tert-butylisocyanate then provides the desired compound. 1-(3-bromo-4-methoxyethoxymethoxybenzyl)-3-tert-butyl urea can be converted to 1-(3-bromo-4-methoxyethoxymethoxybenzyl)urea, if desired, by removal of the tert-butyl group under acidic hydrolysis reaction conditions.

Condensation of 8 with a 1,2-diamino compound of formula 9 provides a compound of Formula I where $X^1$ is —N—. The reaction is carried out in the presence of a suitable oxidant such as benzoquinone, air oxidation, or FeCl$_3$ and O$_2$ and in a suitable organic solvent such as methanol, ethanol, and the like.

Compounds of formula 9 are commercially available or they can be prepared by methods well known in the art. For example, synthesis of 3,4-diaminobenzamidine monohydrochloride is known in the art.

Compounds of Formula I in which $X^1$ is —CH—, $R^{13}$ is hydrogen, and $X^2$, $X^3$, $X^4$, $R^1$, $R^2$, $R^x$, $R^y$, and $R^z$ are as defined in the Summary of the Invention can be prepared as described in Scheme II below.

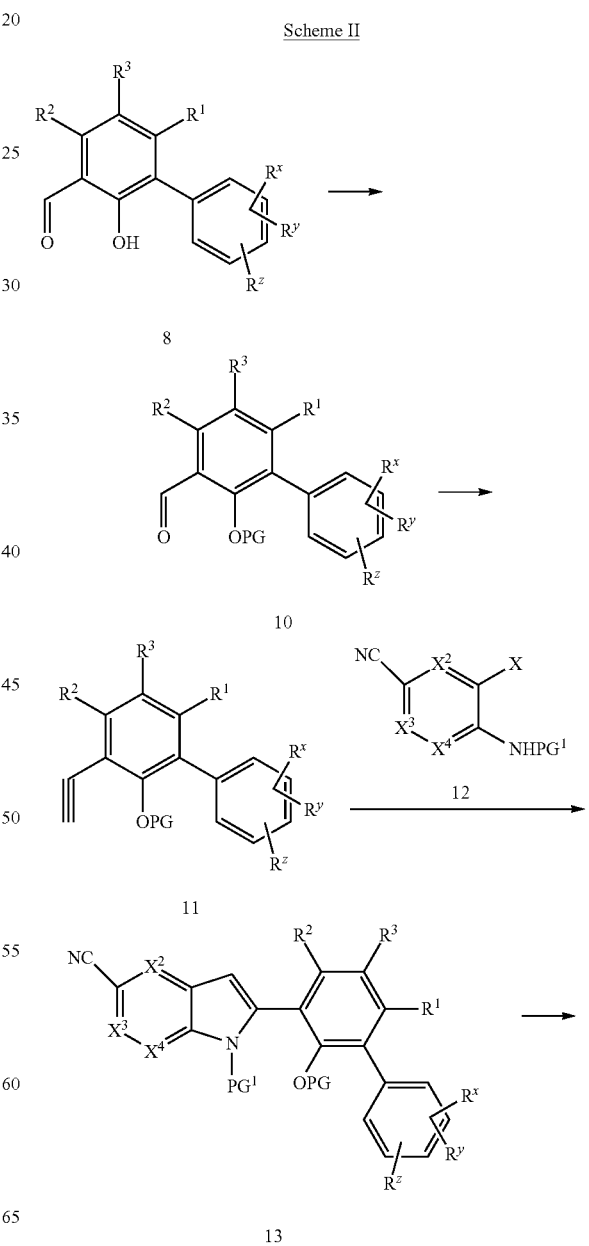

Scheme II

-continued

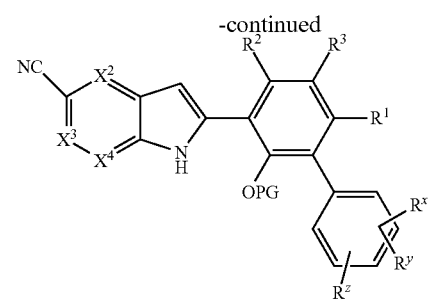

14

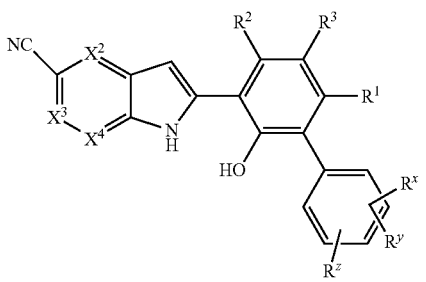

15

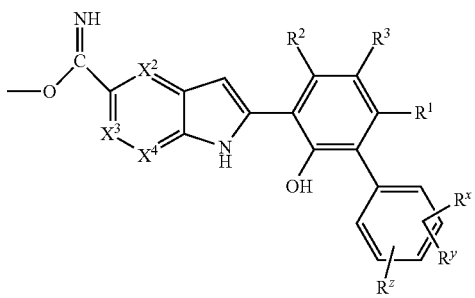

16

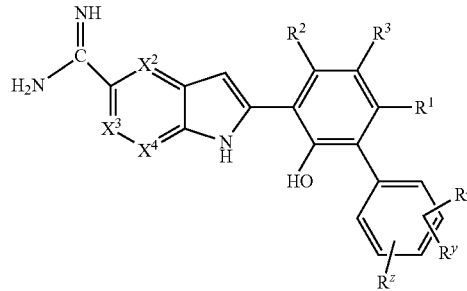

I

Protection of the hydroxy group in a compound of formula 8 with a suitable hydroxy protecting group provides a compound of formula 10. A comprehensive list of suitable hydroxy protective groups can be found in T. W. Greene, *Protective Groups in Organic Synthesis*, John Wiley & Sons, Inc. 1981, the disclosure of which is incorporated herein by reference in its entirety. Preferred hydroxy protecting group is 2-methoxyethoxymethyl. The reaction is typically carried out in the presence of a base such as diisopropylethylamine, and the like and in a halogenated organic solvent such as dichloromethane, carbon tetrachloride, chloroform, and the like.

Ethynylation of 10 utilizing a modified procedure described in Muller, S.; Liepold, B.; Roth G. J.; Bestmann H. J. *Synlett* 1996, 6, 521-522 provides a ethynylbiphenyl compound of formula 11.

Reaction of a compound of formula 11 with a cyano compound of formula 12 where $PG^1$ is a suitable nitrogen protecting group such as methylsulfonyl, tert-butoxycarbonyl, trifluoroacetyl, and the like, and X is halo, utilizing the reaction conditions described in Sakamoto, T; Kondo, Y.; Iwashita, S.; Nagano, T.; Yamanaka, H. *Chem. Pharm. Bull.* 1988, 36, 1305 provides 5-cyano-2-biphenyl-3-ylindole compound of formula 13 (where $X^1$, $X^2$, $X^3$ and $X^4$ are carbon and $PG^1$ is not hydrogen). Deprotection of the amino group in 13 provides a 5-cyano-2-biphenyl-3-yl-1H-indole compound of formula 14. The reaction conditions utilized in the deprotection step depends on the nature of the nitrogen protecting group. For example, if the protecting group is methylsulfonyl it is removed under basic hydrolysis reaction conditions. Suitable bases are aqueous sodium hydroxide, potassium hydroxide, and the like. The reaction is carried out in an alcoholic solution such as methanol, ethanol, and the like. If the protecting group is tert-butoxycarbonyl it is removed under acidic hydrolysis reaction conditions. Compounds of formula 12 are either commercially available or they can be prepared by methods well known in the art.

The hydroxy-protecting group in 14 is then removed to provide 5-cyano-2-(2-hydroxybiphenyl-3-yl)-1H-indole 15. The reaction conditions employed for the deprotection reaction depend on the nature of the hydroxy protecting group. For example, if the protecting group is 2-methoxyethoxymethyl, it is removed by treating 15 with an acid under non-aqueous reaction conditions, in a suitable alcoholic solvent.

The cyano group in compound 15 is then converted into the carbamimidoyl group by first treating 15 with hydrogen chloride gas in an anhydrous alcoholic solvent such as methanol, ethanol and the like, and then treating the resulting (5-methoxycarbonimidolyl)-2-(2-hydroxybiphenyl-3-yl)-1H-indole 16 with an inorganic base such as ammonium carbonate, and the like in an alcoholic solvent such as methanol, ethanol, or with excess ammonia to give resulting (5-carbamimidoyl)-2-(2-hydroxybiphenyl-3-yl)-1H-indole of Formula I. Alternatively, compound 15 can be converted to a compound of Formula I by first refluxing it with hydroxylamine in an alcoholic solvent such as ethanol and then treating the resulting (N-hydroxycarbamimidoyl)-2-(2-hydroxybiphenyl-3-yl)-1H-indole with acetic anhydride in acetic acid to give (N-acetoxycarbamimidoyl)-2-(2-hydroxybiphenyl-3-yl)-1H-indole. The acetoxy group is then removed under hydrogenation reaction conditions by treating (N-acetoxycarbamimidoyl)-2-(2-hydroxybiphenyl-3-yl)-1H-indole with 10% palladium in an alcoholic solvent such as methanol, ethanol, and the like.

Compounds of Formula I in which $X^1$ is —N—, $R^{13}$ is hydrogen, $R^3$ is —$CONR^7R^8$ or -(alkylene)-$CONR^9R^{10}$ where $R^7$, $R^8$, $R^9$ and $R^{10}$ are as described in the Summary of the Invention and $X^2$, $X^3$, $X^4$, $R^1$, $R^2$, $R^x$, $R^y$, $R^z$ and $R^{11}$ are as defined in the Summary of the Invention can be prepared as described in Scheme III below.

Scheme III

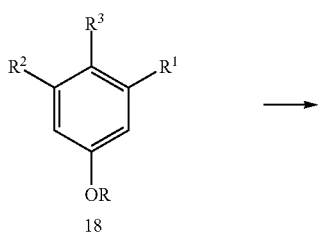

18

[R is PG or H and $R^3$ is —COOR or -alkylene-COOR]

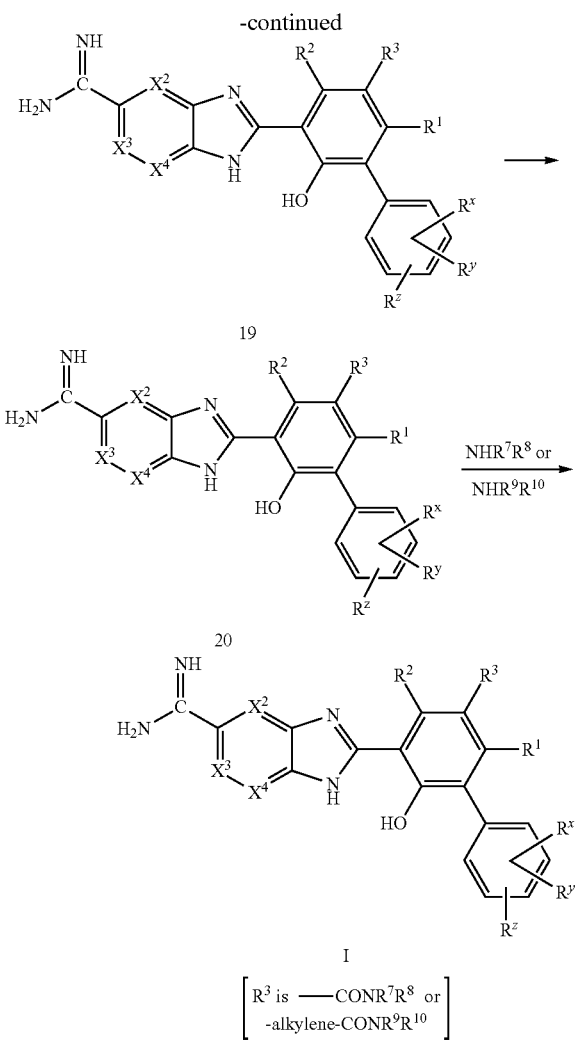

Compounds of Formula I in which $X^1$ is —N—, $R^{13}$ is hydrogen, $R^3$ is —CONR$^7$R$^8$ or -(alkylene)-CONR$^9$R$^{10}$ where $R^7$, $R^8$, $R^9$ and $R^{10}$ are as described in the Summary of the Invention and $X^2$, $X^3$, $X^4$, $R^1$, $R^2$, $R^x$, $R^y$, $R^z$ and $R^{11}$ are as defined in the Summary of the Invention can be prepared by first converting a compound of formula 18 (where R is hydroxy protecting group and $R^3$ is a —COOR' or -alkylene-COOR'group where R' is alkyl) to a compound of formula 19 (where $R^3$ is an —COOR' or -alkylene-COOR'group where R' is alkyl) as described in Scheme I. Compounds of formula 18 are either commercially available or they can be prepared by methods well known in the art. Some such methods are described in Applicant's PCT Application Publication No. WO 00/35886 the disclosure of which is incorporated herein by reference in its entirety Hydrolysis of the ester group provides a corresponding compound of formula 20 (where $R^3$ is an —COOH or -alkylene-COOH). Amination of 20 with an amine of formula NHR$^7$R$^8$ or NHR$^9$R then provides a compound of Formula I. The amination reaction is carried out reacting 20 with the amine in the presence of a suitable coupling agent e.g., benzotriazole-1-yloxytris-pyrrolidinophosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyluronium hexafluorophosphate (HATU), 1-(3-dimethylaminopropyl)-3-ethylcarbodiimide hydrochloride (EDC), or 1,3-dicyclohexylcarbodiimide (DCC), optionally in the presence of 1-hydroxybenzotriazole (HOBT), and a base such as N,N-diisopropylethylamine, triethylamine, N-methylmorpholine, and the like. The reaction is typically carried out at 20 to 30° C., preferably at about 25° C., and requires 2 to 24 h to complete. Suitable reaction solvents are inert organic solvents such as dimethylformamide, and the like.

Compounds of Formula I can be converted to other compounds of Formula I. For example, a compound of Formula I where $R^x$ is alkoxy, can be converted to corresponding compound of Formula I where $R^x$ is hydroxy by hydrolysis of the alkoxy group by a suitable dealkylating reagent such as hydrobromic acid, and the like. A compound of Formula I where $R^z$ is cyano can be converted to a corresponding compound of Formula I where $R^z$ is aminocarbonyl under hydrolysis reaction conditions. The cyano group can also be reduced to give aminomethyl group which can be treated with isocyanate or thiocyanate to give corresponding compound of Formula I where $R^z$ is ureidomethyl or thioureidomethyl respectively. A compound of Formula I where $R^{13}$ is hydrogen can be converted to a corresponding compound of Formula I where $R^{13}$ is hydroxy or alkoxy by reacting it with hydroxylamine or alkoxyamine under conditions well known in the art.

Utility

The compounds of this invention inhibit Factors VIIa, IXa, Xa, and XIa, in particular Factor VIIa, and are therefore useful as anticoagulants for the treatment or prevention of thromboembolic disorders in mammals.

Particular disease states which may be mentioned include the therapeutic and/or prophylactic treatment of venous thrombosis (e.g. DVT) and pulmonary embolism, arterial thrombosis (e.g. in myocardial infarction, unstable angina, thrombosis-based stroke and peripheral arterial thrombosis), and systemic embolism usually from the atrium during atrial fibrillation or from the left ventricle after transmural myocardial infarction, or caused by congestive heart failure; prophylaxis of reocclusion (i.e., thrombosis) after thrombolysis, percutaneous trans-luminal angioplasty (PTA) and coronary bypass operations; the prevention of rethrombosis after microsurgery and vascular surgery in general.

Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis; the therapeutic and/or prophylactic treatment of idiopathic and adult respiratory distress syndrome, pulmonary fibrosis following treatment with radiation or chemotherapy, septic shock, septicemia, inflammatory responses, which include, but are not limited to, edema, acute or chronic atherosclerosis such as coronary arterial disease and the formation of atherosclerotic plaques, cerebral arterial disease, cerebral infarction, cerebral thrombosis, cerebral embolism, peripheral arterial disease, ischaemia, angina (including unstable angina), reperfusion damage, restenosis after percutaneous trans-luminal angioplasty (PTA) and coronary artery bypass surgery.

The compounds of Formula I can also be used in the treatment of cancer or rheumatoid arthritis.

Testing

The ability of the compounds of this invention to inhibit factor VIIa and Xa can be tested in vitro and in vivo assays described in biological assays Example 1 and 2 below.

Administration and Pharmaceutical Compositions

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula I may range from approximately 0.01-50 mg per kilogram body weight of the recipient per day; preferably about 0.1-20 mg/kg/day. Thus, for administration to a 70 kg person, the dosage range would most preferably be about 7 mg to 1.4 g per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral or parenteral using a convenient daily dosage regimen, which can be adjusted according to the degree of affliction. Oral compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula I in combination with at least one pharmaceutically acceptable excipient. Acceptable excipients are non-toxic, aid administration, and do not adversely affect the therapeutic benefit of the compound of Formula I. Such excipient may be any solid, liquid, semi-solid or, in the case of an aerosol composition, gaseous excipient that is generally available to one skilled in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like.

Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of a compound of Formula I based on the total formulation, with the balance being one or more suitable pharmaceutical excipients. Preferably, the compound is present at a level of about 1-80 wt %. Representative pharmaceutical formulations containing a compound of Formula I are described below.

The compounds of Formula I can be administered alone or in combination with other compounds of Formula I or in combination with one or more other active ingredient(s). For example, a compound of Formula I can be administered in combination with another anticoagulant agent(s) independently selected from a group consisting of a thrombin inhibitor, a factor IXa, and a factor Xa inhibitor. Preferably, the thrombin inhibitor is Inogatran®, Melagatran® or prodrugs thereof which are disclosed in PCT Application Publication Nos. WO 94/29336 and WO 97/23499, the disclosures of which are incorporated herein by reference in their entirety. Factor Xa inhibitors that may be used in the combination products according to the invention include those described in *Current Opinion in Therapeutic Patents*, 1993, 1173-1179 and in international patent applications WO 00/20416, WO 00/12479, WO 00/09480, WO 00/08005, WO 99/64392, WO 99/62904, WO 99/57096, WO 99/52895, WO 99/50263, WO 99/50257, WO 99/50255, WO 99/50254, WO 99/48870, WO 99/47503, WO 99/42462, WO 99/42439, WO 99/40075, WO 99/37304, WO 99/36428, WO 99/33805, WO 99/33800, WO 99/32477, WO 99/32454, WO 99/31092, WID 99/26941, WO 99/26933, WO 99/26932, WO 99/26919, WO 99/26918, WO 99/25720, WO 99/16751, WO 99/16747, WO 99/12935, WO 99/12903, WO 99/11658, WO 99/11617, WO 99/10316, WO 99/07732, WO 9/07731, WO 99/05124, WO 99/00356, WO 99/00128, WO 99/00127, WO 99/00126, WO 9/00121, WO 98/57951, WO 98/57937, WO 98/57934, WO 98/54164, WO 98/46591, WO 98/31661, WO 98/28282, WO 98/28269, WO 98/25611, WO 98/24784, WO 98/22483, WO 98/16547, WO 98/16525, WO 98/16524, WO 98/16523, WO 98/15547, WO 98/11094, WO 98/07725, WO 98/06694, WO 98/01428, WO 7/48706, WO 97/46576, WO 97/46523, WO 97/38984, WO 97/30971, WO 97/30073, WO 97/29067, WO 97/24118, WO 97/23212, WO 97/21437, WO 97/08165, WO 97/05161, WO 96/40744, WO 96/40743, WO 96/40679, WO 96/40100, WO 96/38421, WO 96/28427, WO 96/19493, WO 96/16940, WO 95/28420, WO 94/13693, WO 00/24718, WO 99/55355, WO 99/51571, WO 99/40072, WO 99/26926, WO 98/51684, WO 97/48706, WO 97/24135, WO 97/11693, WO 00/01704, WO 00/71493, WO 00/71507, WO 00/71508, WO 00/71509, WO 00/71511, WO 00/71512, WO 00/71515, WO 00/71516, WO 00/13707, WO 00/31068, WO 00/32590, WO 00/33844, WO 00/35859, WO 00/35886, WO 00/38683, WO 00/39087, WO 00/39092, WO 00/39102, WO 00/39108, WO 00/39111, WO 00/39117, WO 00/39118, WO 00/39131, WO 00/40548, WO 00/40571, WO 00/40583, WO 00/40601, WO 00/47207, WO 00/47553, WO 00/47554, WO 00/47563, WO 00/47578, WO 00/51989, WO 00/53264, WO 00/59876, WO 00/59902, WO 00/71510, WO 00/76970, WO 00/76971, WO 00/78747, WO 01/02356, WO 01/02397, WO 01/05784, WO 01/09093, WO 01/12600, WO 01/19788, WO 01/19795, WO 01/19798, WO 93/15756, WO 94/17817, WO 95/29189, WO 96/18644, WO 96/20689, WO 96/39380, WO 97/22712, WO 97/36580, WO 97/36865, WO 97/48687, WO 98/09987, WO 98/46626, WO 98/46627, WO 98/46628, WO 98/54132, WO 99/07730, WO 99/33458, WO 99/37643 and WO 99/64446; in U.S. Pat. Nos. 6,034,093, 6,020,357, 5,994,375, 5,886,191, 5,849,519, 5,783,421, 5,731,315, 5,721,214, 5,693,641, 5,633,381, 5,612,378, 6,034,127, 5,670,479, 5,658,939, 5,658,930, 5,656,645, 5,656,600, 5,639,739, 5,741,819, 6,057,342, 6,060,491, 6,080,767, 6,087,487, 6,140,351, 6,395,731, and 5,646,165; in Japanese patent applications Nos. JP 99152269, JP 10017549, JP 10001467, JP 98017549, JP 00178243, JP 11140040, JP 12143623, JP 12204081, JP 12302765, JP 6327488 and JP 98001467; in European patent applications EP 937 723, EP 937 711, EP 874 629, EP 842 941, EP 728 758, EP 540 051, EP 419 099, EP 686 642, EP 1 016 663 and EP 529 715; and in German patent applications Nos. DE 19845153, DE 19835950, DE 19743435, DE 19829964, DE 19834751, DE 19839499, DE19900355, DE19900471 and DE 19530996, the specific and generic disclosures in all of which documents are hereby incorporated by reference.

Factor Xa inhibitors also include those disclosed in international patent applications WO 96/10022, WO 97/28129, WO 97/29104, WO 98/21188, WO 99/06371, WO 99/57099, WO 99/57112, WO 00/47573, WO 00/78749, WO 99/09027 and WO 99/57113, the specific and generic disclosures in all of which documents are hereby incorporated by reference, as well as 4-{4-[4-(5-chloroindol-2-ylsulfonyl) piperazine-1-carbonyl]phenyl}-pyridine-1-oxide and pharmaceutically acceptable derivatives thereof. Preferred Factor Xa inhibitors include antistatin, tick anticoagulant protein and those known as SQ-311 and SQ-315 (see international patent application WO 98/57951); SN-292 (see international patent application WO 98/28282); SN-429 and SN 116 (see international patent application WO 98/28269); RPR-208707 (see international patent application WO 98/25611 at Example 48); XU-817 (see international patent application WO 98/01428); SF-324 and SF-303 (see international patent application WO 97/23212); YM 60828 (see international patent application WO 96/16940 at Example 75); FACTOREX (see U.S. Pat. No. 5,783,421); SF-324 (see European patent application EP 874 629); DX9065A (see European patent application EP 540 051 at Example 39); 1-(4-carbamimidoylbenzyl)-4-(6-chloronaphthalene-2-ylsulfonyl)-piperazin-2-one (see JP 12204081 at Example 2); M55555 (see international patent application WO 99/33805 at Example 39); DPC423 (1-(3-carbamimidoylphenyl)-2-(2'-aminolsulfonyl[1, 1'-biphenyl]-4-ylaminocarbonyl)-4-bromopyrrole, see international patent application WO 98/28269); 3-(3,5-difluoro-6-[3-(4, 5dihydro-1-methylimidazol-2-yl)-phenoxy]-4-[2,3-dihydroxy-propoxy]-pyridin-2-yloxy)-4-hydroxybenzamidine (see international patent application WO 00/31068); ZK-807834 (see international patent application WO 7/29067); 1,4-diaza-4-(6-chloronaphthalene-2-ylsulfonyl)-6-(methoxymethyl)-7-oxa-1'-(pyridin-4-yl)spiro[bicyclo-[4-3.0]-nonane-8,4'-piperidine]-2-one (see international patent application WO 01/02397); (S)-1-(4-aminoquinazolin-7-yl-methyl)-4-[2-(5-chlorothien-2-yloxy)acetyl]-3-methoxymethylpiperazin-2-one (see international patent application WO 00/32590); 3-(2-[4-(2-aminosulfonyl-phenyl)benzoylphenoxy)-benzamidine (see international patent application WO 01/19788); and 4-(2-[4-(5-chloroindol-2-ylsulfonyl)-2-(pyrrolidin-1-ylcarbonylmethyl)piperazin-1-ylcarbonyl]-thiazol-5-yl)pyridine N-oxide (see Japanese patent application No. JP 12143623); as well as the compounds of Example 7 of international patent application WO 98/21188, of Examples 3 and 6 of WO 99/57113, of Example 6 of international patent application WO 00/78747, of Examples 188, 211 and 167 of U.S. Pat. No. 6,080,767, of Examples 40, 54 and 55 of international patent application WO 99/33805, of Examples 5, 6, 8, 9, 10, 11, 12, 13, 15, 16 and 17 of international patent application WO 01/05784, of Examples 6, 7, 8, 9, 10, 11, 12, 13, 14, 15, 16, 17, 22, 23, 25, 26, 28, 29, 30, 31, 32, 33, 34, 38, 39, 40, 41, 42 and 43 of international patent application WO 01/12600, and of Examples 802 and 877 of international patent application WO 00/35886. Other anticoagulant agents that can be used in the combination therapy are those disclosed in U.S. Patent Applications Publication Nos. 20020065303, 20020061842, 20020058677, 20020058657, 20020055522, 20020055469, 20020052368, 20020040144, 20020035109, 20020032223, 20020028820, 20020025963, 20020019395, 20020019394, 20020016326, 20020013314, 20020002183, 20010046974, 20010044537, 20010044536, 20010025108, 20010023292, 20010023291, 20010021775, 20010020020033, 20010018423, 20010018414, and 20010000179, which are incorporated herein by reference in their entirety.

Suitable formulations for use in administering melagatran and derivatives (including prodrugs) thereof are described in the literature, for example as described in inter alia international patent applications WO 94/29336, WO 96/14084, WO 96/16671, WO 97/23499, WO 97/39770, WO 97/45138, WO 98/16252, WO 99/27912, WO 99/27913, WO 00/12043 and WO 00/13671, the disclosures in which documents are hereby incorporated by reference.

Similarly, suitable formulations for use in administering Factor Xa inhibitors and derivatives (including prodrugs) thereof are described in the literature, for example as described in the prior art documents relating to Factor Xa inhibitors that are mentioned hereinbefore, the disclosures in which documents are hereby incorporated by reference. Otherwise, the preparation of suitable formulations, and in particular combined preparations including both melagatran/derivative and Factor Xa inhibitor/derivative may be achieved non-inventively by the skilled person using routine techniques. The amounts of melagatran, Factor Xa inhibitor, or derivative of either, in the respective formulation(s) will depend on the severity of the condition, and on the patient to be treated, as well as the compound(s) which is/are employed, but may be determined non-inventively by the skilled person.

Suitable doses of melagatran, Factor Xa inhibitors and derivatives of either, in the therapeutic and/or prophylactic treatment of mammalian, especially human, patients may be determined routinely by the medical practitioner or other skilled person, and include the respective doses discussed in the prior art documents relating to melagatran (or derivatives (including prodrugs) thereof), and to Factor Xa inhibitors, that are mentioned hereinbefore, the disclosures in which documents are hereby incorporated by reference.

EXAMPLES

The following preparations and examples are given to enable those skilled in the art to more clearly understand and to practice the present invention. They should not be considered as limiting the scope of the invention, but merely as being illustrative and representative thereof.

Synthetic Examples Reference 1

Synthesis of
2-methoxymethylether-5-fluoro-phenylboronic acid

2-Bromo-4-fluorophenol (25.0 g, 0.13 mol) was dissolved in dry dichloromethane (100 mL) and dimethoxymethane (115 mL, 1.30 mol). Phosphorus pentoxide (110.8 g, 0.39 mol) was added portion-wise to the solution such that the reaction temperature remained below 40° C. The mixture was stirred vigorously at room temperature for 2 hours and then carefully poured into 1N aqueous NaOH (50 mL). The organic layer was separated, washed with water and then brine, dried over anhydrous $MgSO_4$, filtered and concentrated to give 2-bromo-4-fluoro-1-methoxymethoxy-benzene (30.1 g) as a colorless oil.

A 500 mL round bottom flask was charged with a 1.6 M solution of n-butyllithium in hexanes (100 mL, 0.16 mol) and flushed with nitrogen. The solution was cooled to −78° C. and a solution of 2-bromo-4-fluoro-1-methoxymethoxy-benzene (30.1 g, 0.13 mol) in dry tetrahydrofuran (50 mL) was added dropwise over one hour. The mixture was stirred at −78° C. and then trimethylborate (20 mL, 0.175 mol) was added very slowly via syringe. The reaction was allowed to gradually warm to room temperature and after two hours the mixture was poured into ice. The mixture was acidified to pH 4 with 5% aqueous citric acid and extracted with ethyl acetate (×3). The combined organic extracts were washed with water and brine, dried over $MgSO_4$ and filtered. The solvent was evaporation under reduced pressure and the residue was recrystallized from hexanes give 2-methoxymethoxy-5-fluorophenyl-boronic acid (18.9 g).

Reference 2

Synthesis of tert-butyl
2-bromo-5-chloro-6-cyano-pyridin-3-yl-carbamate

2-Hydroxy-5-nitropyridine (50 g, 357 mmol) and N-chlorosuccinimide (55 g, 410 mmol) were suspended in anhydrous DMF (150 mL). The suspension was stirred at room temperature for 18 hours. The resulting homogeneous reaction mixture was diluted by the slow addition of water (750 mL), which resulted in a pale yellow precipitate. The solids were isolated via filtration and dried under high vacuum to provide 3-chloro-5-nitro-2-hydroxypyridine (59 g, 95% yield).

3-Chloro-5-nitro-2-hydroxy-pyridine (20 g) was added in small portions to thionylchloride (200 mL) under vigorous stirring. The suspension was heated to 100° C. within 1 hour, stirred at 100° C. for 1 hour and then cooled to room temperature. The solvent was removed under reduced pressure and the residue was dissolved in ethyl acetate. The solution was washed with water (3×200 mL) and the organic layer was dried over $MgSO_4$. The solvent was removed under reduced pressure to give 2,3-dichloro-5-nitropyridine (18 g) was obtained as a pale yellow solid.

A solution of 2,3-dichloro-5-nitropyridine (9.75 g) and potassium iodide (29 g) in acetic acid (120 mL, degassed with nitrogen) was heated to 100° C. for 1.5 hours under nitrogen. The brown solution was cooled to room temperature and then ethyl acetate (300 mL) added. The organic phase was separated and washed with water (2×100 mL) and dilute aqueous sodium sulfite (100 mL). Evaporation of the solvent gave crystalline 3-chloro-2-iodo-5-nitro-pyridine (13.11 g).

A suspension of copper cyanide (7 g) and 3-chloro-2-iodo-5-nitro-pyridine (7 g) in acetonitrile (200 mL) was heated to 80° C. within 1 hour and stirred at 80° C. for 5 hours. The solvent was evaporated and the residue was filtered in ethyl acetate over silicon dioxide gave 3-chloro-2-cyano-5-nitro-pyridine (4.26 g).

A solution of tin chloride (52 g) and 3-chloro-2-cyano-5-nitro-pyridine (10.3 g) was stirred in ethyl acetate (200 mL) at room temperature for 10 minutes and at 70° C. for 4 hours. The solution was cooled to room temperature and diluted with ethyl acetate (500 mL). Sodium bicarbonate (100 g) added in four portions to the mixture within 4 hours. The mixture was stirred vigorously for 20 hours. The suspension was filtered and the filtrate was washed with saturated aqueous sodium bicarbonate solution. The solvent was evaporated to give 5-amino-3-chloro-2-cyanopyridine (4.34 g) as an off-white powder.

Step (f)

Bromine (7.22 g) was added to a stirring mixture of 5-amino-3-chloro-2-cyanopyridine (4.61 g) and sodium acetate (4.81 g) in anhydrous acetic acid (150 mL) at room temperature. The mixture was stirred at 60° C. for 2 hours. The solvents and excess bromine were evaporated and the residue was recrystalliezed from ethyl acetate to give 5-amino-6-bromo-3-chloro-2-cyano-pyridine (6.23 g).

5-Amino-6-bromo-3-chloro-2-cyano-pyridine (1.6 g) was dissolved in tetrahydrofuran (5 mL) at room temperature. N,N-dimethylaminopyridine (0.5 g) followed by di-tert-butyl dicarbonate (3.78 g) in small portions were added to the solution and the mixture was stirred at room temperature for 30 minutes. The solvent was removed by evaporation and the residue was dissolved in dichloromethane (60 mL). Trifluoroacetic acid (1 g) was added to the solution and the mixture was stirred for 1 hour. The solvent was removed by evaporation and product was purified from the residue by column chromatography (EtOAc/hexanes 1/1) to give tert-butyl 2-bromo-5-chloro-6-cyano-pyridin-3-yl-carbamate (1 g). MS (obs.): 333 (M+1).

Reference 3

Synthesis of 5-cyano-2-methoxybenzeneboronic acid

3-Bromo-4-methoxybenzonitrile (3.0 g, 14.2 mmol, 1.0 eq) was dissolved in anhydrous tetrahydrofuran (10 mLs). The solution cooled at −10° C. and stirred while isopropyl-magnesium chloride (17.7 mmol, 8.8 mLs, 2.0 M in THF, 1.25 eq.) was added. The mixture was stirred for 1 hour and then trimethyl borate (1.87 g, 17.7 mmol, 2.0 mL) was added dropwise. The mixture was allowed to warm slowly to room temperature for 1 hour. The solvent was evaporated and the residue was partitioned between 5% citric acid and ethyl acetate. The organic layer was separated, washed with water and brine, dried over anhydrous magnesium sulfate and concentrated to a minimum volume under reduced pressure. The residue was recrystallized from hexanes to give 5-cyano-2-methoxybenzeneboronic acid (2.48 g, 99%) as a fluffy white powder.

Reference 4

Lithium 2-aminoethanesulfonate

Lithium hydroxide monohydrate (0.42 g, 0.10 mol) was dissolved in water (15 mL) and the solution was treated with 2-amino-ethanesulfonic acid (1.25 g, 0.10 mol). The mixture was stirred until all solids dissolved and then for an additional 30 minutes. The water solvent was evaporated off in vacuo and the resulting wet solid was heated at 70° C. under vacuum (1 Torr) overnight to give lithium 2-aminoethanesulfonate as a dry, free-flowing colorless solid.

Reference 5 tert-Butyl 6-amino-2-tert-butoxycarbonylamino-hexanoate tert-Butyl 2-amino-6-benzyloxycarbonylamino-hexanoate (1.0 g, 2.68 mmol) was dissolved in N,N-dimethylformamide (50 mL) and then triethylamine (5.35 mmol, 0.75 mL) followed by N-(tert-butoxycarbonyloxy)succinimide (0.72 g, 3.35 mmol) was added to the solution. The mixture was stirred overnight and then concentrated. The product was purified from the residue by silica gel chromatography (20% MeOH/chloroform) to give tert-butyl 6-benzyloxycarbonylamino-2-tert-butoxycarbonylamino-hexanoate. The tri-protected product was reduced on a Parr hydrogenator (50 psi) to remove the benzyloxycarbonyl protecting group. The solvents were removed to give tert-butyl 6-amino-2-tert-butoxycarbonylamino-hexanoate (0.65 g, 80%).

Reference 6

3-Bromo-N-tert-butyl-4-methoxybenzenesulfonamide

1-Bromo-2-methoxy-benzene (1.87 g, 10.0 mmol) was dissolved in chloroform (5 mL) and the solution was cooled in an ice-salt bath to −5° C. to 0° C. The cooled solution was carefully charged with chlorosulfonic acid (2.0 mL, 30.0 mmol) over 30 minutes and the mixture was allowed to warm to room temperature over 1 hour. The mixture then was poured onto chopped ice and transferred to a separatory funnel. The aqueous layer was separated and extracted (×2). The combined organic layers were dried and concentrated to give 3-bromo-4-methoxyphenylsulfonyl chloride (2.80 g, 98%).

3-Bromo-4-methoxyphenylsulfonyl chloride (2.80 g, 9.8 mmol) was dissolved in dichloromethane (30 mL) and the solution was treated with triethylamine (1.76 mL, 12.6 mmol), followed by the dropwise addition of t-butylamine (1.33 mL, 12.6 mmol). The mixture was allowed to stand for 2 hours and then was poured onto a mixture of 5% citric acid solution and dichloromethane. The organic layer was separated and the aqueous layer was extracted with dichloromethane (×2). The combined organic layers were dried and concentrated. Crystallization of the crude solid from ethyl acetate/hexane gave 3-bromo-N-tert-butyl-4-methoxybenzenesulfonamide (2.43 g, 77%).

Reference 7

Synthesis of 1-[3-bromo-4-(2-methoxyethoxymethoxy)benzyl]-3-tert-butylurea

Diisopropylethylamine (21.8 mL, 151.5 mmol) was added slowly to a magnetically stirred solution of 3-bromo-4-hydroxybenzonitrile (10 g, 50.5 mmol) and 2-methoxyethoxymethyl chloride (6.9 mL, 60.6 mmol) in dichloromethane (100 mL) and the mixture was stirred at room temperature for 30 minutes. The mixture was washed with 5% citric acid solution until the washings were acidic, dried and concentrated. Product was purified from the residue by chromatography (silica gel, 30% ethyl acetate/hexanes) gave 3-bromo-4-(2-methoxyethoxymethoxy)-benzonitrile (11.5 g).

Borane-tetrahydrofuran complex (280 mL, 1 M, 280 mmol) was added to a magnetically stirred solution of 3-bromo-4-(2-methoxyethoxymethoxy)-benzonitrile (10 g, 35 mmol) in tetrahydrofuran (20 mL) and the reaction mixture was refluxed for 30 minutes. The mixture was cooled to 0° C. and 1 N HCl was added very slowly until the pH was acidic. The tetrahydrofuran was removed by evaporation and the residual aqueous layer was washed with ethyl ether. The aqueous extract was basified with 2 N sodium hydroxide until alkaline pH and extracted with ethyl acetate. The organic layer was washed with brine, dried over anhydrous sodium sulfate and concentrated by evaporation to give 3-bromo-4-(2-methoxy-ethoxymethoxy)benzylamine (5.6 g).

tert-Butylisocyanate (2.9 mL, 25.5 mmol) followed by triethylamine (9.8 mL, 68 mmol) was added to a magnetically stirred solution of 3-bromo-4-(2-methoxyethoxymethoxy) benzyl-amine (5 g, 17 mmol) in DMF (50 mL) and the mixture was stirred at room temperature for 15 minutes. The mixture was diluted with water (10 mL) and the dilution was extracted with ethyl acetate. The organic layer was washed with brine, dried over anhydrous sodium sulfate and concentrated by evaporation. Product was purified from the residue by chromatographic (silica gel) employing 100% ethyl acetate as eluent to give 1-[3-bromo-4-(2-methoxyethoxymethoxy)benzyl]-3-tert-butylurea (5.3 g).

Reference 8

Synthesis of 3-bromo-2-hydroxybenzaldehyde

2-Bromophenol (2 g, 11.5 mmol) was dissolved in anhydrous acetonitrile (25 mL) and the solution was charged with anhydrous (<1.5% water) magnesium chloride (4.4 g, 46 mmol) and dry triethylamine (12.5 mL, 86.3 mmol). The mixture was stirred for 5 minutes and paraformaldehyde (2.8 g, 92 mmol) was added. The mixture was heated to a gentle reflux for 1 to 3 hours and then cooled. The mixture was poured onto an ether/5% citric acid mixture and the ether layer separated. The ether layer was washed with water, brine, dried over anhydrous sodium sulfate and concentrated by evaporation. Product purified from the residue by chromatography on silica gel employing 30% ethyl acetate/hexanes to give 3-bromo-2-hydroxybenzaldehyde (1.6 g).

Proceeding as in Reference 8, but substituting 4-hydroxyphenylacetonitrile (2.09 g, 15 mmol) and formaldehyde (3.6 g, 120 mmol) gave 3-formyl-4-hydroxyphenylacetonitrile (1.8 g).

Proceeding as in Reference 8, but substituting methyl 4-hydroxybenzoate (30.4 g, 0.20 mol, 1.0 eq.) and paraformaldehyde (42.0 g, 1.40 mol, 7.0 eq.), gave methyl 3-formyl-4-hydroxybenzoate (16.7 g) as a white solid.

Proceeding as in Reference 8, but substituting methyl 4-hydroxyphenylacetate (42.9 g, 0.258 mol) and paraformaldehyde (77.5 g, 2.58 mole), gave methyl 3-formyl-4-hydroxyphenyl-acetate (50.0 g, ~100%).

Proceeding as in Reference 8, but substituting methyl-3-bromo-4-hydroxyphenylacetate, gave methyl-3-formyl-4-hydroxy-5-bromophenylacetate.

Reference 9

3-bromo-5-fluoro-2-hydroxybenzaldehyde

N-bromosuccinimide (1.51 g, 8.52 mmol) was added to a magnetically stirred solution of 5-fluoro-2-hydroxybenzaldehyde (1 g, 7.1 mmol) in DMF (10 mL) and the mixture was stirred at room temperature for 5 hour. The mixture was diluted with ethyl acetate and the organic layer was washed with 5% citric acid, brine, dried over anhydrous sodium sulfate and concentrated by evaporation. Product was purified from the residue by chromatography over silica gel employing 50% ethyl acetate/hexanes to give 3-bromo-5-fluoro-2-hydroxybenzaldehyde (1.2 g).

Proceeding as in Reference 9, but substituting 3-formyl-4-hydroxyphenylacetonitrile (1 g, 6.2 mmol) and N-bromosuccinimide (1.7 g, 9.3 mmol), gave 3-bromo-5-formyl-4-hydroxyphenylacetonitrile (1.2 g).

Proceeding as in Reference 9, but substituting 5-methyl salicylaldehyde (3 g, 22 mmol) and N-bromosuccinimide (4.7 g, 26.4 mmol), gave 3-bromo-2-hydroxy-5-methylbenzaldehyde (3.6 g).

Proceeding as in Reference 9, but substituting methyl 3-formyl-4-hydroxybenzoate (12.0 g, 66.6 mmol, 1 eq.) and N-bromosuccinimide (12.45 g, 69.9 mmol, 1.05 eq.) gave methyl 3-bromo-5-formyl-4-hydroxybenzoate (12.6 g) as a white solid.

Proceeding as in Reference 9, but substituting methyl 3-formyl-4-hydroxy-phenyl-acetate (50 g, 0.258 mol) and N-bromosuccinimide (45.92 g, 0.258 mole), gave methyl 3-bromo-5-formyl-4-hydroxyphenylacetate (56.4 g, 80%) as a yellow amorphous solid.

Reference 10

Synthesis of 3-bromo-4-hydroxyphenylacetate

Methyl 4-hydroxyphenylacetate (10.5 g, 63.0 mmol) was dissolved in acetic acid (200 mL) and the solution was stirred while bromine (150 mL, 0.463 M in acetic acid, 69.5 mmol) was added over 60 minutes. The mixture was stirred overnight and then concentrated by evaporation. Product was purified from the residue over 300 g of silica gel (hexanes/ethyl acetate 5:1) to give methyl 3-bromo-4-hydroxyphenylacetate (11.9 g).

Proceeding as in Reference 14, but substituting 4-methoxyphenylacetic acid (16.6 g, 0.1 mol) amd bromine (16.0 g, 0.1 mol), gave 3-bromo-4-methoxyphenylacetic acid (24.24 g, 98%) as a yellow powder.

Reference 11

Synthesis of 3-bromo-N-butyl-5-formyl-4-methoxy-benzenesulfonamide

5-Bromo-3-formyl-4-methoxybenzoic acid (480 mg, 1.84 mmol) was dissolved in anhydrous tetrahydrofuran (20 mL) and the solution was flushed with dry nitrogen for 5 minutes. Oxalyl chloride (1.2 mL, 2.4 mmol, 1.3 eq) was added slowly to the solution while vigorous stirring and then a catalytic amount of dry dimethylformamide was added. The mixture was stirred for 1 hour and then concentrated by rotary evaporation and dried on high vacuum to give 5-bromo-3-formyl-4-methoxybenzoyl chloride (501 mg) as yellow crystals.

5-Bromo-3-formyl-4-methoxybenzoyl chloride (501 mg, 1.8 mmol) was dissolved in in dichloromethane (5 mL) and the solution was added dropwise to a vigorously stirring solution of N-butylsulfonamide (272 mg, 2.0 mmol), triethylamine (2.5 mmol) and a catalytic amount of N,N'-dimethylaminopyridine (10 mL in dichloromethane). The mixture was stirred at room temperature until the reaction was complete and concentrated under reduced pressure. The residue was partitioned between 5% citric acid and ethyl acetate. The organic layer was washed with water and brine, dried over anhydrous magnesium sulfate and the filtrate was evaporated to give 3-bromo-N-butyl-5-formyl-4-methoxy-benzenesulfonamide as a white solid (650 mg).

Reference 12

Synthesis of 3-bromo-2-(2-methoxy-ethoxymethoxy)benzaldehyde

3-Bromo-2-hydroxybenzaldehyde (1.5 g, 7.5 mmol) was dissolved in dichloromethane (25 mL) and diisopropylethylamine (2 mL, 11.3 mmol) was added to the solution. The mixture was stirred while 2-methoxyethoxymethyl chloride (0.94 mL, 8.3 mmol) was added dropwise. The mixture was stirred for 1 hour and then washed with 5% citric acid solution (5 mL) until the washings were acidic, dried and concentrated by evaporation. Product was purified from the residue by chromatography (silica gel, 30% ethyl acetate/hexanes) to give 3-bromo-2-(2-methoxy-ethoxymethoxy)benzaldehyde (1.7 g).

Proceeding as in Reference 12, but substituting 3-bromo-5-fluoro-2-hydroxybenzaldehyde, gave 3-bromo-5-fluoro-2-(2-methoxy-ethoxymethoxy)-benzaldehyde; and substituting 3-bromo-5-formyl-4-hydroxyphenylacetonitrile (1.2 g, 5 mmol) to give 3-bromo-5-formyl-4-(2-methoxy-ethoxymethoxy)-phenyl-acetonitrile (1.4 g).

Proceeding as in Reference 12, but substituting methyl 3-bromo-5-formyl-4-hydroxybenzoate (12.6 g, 48.6 mmol, 1.0 eq.) and methoxyethoxymethyl chloride (6.8 mL, 7.26 g, 58.3 mmol, 1.2 eq.), gave methyl 3-bromo-5-formyl-4-(2-methoxyethoxymethoxy)-benzoate (16.2 g) as a colorless oil which solidified upon standing.

Proceeding as in Reference 12, but substituting methyl 3-bromo-4-hydroxyphenylacetate (22.33 g, 91.14 mmol) and 2-methoxyethoxymethyl chloride (13.62 g, 12.49 mL, 0.11 mol), gave 3-bromo-4-(2-methoxyethoxymethoxy)-phenylacetate (32.67 g).

Proceeding as in Reference 12, but substituting methyl 3-bromo-5-formyl-4-hydroxyphenylacetate (27.32 g, 0.10 mole) and 2-methoxyethoxymethyl chloride (0.125 mol, 14.3 mL), gave methyl 3-bromo-5-formyl-4-(2-methoxy-ethoxymethoxy)-phenylacetate (31.4 g (87%).

Reference 13

Synthesis of 3-bromo-2-(methoxyethoxymethoxy)-5-(1-(methoxyethoxymethyl)-1H-tetrazol-5-yl)benzaldehyde A solution of 3-bromo-2-hydroxy-5-(1H-tetrazol-5-yl) benzaldehyde in dichloromethane (25 mL) was treated with diisopropylethylamine (1.2 mL, 6.4 mmol) and 2-methoxyethoxymethyl chloride (0.72 mL, 6.4 mmol) under a stream of nitrogen and the mixture was stirred at room temperature for 2 hours. Workup involved rotovaping off most of the dichloromethane, followed by usual extractive workup with ethyl acetate and 5% aqueous citric acid. Collection and drying of the organic extracts gave a regioisomeric mixtures of 3-bromo-2-(methoxyethoxymethoxy)-5-(1-(methoxyethoxymethyl)-1H-tetrazol-5-yl)benzaldehyde (0.93 g) as an oil.

Reference 14

Synthesis of methyl 4-benzyloxy-3-bromo-5-formyl-benzoate

Methyl 3-bromo-5-formyl-4-hydroxybenzoate (11.5 g, 44.39 mmol) was dissolved in acetone (100 mL) and then benzylbromide (8.35 g, 48.83 mmol) and potassium bicarbonate (6.74 g, 48.83 mmol) were added. The mixture was stirred overnight and the organic layer was washed with water. The organic layer was separated, dried over MgSO$_4$ and concentrated. Product was purified from the residue by flash silica gel chromatography to give methyl 4-benzyloxy-3-bromo-5-formyl-benzoate (10.0 g).

Reference 15

Synthesis of tert-butyl (3-bromo-benzyl)carbamate

A mixture of 3-aminomethylbromobenzene (22.11 g, 99.5 mmol), di-tert-butyl dicarbonate (26.07 g, 119.45 mmol), sodium hydroxide (8.76 g, 219 mmol) in tetrahydrofuran (75 mL) and water (100 mL) were stirred at room temperature for 30 minutes. Extraction and work-up with methylene chloride and water, followed by drying gave tert-butyl (3-bromo-benzyl)carbamate (34.9 g).

Proceeding as in Reference 15, but substituting 3-bromo-4-(2-methoxyethoxymethoxy)benzylamine (2.40 g, 8.27 mmol) and di-tert-butyl dicarbonate (3.56 g, 16.3 mmol), gave tert-butyl [3-bromo-4-(2-methoxyethoxymethoxy)-benzyl]carbamate (2.36 g).

Reference 16

Synthesis of N-acetyl-5-bromo-3-formyl-4-methoxy-benzenesulfonamide

A 100 mL round-bottom flask was charged with 5-bromo-3-formyl-4-methoxy-benzenesulfonamide (586 mg, 2.0 mmol) dissolved in dichloromethane (40 mL) and the solution was stirred vigorously while triethylamine (252 mg, 2.50 mmol) was added, followed by acetic anhydride (224 mg, 2.2 mmol) and a catalytic amount of N,N-dimethylaminopyridine. The mixture was stirred for 1 hour and then concentrated by evaporation. The residue was partitioned between 5% citric acid and ethyl acetate. The organic layer was separated, washed with water and brine and dried over anhydrous magnesium sulfate, filtered and concentrated under reduced pressure to give N-acetyl-5-bromo-3-formyl-4-methoxybenzenesulfonamide (616 mg) as a white solid.

Reference 17

Synthesis of methyl-3-bromo-4-hydroxyphenylacetate

3-Bromo-4-hydroxyphenylacetic acid (12.0 g, 0.052 mol) was dissolved in methanol and the solution was stirred at room temperature while thionyl chloride (ten drops) was added. The mixture was stirred for two hours and then concentrated under reduced pressure. The residue was taken up in saturated aqueous sodium bicarbonate and the solution extracted with diethyl ether (×3). The organic layers were collected, washed with water and brine, dried over MgSO$_4$ and concentrated in vacuo to give methyl-3-bromo-4-hydroxyphenylacetate as a golden oil (12.6 g).

Reference 18

Preparation of 3-bromo-5-formyl-4-methoxybenzenesulfonamide

3-Bromo-2-hydroxy-benzaldehyde (27 g, 134 mmol), prepared as described in N. Hofsloekken, L. Skatteboel, "Convenient Method for the ortho-Formylation of Phenols", Acta Chemica Scandinavica, 1999, v. 53, p. 258-262), was dissolved in dimethylformamide (150 mL) and then cesium carbonate (54.7 g, 170 mmol) was added to the solution portionwise. The mixture was stirred for 30 minutes and then methyl iodide (28.5 g, 201 mmol) was added. The mixture was stirred for 20 hours and poured into water. The product was extracted with ethyl ether and the organic layer was washed with water and brine, dried over magnesium sulfate and concentrated to give 3-bromo-2-methoxybenzaldehyde (28 g).

3-Bromo-2-methoxybenzaldehyde (28 g, 130 mmol) was combined with trimethylorthoformate (27.5 g, 28.6 mL, 260 mmol) in methanol (150 mL) and then chlorosulfonic acid (0.5 mL) was added dropwise to the mixture. The mixture was stirred for 3 hours and then concentrated by rotoevaporation. The residue was partitioned between ethyl ether and 5% aqueous sodium bicarbonate and the organic layer was separated, washed with water and brine, dried over sodium sulfate and concentrated to give 1-bromo-3-dimethoxymethyl-2-methoxybenzene (27.5 g).

1-Bromo-3-dimethoxymethyl-2-methoxybenzene (9 g, 35 mmol) was dissolved in methylene chloride (3 mL) and the solution was added dropwise to a 0° C., vigorous stirring solution of chlorosulfonic acid (50 mL). The mixture then was stirred for 3 hours at 0° C. and let stand for 20 hours at room temperature. The reaction was quenched by pouring the mixture portionwise onto ice (1 kg). The product was extracted with ethyl ether and the organic layer was washed with cold water (×3) and brine, dried over sodium sulfate, filtered and treated with a stream of gaseous ammonia. Product was purified by flash silica column using hexanes/ethyl acetate mixture (7:3) as an eluent to give 3-bromo-5-formyl-4-methoxybenzenesulfonamide (3.2 g).

Reference 17

Synthesis of N-tert-butyl-3-bromobenzenesulfonamide tert-Butylamine (3.14 g, 3.0 mmol, 1.1 eq) and triethylamine (5.94 g, 58.6 mmol, 1.5 eq.) were dissolved in dichloromethane (20 mL) and stirred at room temperature while 3-bromobenzenesulfonyl chloride (10.0 g, 39.1 mmol) was added slowly. The mixture was stirred for 1 hour and then concentrated by evaporation under reduced pressure. The residue was taken up in 5% citric acid and ethyl acetate. The organic layer is washed repeatedly with brine and water, dried over anhydrous magnesium sulfate and concentrated to give N-tert-butyl-3-bromobenzenesulfonamide (10.94 g) as a white powder.

Reference 18

Synthesis of 2-(2-methoxyethoxymethoxy)-3-(4,4,5,5-tetramethyl-[1,3,2]dioxaborolan-2-yl)-benzaldehyde Bispinacolato diboron (3.3 g, 12.8 mmol) and potassium acetate (3.2 g, 32.1 mmol) was added to a stirring solution of 3-bromo-2-(2-methoxyethoxymethoxy)benzaldehyde (3.1 g, 10.7 mmol) in anhydrous dioxane (100 mL) and the mixture was heated at 90° C. for 5 minutes. The mixture was flushed with nitrogen and then dichloro[1,1'-bix(diphenylphosphino) ferrocene]Palladium (II) dichloromethane adduct (0.218 g, 0.27 mmol) was added and the reaction was refluxed for 7 to 8 hours. The mixture was cooled to room temperature and then diluted with ethyl acetate. The organic layer was washed with 5% citric acid, brine, dried over anhydrous sodium sulfate and concentrated by evaporation. Product was purified from the residue by chromatography (silica gel) with 100% ethyl acetate to give 2-(2-methoxyethoxymethoxy)-3-(4,4,5,5-tetramethyl-[1,3,2]dioxaborolan-2-yl)-benzaldehyde (40% yield).

Proceeding as in Reference 18, but substituting 3-bromo-5-fluoro-2-(2-methoxy-ethoxymethoxy)-benzaldehyde, gave 5-fluoro-2-(2-methoxy-ethoxymethoxy)-3-(4,4,5,5-tetramethyl-[1,3,2]dioxaborolan-2-yl)-benzaldehyde.

Proceeding as in Reference 18, but substituting 3-bromo-5-formyl-4-(2-methoxy-ethoxymethoxy)-phenyl-acetonitrile, gave [3-formyl-4-(2-methoxy-ethoxymethoxy)-5-(4,4,5,5-tetramethyl-[1,3,2]dioxaborolan-2-yl)-phenyl]-acetonitrile.

Proceeding as in Reference 18, but substituting N-tert-butyl-3-bromobenzenesulfonamide (4.4 g, 15.1 mmol) and bispinacolato diboron (5.0 g, 19.7 mmol), gaves N-tert-butyl-3-(4,4,5,5-tetramethyl-[1,3,2]dioxaborolan-2-yl)-benzenesulfonamide (5.31 g) as peach colored crystals.

Proceeding as in Reference 18, but substituting 3-bromo-4-methoxybenzonitrile (4.77 g, 22.5 mmol) and bis(pinacolato)diboron (6.85 g, 27.0 mmol) gave 4-methoxy-3-(4,4,5,5-tetramethyl-[1,3,2]dioxaborolan-2-yl)-benzonitrile.

Proceeding as in Reference 18, but substituting methyl 3-bromo-5-formyl-4-(2-methoxyethoxymethoxy)-phenylacetate (5.0 g, 13.8 mmol) and bis(pinacolato)diboron (4.22 g) gave methyl 3-formyl-4-(2-methoxyethoxy-methoxy)-5-(4,4,5,5-tetramethyl[1,3,2]dioxaborolan-2-yl)phenylacetate and methyl 5-formyl-4-(2-methoxyethoxymethoxy)-phenylacetate in a 2:1 ratio.

Proceeding as in Reference 18, but substituting 3-bromo-4-methoxyethoxy-methoxybenzonitrile (5.9 g, 20.33 mmol) and bis(pinacolato)diboron (6.2 g, 24.4 mmol), gave 4-methoxyethoxymethoxy-3-(4,4,5,5-tetramethyl-[1,3,2]dioxaborolan-2-yl)benzonitrile as a crude brown oil.

Reference 19

Synthesis of 1-tert-butyl-3-[3'-formyl-6,2'-bis-(2-methoxyethoxymethoxy)-biphenyl-3-ylmethyl]-urea A 2 M solution of potassium carbonate (2.1 mL) was added to a magnetically stirred mixture of 1-[3-bromo-4-(2-methoxyethoxymethoxy)benzyl]-3-tert-butylurea (1.4 g, 4.1 mmol), prepared as in Reference 11, and 2-(2-methoxyethoxymethoxy)-3-(4,4,5,5-tetramethyl-[1,3,2]dioxaborolan-2-yl)-benzaldehyde (42 mL, 0.1 mM in toluene, 4.2 mmol), prepared as in Reference 15. The mixture was flushed with nitrogen and then tetrakis(triphenylphosphine)palladium(0) (118 mg, 0.1025 mmol) was added. The mixture was refluxed for 7 hours, cooled and then poured into a mixture of ethyl acetate and 5% citric acid. The organic phase was separated and the aqueous phase was extracted twice more with ethyl acetate. The combined organic phase was dried and concentrated by evaporation. Product was purified from the residue by chromatography on silica gel utilizing 100% ethyl acetate to give 1-tert-butyl-3-[3'-formyl-6,2'-bis-(2-methoxyethoxymethoxy)-biphenyl-3-ylmethyl]-urea (1.2 g).

Proceeding as in Reference 19, but substituting 1-[3-bromo-4-(2-ethoxyethoxymethoxy)benzyl]-3-tert-butylurea (1.0 g, 2.9 mmol) and 5-fluoro-2-(2-methoxy-ethoxymethoxy)-3-(4,4,5,5-tetramethyl-[1,3,2]dioxaborolan-2-yl)-benzaldehyde (29 mL, 0.1 mM in toluene, 2.9 mmol) gave 1-tert-butyl-3-[5'-fluoro-3'-formyl-6,2'-bis-(2-methoxyethoxymethoxy)biphenyl-3-ylmethyl]-urea (0.854 g).

Proceeding as in Reference 19, but substituting 3-bromo-2-hydroxy-5-methylbenzaldehyde (0.60 g, 2.5 mmol) and N-tert-butyl-3-(4,4,5,5-tetramethyl-[1,3,2]dioxaborolan-2-yl)-benzenesulfonamide (0.846 g, 2.5 mmol), gave N-tert-butyl-3'-formyl-2'-(2-methoxyethoxymethoxy)-5'-methyl-biphenyl-3-sulfonamide (0.87 g)

Proceeding as in Reference 19, but substituting methyl 3-bromo-5-formyl-4-(2-methoxyethoxymethoxy)-benzoate (2.00 g, 5.76 mmol, 1.0 eq.) and N-tert-butyl-3-(4,4,5,5-tetramethyl-[1,3,2]dioxaborolan-2-yl)benzenesulfonamide (1.95 g, 5.76 mmol, 1.0 eq.), gave methyl 3'-tert-butylsulfamoyl-5-formyl-6-(2-methoxyethoxymethoxy)-biphenyl-3-carboxylate (2.16 g) as a yellow gum.

Proceeding as in Reference 19, but substituting 4-benzyloxy-3-bromo-5-formyl-benzoic acid methyl ester (1.0 g, 2.71 mmol) and 5-fluoro-2-methoxyphenyl boronic acid (0.691 g, 4.16 mmol), gave 6-benzyloxy-5'-fluoro-5-formyl-2'-methoxybiphenyl-3-carboxylic acid methyl ester (0.620 g).

Proceeding as in Reference 19, but substituting 3-bromo-4-(2-methoxyethoxymethoxy)phenylacetate (2.43 g, 7.28 mmol) and 2-(2-methoxyethoxymethoxy)-3-(4,4,5,5-tetramethyl-[1,3,2]dioxaborolan-2-yl)benzaldehyde in toluene (7.28 mmol, 0.1 M, 73 mL), gave methyl [3'-formyl-6,2'-bis(2-methoxyethoxymethoxy)biphenyl-3-yl]acetate (2.42 g).

Proceeding as in Reference 19, but substituting 3-bromo-N-tert-butyl-4-methoxybenzenesulfonamide (1.45 g, 4.5 mmol) and methyl 3-formyl-4-(2-methoxyethoxy-methoxy)-5-(4,4,5,5-tetramethyl[1,3,2]dioxaborolan-2-yl)-phenylacetate, gave [5'-tert-butylsulfamoyl-5-formyl-2'-methoxy-6-(2-methoxyethoxymethoxy)biphenyl-3-yl]acetate (1.56 g, 77%). LCMS: Calcd 451.53; Obsd (M+23)=474.0, (MH−)=450.1.

Proceeding as in Reference 19, but substituting 3-bromo-N-tert-butyl-4-methoxybenzenesulfonamide and methyl 3-formyl-4-(2-methoxyethoxy-methoxy)-5-(4,4,5,5-tetramethyl[1,3,2]dioxaborolan-2-yl)-benzoate, gave methyl 6-benzyloxy-5'-tert-butylsulfamoyl-5-formyl-2'-methoxy-biphenyl-3-carboxylate.

Proceeding as in Reference 19, but substituting tert-butyl (3-bromo-benzyl)-carbamate (0.9 g, 3.2 mmol) and 4-methoxy-3-(4,4,5,5-tetramethyl-[1,3,2]dioxaborolan-2-yl)-benzonitrile (0.9 g, 3.5 mmol), gave tert-butyl (5'-cyano-2'-methoxybiphenyl-3-ylmethyl)carbamate (0.73 g, 68%) as white foam.

Proceeding as in Reference 19, but substituting 3-bromo-2-(methoxyethoxymethoxy)-5-[1-(methoxyethoxymethyl)-1H-tetrazol-5-yl]benzaldehyde (0.93 g, 2.09 mmol) and 4-methoxyethoxymethoxy-3-(4,4,5,5-tetramethyl-[1,3,2]dioxaborolan-2-yl)benzonitrile (1.04 g, 3.14 mmol), gave a regioisomeric mixture of 3'-formyl-6,2'-(methoxyethoxymethoxy)-5'-(1-methoxyethoxymethyl-1H-tetrazol-5-yl)biphenyl-3-ylcarbonitrile (0.3 g).

Proceeding as in Reference 19, but substituting N-acetyl-3-bromo-5-formyl-4-methoxy-benzenesulfonamide (335 mg, 1.0 mmol) and N-tert-butyl-3-(4,4,5,5-tetramethyl-[1,3,2]dioxaborolan-2-yl)benzenesulfonamide (373 mg, 1.1 mmol), gave N-acetyl-N'-tert-butyl-5-formyl-6-methoxy-biphenyl-3,3'-disulfonamide (242 mg) as a pale yellow oil.

Proceeding as in Reference 19, but substituting 3-bromo-N-butyl-5-formyl-4-methoxy-benzenesulfonamide (0.65 g, 1.72 mmol) and N-tert-butyl-3-(4,4,5,5-tetramethyl-[1,3,2]dioxaborolan-2-yl)benzenesulfonamide (0.64 g, 1.90 mmol, 1.1 eq.), gave N-butyl-N'-tert-butyl-5-formyl-6-methoxy-biphenyl-3,3'-disulfonamide (0.74 g) as on orange oil.

Proceeding as in Reference 19, but substituting 2-bromo-6-(2-methoxy-ethoxymethoxy)-benzaldehyde provided 3'-formyl-4'-(methoxyethoxymethoxy)-N-tert-butyl-biphenylsulfonamide.

Proceeding as in Reference 19, but substituting 3-bromo-5-formyl-4-methoxy-benzenesulfonamide (0.9 g, 3.1 mmol)

and 2-methoxybenzene boronic acid (0.51 g, 3.37 mmol), gave 5-formyl-6,2'-dimethoxy-biphenyl-3-sulfonamide (0.75 g).

Proceeding as in Reference 19, but substituting 3-bromo-5-formyl-4-methoxy-benzenesulfonamide and 3-nitrobenzene boronic acid, gave 5-formyl-6-methoxy-3'-nitro-biphenyl-3-sulfonamide.

Proceeding as in Reference 19, but substituting 3-bromo-5-formyl-4-methoxy-benzenesulfonamide and 3-chlorobenzene boronic acid, gave 3'-chloro-5-formyl-6-methoxy-biphenyl-3-sulfonamide.

Proceeding as in Reference 19, but substituting 3-bromo-5-formyl-4-methoxy-benzenesulfonamide and 3-aminobenzene boronic acid, gave 3'-amino-5-formyl-6-methoxy-biphenyl-3-sulfonamide.

Proceeding as in Reference 19, but substituting 3-bromo-5-formyl-4-methoxy-benzenesulfonamide and 3-ureidobenzene boronic acid, gave 5-formyl-6-methoxy-3'-ureido-biphenyl-3-sulfonamide.

Proceeding as in Reference 19, but substituting 3-bromo-5-formyl-4-methoxy-benzenesulfonamide and 3-methoxybenzene boronic acid, gave 5-formyl-3',6-dimethoxy-biphenyl-3-sulfonic acid amide.

Proceeding as in Reference 19, but substituting 3-bromo-5-formyl-4-methoxy-benzenesulfonamide and 3-chlorobenzene boronic acid, gave 3'-chloro-5-formyl-6-methoxy-biphenyl-3-sulfonamide.

Proceeding as in Reference 19, but substituting 3-bromo-5-formyl-4-methoxy-benzenesulfonamide and benzene boronic acid, gave 5-formyl-6-methoxy-biphenyl-3-sulfonic acid amide.

Proceeding as in Reference 19, but substituting 3-bromo-5-formyl-4-methoxy-benzenesulfonamide and 5-cyano-2-methoxy-benzeneboronic acid, gave 5'-cyano-5-formyl-6,2'-dimethoxybiphenyl-3-sulfonamide.

Proceeding as in Reference 19, but substituting methyl-3-formyl-4-hydroxy-5-bromophenylacetate (2.47 g, 9.0 mmol) and 2-methoxymethoxy-5-fluorophenylboronic acid (2.0 g, 10.0 mmol), gave methyl 5'-fluoro-5-formyl-6-hydroxy-2'-methoxymethoxy-biphenyl-3-yl)-acetate (2.2 g, 70%) as a yellow oil which crystallized overnight.

Proceeding as in Reference 19, but substituting tert-butyl [3-bromo-4-(2-methoxyethoxymethoxy)-benzyl]carbamate (2.3 g, 5.9 mmol) and 2-(2-methoxyethoxymethoxy)-3-(4,4,5,5-tetramethyl-[1,3,2]dioxaborolan-2-yl)-benzaldehyde (60 mL, 0.1 M in toluene), gave tert-butyl [3'-formyl-6,2'-bis(2-methoxyethoxymethoxy)biphenyl-3-ylmethyl]carbamate (2.96 g).

Reference 20

Synthesis of 1-tert-butyl-3-[3'-formyl-2'-hydroxy-5'-(1H-tetrazol-5-yl)-biphenyl-3-ylmethyl]urea tert-Butyl (5'-cyano-2'-methoxy-biphenyl-3-yl-methyl)-carbamate (0.73 g, 2.16 mmol), prepared as in Reference 19, and azidotributyltin (0.9 mL, 3.2 mmol) was dissolved in toluene (5 mL) and the solution was refluxed for 14 hours. The mixture cooled to room temperature and then workup with ethyl acetate and 1N HCl gave a slurry. The slurry was dried by rotovap and then triturated with hexanes. The solids were collected by filtration and treated with hydrobromic acid (48% aqueous, 15 mL). The mixture was refluxed for 14 hours at 120° C. and then diluted with water (50 mL). The dilution was dried by lyophilization to give 3'-aminomethyl-5-(1H-tetrazol-5-yl)-biphenyl-2-ol (0.4 g).

3'-aminomethyl-5-(1H-tetrazol-5-yl)-biphenyl-2-ol (0.31 g, 1.16 mmol) was dissolved in dimethylformamide (10 mL) and the solution was treated with triethylamine (0.8 mL, 5.8 mmol) and tert-butylisocyanate (0.14 mL, 1.27 mmol). The mixture was stirred at room temperature for 2 hours. Workup with ethyl acetate and water, followed by drying afforded 0.56 g (quant.) of the crude 1-tert-butyl-3-[2'-hydroxy-5'-(1H-tetrazol-5-yl)-biphenyl-3-ylmethyl]-urea.

1-tert-Butyl-3-[2'-hydroxy-5'-(1H-tetrazol-5-yl)-biphenyl-3-ylmethyl]-urea (0.56 g, 1.5 mmol) was dissolved in a mixture of chloroform (0.2 mL, 3 mmol) and sodium hydroxide (10% aqueous, 5 mL, 12 mmol) and the mixture was refluxed for 5 days. The mixture was worked up with 1N hydrochloric acid and ethyl acetate. Some solids precipitated out of solution and were filtered and dried. The organic layer from the extraction was dried and combined with the solids above gives 1-tert-butyl-3-[3'-formyl-2'-hydroxy-5'-(1H-tetrazol-5-yl)-biphenyl-3-ylmethyl]-urea as a 3:1 mixture of starting material to product.

Reference 21

Synthesis of N-(3-Phenylpropionyl)-5-formyl-6,2'-dimethoxy-biphenyl-sulfonamide

5-Formyl-6,2'-dimethoxy-biphenyl-3-sulfonamide (0.32 g, 1 mmol), prepared as in Reference 19, was dissolved along with triethylamine (0.125 g, 1.25 mmol) and 4-dimethylaminopyridine (0.012 g, 0.1 mmol) in methylene chloride (30 mL) and then 3-phenylpropionyl chloride (0.2 g, 1.15 mmol) was added dropwise to the solution. The mixture was stirred for 12 hours and concentrated by rotoevaporation in vacuum. The residue was partitioned between ethyl acetate and 5% aqueous citric acid and the organic layer was separated washed with water and brine, dried over magnesium sulfate and then concentrated in vacuum to give N-(3-phenylpropionyl)-5-formyl-6,2'-dimethoxy-biphenyl-sulfonamide (0.4 g).

Proceeding as in Reference 21, but substituting 3'-amino-5-formyl-6-methoxy-biphenyl-3-sulfonamide and 3-phenylpropionyl chloride, gave N-(3-phenylpropionyl)-3'-amino-5-formyl-6-methoxy-biphenyl-3-sulfonamide.

Proceeding as in Reference 21, but substituting 5-formyl-6-methoxy-3'-nitro-biphenyl-3-sulfonamide and acetyl chloride, gave N-acetyl-5-formyl-6-methoxy-3'-nitro-biphenyl-3-sulfonamide.

Proceeding as in Reference 21, but substituting 3'-amino-5-formyl-6-methoxy-biphenyl-3-sulfonamide and acetyl chloride, gave N-acetyl-3'-amino-5-formyl-6-methoxy-biphenyl-3-sulfonamide.

Proceeding as in Reference 21, but substituting 5-formyl-6-methoxy-3'-nitro-biphenyl-3-sulfonamide and benzoyl chloride, gave N-benzoyl-5-formyl-6-methoxy-3'-nitro-biphenyl-3-sulfonamide.

Proceeding as in Reference 21, but substituting 5-formyl-6-methoxy-3'-nitro-biphenyl-3-sulfonamide and 4-phenyl-butyryl chloride, gave 5-formyl-6-methoxy-3'-nitro-N-(4-phenylbutyryl)-biphenyl-3-sulfonamide.

Proceeding as in Reference 21, but substituting 5-formyl-6-methoxy-3'-nitro-biphenyl-3-sulfonamide and 2-phenylacetyl chloride, gave 5-formyl-6-methoxy-3'-nitro-N-(2-phenylacetyl)-biphenyl-3-sulfonamide.

Proceeding as in Reference 21, but substituting 3'-amino-5-formyl-6-methoxy-biphenyl-3-sulfonamide and 4-phenylbutyryl chloride, gave 3'-amino-5-formyl-6-methoxy-N-(4-phenylbutyryl)-biphenyl-3-sulfonamide.

Proceeding as in Reference 21, but substituting 5-formyl-6-methoxy-3'-nitro-biphenyl-3-sulfonamide and 3-(3,4-dichlorophenyl)-propanoyl chloride, gave N-[3-(3,4-dichlorophenyl)-propanoyl]-5-formyl-6-methoxy-3'-nitro-biphenyl-3-sulfonamide.

Proceeding as in Reference 21, but substituting 3'-amino-5-formyl-6-methoxy-biphenyl-3-sulfonamide and benzoyl chloride, gave N-benzoyl-3'-amino-5-formyl-6-methoxy-biphenyl-3-sulfonamide.

Proceeding as in Reference 21, but substituting 5-formyl-6-methoxy-3'-ureido-biphenyl-3-sulfonamide and 2-phenylacetyl chloride, gave 5-formyl-6-methoxy-N-(2-phenylacetyl)-3'-ureido-biphenyl-3-sulfonamide.

Proceeding as in Reference 21, but substituting 5-formyl-6,2'-dimethoxy-biphenyl-3-sulfonamide and 3-phenylpropionyl chloride, gave 5-formyl-6,2'-dimethoxy-N-(3-phenylpropionyl)-biphenyl-3-sulfonamide.

Proceeding as in Reference 21, but substituting 3'-chloro-5-formyl-6-methoxy-biphenyl-3-sulfonamide and 3-phenylpropanoyl chloride, gave 3'-chloro-5-formyl-6-methoxy-N-(3-phenylpropanoyl)-biphenyl-3-sulfonamide.

Proceeding as in Reference 21, but substituting 5-formyl-6-methoxy-biphenyl-3-sulfonamide and 3-phenyl-propanoyl chloride, gave 5-formyl-6-methoxy-N-(3-phenyl-propanoyl)-biphenyl-3-sulfonamide.

Proceeding as in Reference 21, but substituting 5-formyl-6-methoxy-3'-nitro-biphenyl-3-sulfonamide and 3-pyridin-3-ylpropanoyl chloride, gave 5-formyl-6-methoxy-3'-nitro-N-(3-pyridin-3-ylpropanoyl)-biphenyl-3-sulfonamide.

Proceeding as in Reference 21, but substituting 3'-amino-5-formyl-6-methoxy-biphenyl-3-sulfonamide and 3-pyridin-3-ylpropanoyl chloride, gave 3'-amino-5-formyl-6-methoxy-N-(3-pyridin-3-ylpropanoyl)-biphenyl-3-sulfonamide.

Proceeding as in Reference 21, but substituting 5-formyl-6-methoxy-3'-ureido-biphenyl-3-sulfonamide and 3-pyridin-3-ylpropanoyl chloride, gave 5-formyl-6-methoxy-N-(3-pyridin-3-ylpropanoyl)-3'-ureido-biphenyl-3-sulfonamide.

Proceeding as in Reference 21, but substituting 3'-amino-5-formyl-6-methoxy-biphenyl-3-sulfonamide and 3-piperidin-3-ylpropanoyl chloride, gave 3'-amino-5-formyl-6-methoxy-N-(3-piperidin-3-ylpropanoyl)-biphenyl-3-sulfonamide.

Reference 22

Synthesis of N-(3-phenylpropionyl)-5-formyl-6,2'-dihydroxy-biphenyl-3-sulfonamide N-(3-Phenylpropionyl)-5-formyl-6,2'-dimethoxy-biphenyl-sulfonamide (0.4 g, 0.88 mmol) was dissolved in methylene chloride (5 mL) and the solution was stirred while a boron tribromide (2 mL, 1 M in methylenechloride, 2 mmol) was added. The mixture was stirred for 36 hours and then concentrated in vacuum. The residue was dissolved in ethyl acetate and the solution was shaken with 5% aqueous sodium bicarbonate (10 mL). The mixture was acidified to pH 3 with 5% aqueous citric acid. The organic layer was separated, washed with water and brine, dried over sodium sulfate and concentrated in vacuum to a minimal volume. The residue was passed through short silica column, using hexanes/ethyl acetate (1:1) to give N-(3-phenylpropionyl)-5-formyl-6,2'-dihydroxy-biphenyl-3-sulfonamide (0.21 g, 53%). MS. found (M−H) 424.1, (M+H) 426.2, calc 425.09.

Proceeding as in Reference 22, but substituting 3-bromo-4-methoxyphenylacetic acid (14.0 g, 0.057 mol) and boron tribromide (63 mL, 1M in dichloromethane, 0.063 mol), gave 3-bromo-4-hydroxyphenylacetic acid (12 g).

Reference 23

[5-(5-carbamimidoyl-1H-benzoimidazol-2-yl)-6,2'-dihydroxy-5'-sulfamoylbiphenyl-3-yl]acetic acid Methyl [5'-tert-butylsulfamoyl-5-formyl-2'-methoxy-6-(2-methoxyethoxymethoxy)biphenyl-3-yl]acetate (0.496 g, 1.1 mmol), prepared as in Reference 8, was dissolved in methanol (20 mL) and the solution was charged with 3,4-diaminobenzamidine-HCl (1.25 mmol, 0.23 g) and 1,4-benzoquinone (1.25 mmol, 0.135 g). The mixture was refluxed for 2 hours and then concentrated by evaporation. This residue was taken up in trifluoroacetic acid (10 mL) and the mixture was stirred for 1 hour. Evaporation and further pumping down yielded a purple amorphous residue. Pyridine hydrochloride (5.0 g) was added and the reaction mixture was heated at 180° C. for 30 minutes. The mixture was cooled and a resulting solid was dissolved in 20 mL of preparative hplc sample solvent (20% acetonitrile/20 mmol HCl). The product was purified by preparative hplc (C-18, 2,2,25 acetonitrile). The fractions containing the pure product were collected and lyophilized to give [5-(5-carbamimidoyl-1H-benzoimidazol-2-yl)-6,2'-dihydroxy-5'-sulfamoylbiphenyl-3-yl]acetic acid (0.31 g, 59%). LCMS: Calcd 481.49; Obsd (MH+)=482.0, (MH−)=480.2. NMR (DMSO-$d_6$) d 3.621 (s, 2H), 7.07 (d, J=8 Hz, 1H), 7.15 (br s, 2H), 7.27 (d, J=2 Hz, 1H), 7.63 (d, J=2 Hz, 1H), 7.65 (m, 2H), 7.73 (d of d, J=2, J=8 Hz, 1H), 7.83 (d, J=8 Hz, 1H), 8.08 (d, J=2 Hz, 1H), 8.17 (s, 1H), 9.10, 9.39 (2s, 4H).

Proceeding as in Reference 23, but substituting 3'-tert-butylsulfamoyl-5-formyl-6-(2-methoxyethoxymethoxy)-biphenyl-3-carboxylic acid methyl ester (1.64 g, 3.42 mmol, 1.0 eq.) and 3,4-diamino-benzamidine hydrochloride (638 mg, 3.42 mmol, 1.0 eq.), gave 5-(5-carbamimidoyl-1H-benzoimidazol-2-yl)-6-hydroxy-3'-sulfamoyl-biphenyl-3-carboxylic acid hydrochloride (650 mg) as a brown solid.

Proceeding as in Reference 23, but substituting 6-benzyloxy-5'-fluoro-5-formyl-2'-methoxybiphenyl-3-carboxylic acid methyl ester (1.3 g, 3.30 mmol) and 3,4-diaminobenzamidine hydrochloride (0.739 g, 3.96 mmol), gave 5-(5-carbamimidoyl-1H-benzoimidazol-2-yl)-5'-fluoro-6,2'-dihydroxy-biphenyl-3-carboxylic acid (0.780 g).

Proceeding as in Reference 23, but substituting methyl 5'-fluoro-5-formyl-6-hydroxy-2'-methoxymethoxy-biphenyl-3-yl)-acetate (400 mg, 1.1 mmol) and 3,4-diaminobenzamidine hydrochloride (235 mg, 1.2 mmol), gave 3-(5-carbamimidoyl-1H-benzoimidazol-2-yl)-5'-fluoro-6,2'-dihydroxy-biphenyl-2-yl-acetic acid (201 mg, 40%).

Example 1

Synthesis of 2-(2,2'-dihydroxy-5'-ureidomethylbiphenyl-3-yl)-1H-benzoimidazole-5-carboxamidine hydrochloride (Compound 10)

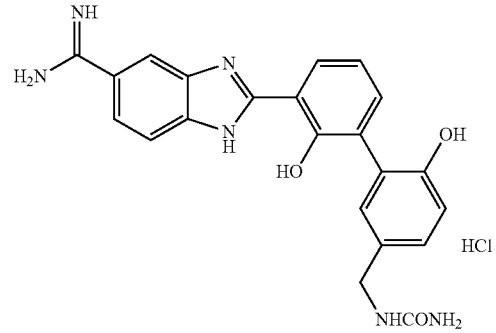

1-tert-Butyl-3-[3'-formyl-6,2'-bis-(2-methoxyethoxymethoxy)-biphenyl-3-ylmethyl]-urea (0.6 g, 1.15 mmol), prepared as in Reference 19, diaminobenzamidine hydrochloride (0.3 g, 1.6 mmol) and 1,4-benzoquinone (0.124 g, 1.15 mmol) were combined in methanol (15 mL) and the mixture was heated at 60° C. and stirred for 2 hours. The mixture was cooled to room temperature and the solvent was removed by evaporation to yield 2-[5'-(3-tert-butylureidomethyl)-2,2'-bis-(2-methoxyethoxymethoxy)-biphenyl-3-yl]-1H-benzoimidazole-5-carboxamidine.

2-[5'-(3-tert-Butylureidomethyl)-(2,2'-bis-(2-methoxyethoxymethoxy)-biphenyl-3-yl]-1H-benzoimidazole-5-carboxamidine was dissolved in 4 M hydrogen chloride in dioxane (4 mL) and the solution was a stirred at room temperature for 1 hour. Solvent was removed by evaporation and the residue was dissolved in neat trifluoroacetic acid (5 mL). The solution was stirred at room temperature for 8 hours and then concentrated by evaporation. Product was purified from the residue by reverse preparative HPLC (acetonitrile/HCl/water) to give 2-(2,2'-dihydroxy-5'-ureidomethylbiphenyl-3-yl)-1H-benzoimidazole-5-carboxamidine hydrochloride (33 mg). MS LCMS Q$^+$ 417.439 (M+1) (calc.), Q$^-$ 415.439 (M−1) (calc.), (obs.); Q$^+$ 417.3 (M+1), Q$^-$ 415.3 (M−1). $^1$H-NMR (d$_6$-DMSO) δ ppm: 4.03 (2H, s), 6.78 (1H, d, J=8 Hz), 6.99 (3H, m), 7.25 (1H, dd, J=7.6, 2 Hz), 7.65 (1H, dd, J=8.8, 1.6 Hz), 7.76 (1H, d, J=8.4 Hz), 8.06 (1H, dd, J=7.6, 0.8 Hz), 8.09 (1H, br s), 8.91 (2H, br s) and 9.27 (2H, br s).

Proceeding as in Example 1, but substituting 1-tert-butyl-3-[5'-fluoro-3'-formyl-6,2'-bis-(2-methoxyethoxymethoxy) biphenyl-3-ylmethyl]-urea, gave 2-(5-fluoro-2,2'-dihydroxy-5'-ureidomethyl-biphenyl-3-yl)-1H-benzoimidazole-5-carboxamidine hydrochloride (Compound 1). MS LCMS 433.423 (M−1) (calc.), 435.423 (M+1) (calc.), (obs.); Q$^+$ 435.3 (M+1), Q$^-$ 433.3 (M−1). $^1$H-NMR (d$_6$-DMSO) δ ppm: 4.17 (2H, s), 6.38 (1H, br s), 6.87 (1H, d, J=8.4 Hz), 7.07 (1H, dd, J=8.4, 2.4 Hz), 7.12 (1H, d, J=2 Hz), 7.2 (1H, dd, J=9.2, 3.2 Hz), 7.73 (1H, br d, J=8 Hz), 7.86 (1H, d, J=8 Hz), 8.01 (1H, dd, J=9.2, 2.8 Hz), 8.18 (1H, br s), 8.96 (2H, br s) and 9.35 (2H, br s)

Proceeding as in Example 1, but substituting [3-formyl-4-(2-methoxy-ethoxymethoxy)-5-(4,4,5,5-tetramethyl-[1,3,2] dioxaborolan-2-yl)-phenyl]-acetonitrile and 1-[3-bromo-4-(2-ethoxymethoxy)-benzyl]-3-tert-butylurea, gave 2-(5-cyanomethyl-2,2'-dihydroxy-5'-ureidomethyl-biphenyl-3-yl)-1H-benzoimidazole-5-carboxamidine hydrochloride (Compound 21). MS LCMS Q$^+$ 456.476 (M+1) (calc.), Q$^-$ 454.476 (M−1) (calc.), (obs.); Q$^+$ 456.3 (M+1), Q$^-$ 454.3 (M−1). $^1$H-NMR (d$_6$-DMSO) δ ppm: 4.14 (2H, s), 4.17 (2H, s), 6.92 (1H, d, J=9.2 Hz), 7.12 (2H, m), 7.36 (1H, d, J=2.4 Hz), 7.77 (1H, d, J=8.4 Hz), 7.90 (1H, d, J=8.8 Hz), 8.14 (1H, d, J=1.6 Hz), 8.23 (1H, br s), 9.0 (2H, br s) and 9.4 (2H, br s).

Proceeding as in Example 1, but substituting N-tert-butyl-3'-formyl-2'-(2-methoxyethoxymethoxy)-5'-methyl-biphenyl-3-sulfonamide, gave 2-(5-methyl-2-hydroxy-3'-aminosulfonylbiphenyl-3-yl)-1H-benzoimidazole-5-carboxamidine hydrochloride (Compound 52). MS LCMS Q$^+$ 422.479 (M+1) (calc.), Q$^-$ 420.479 (M−1) (calc.), (obs.); Q$^+$ 422.3 (M+1), Q$^-$ 420.3 (M−1). $^1$H-NMR (d$_6$-DMSO) δ ppm: 2.34 (3H, s), 7.3 (1H, d, J=1.6 Hz), 7.32 (2H, br s), 7.56 (1H, t, J=8 Hz), 7.64 (1H, br m), 7.73 (1H, t of d, J=8.8, 1.2 Hz), 7.77 (2H, m), 7.98 (1H, br s), 8.03 (1H, t, J=1.2 Hz), 8.88 (2H, br s) and 9.28 (2H, br s).

Proceeding as in Example 1, but substituting 1-tert-butyl-3-[3'-formyl-2'-hydroxy-5'-(1H-tetrazol-5-yl)-biphenyl-3-ylmethyl]urea, gave 2-[2-hydroxy-5-(1H-tetrazol-5-yl)-3'-ureidomethylbiphenyl-3-yl]-1H-benzoimidazole-5-carboxamidine (0.01 g) as a brown solid (Compound 56). LCMS calcd. 468.48; obsvd. (M+H) 469.1, (M−H) 467.2.

Example 2

Synthesis of 5-(5-carbamimidoyl-1H-benzoimidazol-2-yl)-6-hydroxy-N-dimethyl-3'-sulfamoyl-biphenyl-3-carboxamide hydrochloride (Compound 9)

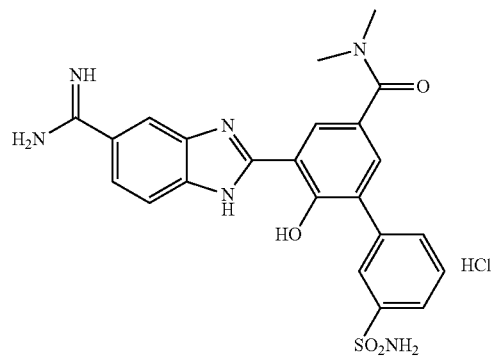

5-(5-carbamimidoyl-1H-benzoimidazol-2-yl)-6-hydroxy-3'-sulfamoyl-biphenyl-3-carboxylic acid hydrochloride (29 mg, 60 μmol, 1.0 eq.), prepared as in Reference 23, triethylamine (17 mg, 120 μmol, 2.0 eq.), benzotriazol-1-yloxy-tris (dimethylamino)-phosphonium hexafluorophosphate (29 mg, 66 μmol, 1.1 eq.) and S-pyrrolidine-2-carboxamide (6.9 mg, 60 μmol, 1.0 eq.) in anhydrous dimethyformamide (4 mL) were stirred at ambient temperature for 21 hours and then a further half-equivalent of each reagent was added to the reaction mixture. The mixture was stirred for 28 hours and then concentrated. A dimethyl amide by-product was purified from the residue by reverse-phase preparative HPLC (5→30% acetonitrile/20 mM aqueous hydrochloric acid). Fractions containing product were concentrated by lyophilization to give 5-(5-carbamimidoyl-1H-benzoimidazol-2-yl)-6-hydroxy-N-dimethyl-3'-sulfamoyl-biphenyl-3-carboxamide hydrochloride (1.8 mg, 6%) as a yellow-brown solid. $^1$H NMR (400 MHz, d$_6$-DMSO/D$_2$O): δ 9.40-9.32 (brs, 2H), 8.95-8.86 (brs, 2H), 8.29 (s, 1H), 8.17 (s, 1H), 8.10 (s, 1H), 7.88-7.84 (m, 2H), 7.82 (d, J=7.3 Hz, 1H), 7.72 (d, J=8.4 Hz, 1H), 7.65 (t, J=7.3 Hz, 1H), 7.57 (s, 1H). 3.04 (brs, 1H). m/z (LCMS-ESI): Q$^+$ 4.79 (M+H); Q$^-$ 477 (M−H).

Example 3

Synthesis of 2-[5-(2S-aminocarbonylpyrrolidin-1-ylcarbonyl)-2,2'-dihydroxy-5'-fluorobiphenyl-3-yl]-1H-benzoimidazole-5-carboxamidine hydrochloride (Compound 22)

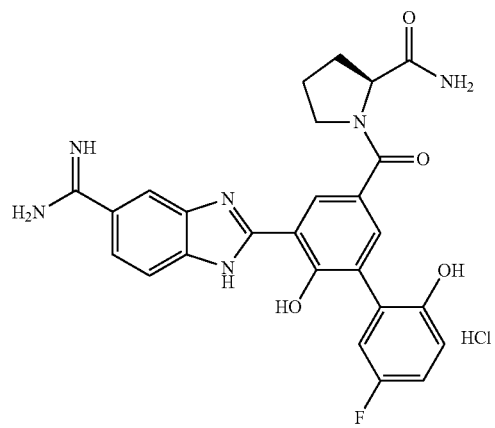

5-(5-carbamimidoyl-1H-benzoimidazol-2-yl)-5'-fluoro-6,2'-dihydroxy-biphenyl-3-carboxylic acid (0.030 g, 0.068 mmol), prepared as in Reference 23, was dissolved in dimethylformamide (5 mL) and then S-pyrrolidine-2-carboxamide (0.0074 g, 0.065 mmol) and benzotriazole-1-yloxy-tris(dimethylamino)phosphonium hexafluorophosphate (0.032 g, 0.072 mmol) were added to the solution. Triethylamine (0.018 mL, 0.130 mmol) was added and the mixture was stirred for 24 hours and then was concentrated. Product was purified from the residue by reverse phase HPLC to give (S)-1-[5-(5-carbamimidoyl-1H-benzoimidazol-2-yl)-5'-fluoro-6,2'-dihydroxy-biphenyl-3-carbonyl]-pyrrolidine-2-carboxamide hydrochloride (9 mg) as a yellow powder. $^1$H NMR (400 MHz, DMSO-$d_6$) δ 9.34 (br-s, 1H), 8.93 (br-s, 1H), 8.42 (br-s, 1H), 8.17 (br-s, 1H), 7.83 (br-d, J=8.35, 1H), 7.72 (m, 1H), 7.42 (br-s, 1H), 7.05 (m, 2H), 6.93 (m, 1H), 4.39 (t, J=7.12, 1H), 3.79 (m, 1H), 3.59 (m, 1H), 2.20 (m, 2H), 1.85 (m, 2H). ESIMS m/z: M$^+$ 503.1.

Example 4

Synthesis of 1-[5-(5-carbamimidoyl-1H-benzoimidazol-2-yl)-5'-fluoro-6,2'-dihydroxy-biphenyl-3-carbonyl]-4R-hydroxy-pyrrolidine-2S-carboxylic acid hydrochloride

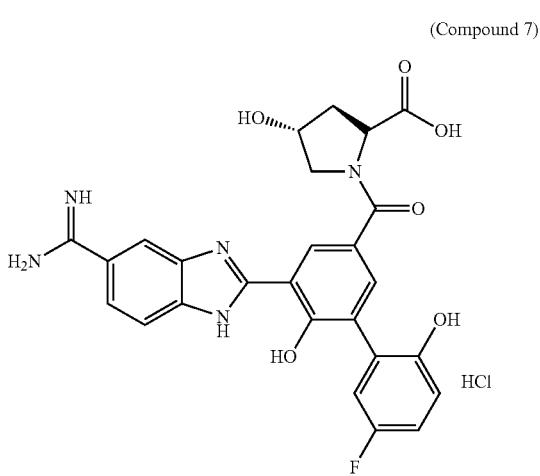

(Compound 7)

5-(5-carbamimidoyl-1H-benzoimidazol-2-yl)-5'-fluoro-6,2'-dihydroxy-biphenyl-3-carboxylic acid (0.250 g, 0.565 mmol), prepared as in Reference 23, was dissolved in N,N-dimethylformamide (7 mL) and then methyl (S)-trans-4-hydroxypyrrolidine-2-carboxylate (0.098 g, 0.538 mmol) and 2,3,4-trimethyl-pyridine (0.228 g, 1.88 mmol) were added to the solution. The mixture was cooled to 0° C. and O-(7-azabenzotriazol-1-yl)-1,2,3,3-tetramethyluroniumhexafluorophosphate (0.225 g, 0.592 mmol) was added. The mixture was stirred at 0° C. for one hour and then at room temperature for 20 hours. The mixture was concentrated and the residue taken up in 0.5 N hydrochloric acid (20 mL). The mixture was heated to 80° C. and stirred for 6 hours. The mixture was concentrated and product purified from the residue by reverse phase HPLC to give 1-[5-(5-carbamimidoyl-1H-benzoimidazol-2-yl)-5'-fluoro-6,2'-dihydroxy-biphenyl-3-carbonyl]-4R-hydroxy-pyrrolidine-2S-carboxylic acid hydrochloride (0.064 g) as a yellow powder. $^1$H NMR (400 MHz, DMSO-$d_6$) δ 9.41 (br-s, 1H), 9.13 (br-s, 1H), 8.42 (br-s, 1H), 8.20 (br-s, 1H), 7.85 (br-d, J=8.71, 1H), 7.75 (br-d, J=8.37, 1H), 7.58 (br-s, 1H), 7.10 (m, 1H), 7.03 (m, 1H), 6.96 (m, 1H), 4.54 (t, J=8.39, 1H), 4.31 (br-s, 1H), 3.97 (dd, J=11.64, 3.85, 1H), 3.50 (d, J=10.99, 1H), 2.23 (m, 1H), 1.97 (m, 1H). ESIMS m/z: M$^+$ 520.3

Example 5

Synthesis of 5-(5-carbamimidoyl-1H-benzoimidazol-2-yl)-5'-fluoro-6,2'-dihydroxy-N-pyridin-4-ylmethyl-biphenyl-3-carboxamide hydrochloride

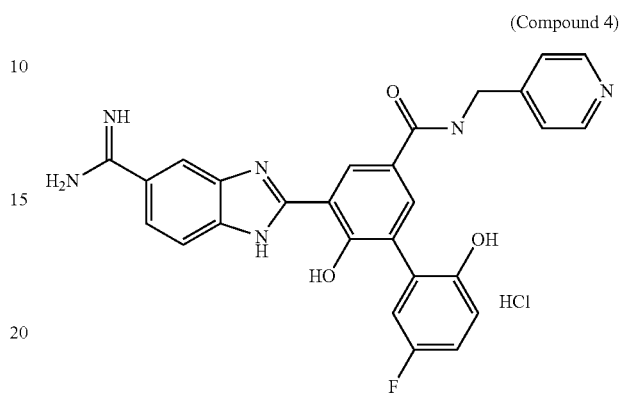

(Compound 4)

5-(5-carbamimidoyl-1H-benzoimidazol-2-yl)-5'-fluoro-6,2'-dihydroxy-biphenyl-3-carboxylic acid hydrochloride (100 mg, 0.226 mmol), prepared as in Reference 23, O-(7-azabenzotriazol-1-yl)-1,2,3,3-tetramethyluroniumhexafluorophosphate monohydrate (37 mg, 0.242 mmol) and (3-dimethylaminopropyl)ethylcarbodiimide hydrochloride (46 mg, 0.237 mmol) were dissolved in anhydrous N,N-dimethylformamide (10 mL). The mixture was stirred at room temperature for 1 hour and then 4-aminomethylpyridine (27 mg, 0.248 mmol) was added to the mixture. The mixture was stirred at ambient temperature for 18 hours and then concentrated to a gum under high vacuum. The residue was dissolved in 5% acetonitrile/95% 20 mM hydrochloric acid (10 mL) and product purified via preparative $C_{18}$ reverse phase HPLC (5% to 35% acetonitrile gradient, 20 mM HCl aqueous to give 5-(5-carbamimidoyl-1H-benzoimidazol-2-yl)-5'-fluoro-6,2'-dihydroxy-N-pyridin-4-ylmethyl-biphenyl-3-carboxamide hydrochloride (50 mg) as a tan powder. $^1$H-NMR ($d_6$-DMSO) δ ppm: 9.45 (bs, 2H), 9.20 (bs, 2H) 9.11 (d, J=1.6 Hz, 1H), 8.86 (d, J=6.4 Hz, 2H), 8.22 (d, J=1.6 Hz, 1H), 8.04 (d, J=6.4 Hz, 2H), 8.00 (d, J=2.0 Hz, 1H), 7.85 (d, J=8.0 Hz, 1H), 7.78 (dd, J=8.8, 1.6 Hz, 1H), 7.14-6.96 (m, 3H), 4.79 (d, J=5.6 Hz, 2H): MS LCMS Q$^+$ 497.174 (calc.), 497.2 (obs.), Q$^-$ 495.158 (calc.), 454.9 (obs).

Example 6

Synthesis of 2-[3'-(5-carbamimidoyl-1H-benzoimidazol-2-yl)-6,2'-dihydroxy-biphenyl-3-yl]-acetamide

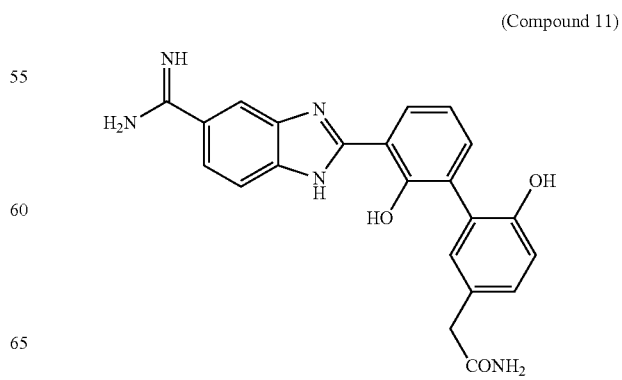

(Compound 11)

Methyl [3'-formyl-6,2'-bis(2-methoxyethoxymethoxy)biphenyl-3-yl]acetate (1.2 g, 2.59 mmol), prepared as in Reference 19, was dissolved in methanol (20 mL) and the solution was charged with 3,4-diaminobenzamidine hydrochlroide (0.58 g, 3.11 mmol) and 1,4-benzoquinone (0.28 g, 2.59 mmol). The mixture was refluxed for 3 hours and then concentrated by evaporation. The residue was dissolved in methanol (10 mL) and treated with 4 M hydrogen chloride in dioxane (10 mL). The solution was stirred for two hours and then concentrated by evaporation. The residue was dissolved in ammonia in methanol (20 mL, 7 M). The solution was transferred to a sealed tube and heated at 60° for two days while stirring. The solution was cooled and concentrated. Product was purified from the residue by preparative hplc (2, 2, 30) acetonitrile. The desired fractions containing product were pooled and concentrated by evaporation to give 2-[3'-(5-carbamimidoyl-1H-benzoimidazol-2-yl)-6,2'-dihydroxy-biphenyl-3-yl]-acetamide (420 mg). LCMS: Calcd 401.4; Obsd (MH+) 402.2, (MH−) 400.0. NMR (DMSO-$d_6$) d 3.26 (s, 2H), 6.80 (s, 1H), 6.83 (d, J=9 Hz, 1H), 7.07 (m, 2H), 7.38 (m, 2H), 7.73 (d, J=8 Hz, 1H), 7.83 (d, J=8 Hz, 1H), 8.16 (d, J=1 Hz, 1H), 8.18 (s, 1H), 9.03 (s, 2H), 9.39 (s, 2H).

Example 7

Synthesis of 2-(2,2'-dihydroxy-5-(1H-tetrazol-5-yl)-3'-aminomethylbiphenyl-3-yl]-1H-benzoimidazole-5-carboxamidine (Compound 57)

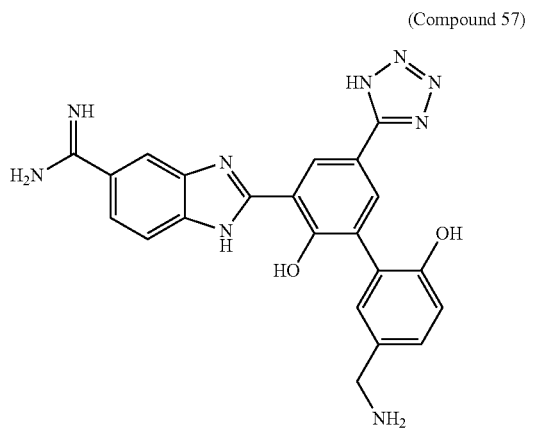 [SMILES: N=C(N)c1ccc2[nH]c(-c3cc(-c4nnn[nH]4)cc(-c4cc(CN)ccc4O)c3O)nc2c1]

3'-Formyl-6,2'-(2-methoxyethoxymethoxy)-5'-(2-methoxyethoxymethyl)-1H-tetrazol-5-ylbiphenyl-3-ylcarbonitrile (0.3 g, 0.5 mmol), 3,4-diaminobenzamidine hydrochloride (0.11 g, 0.6 mmol) and 1,4-benzoquinone (0.05 g, 0.5 mmol) were combined in methanol (15 mL) and the mixture was refluxed for 4 hours. 4M hydrogen chloride in dioxane (3 mL) was added to the mixture and stirring was continued at room temperature for 14 hours. The mixture was concentrated by evaporation. The residue was dried under high vacuum and then dissolved in methanol (50 mL). The solution was subjected to hydrogenation (balloon) using 10% Pearlman's catalyst. Filtration and drying afforded 2-(2,2'-dihydroxy-5-(1H-tetrazol-5-yl)-3'-aminomethylbiphenyl-3-yl]-1H-benzoimidazole-5-carboxamidine as the crude product (0.2 g, 88%). LCMS calcd. 441.17, obsrvd. (M+H) 442.2, (M−H) 440.2.

Example 8

Synthesis of 2-(2,2'-dihydroxy-5-(1H-tetrazol-5-yl)-3'-ureidomethylbiphenyl-3-yl]-1H-benzoimidazole-5-carboxamidine (Compound 13)

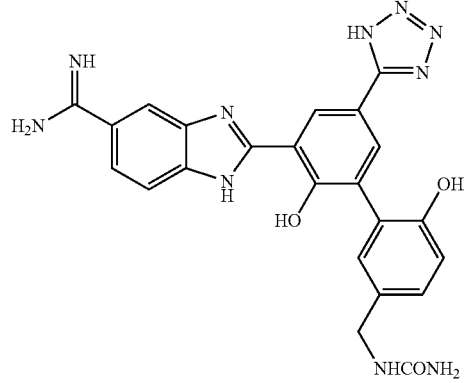

2-(2,2'-Dihydroxy-5-(1H-tetrazol-5-yl)-3'-aminomethylbiphenyl-3-yl]-1H-benzoimidazole-5-carboxamidine (0.2 g 0.2 mmol), prepared as in Example 7, was dissolved in methanol (10 mL). The solution was treated with triethylamine (0.2 mL, 1.5 mmol) and then potassium cyanate (0.09 g, 1.1 mmol aqueous solution, 0.5 mL) was added in 3 portions over 1 hour. 1N hydrochloric acid (5 mL) was added and the mixture was stirred at 50° C. over 3 days. Drying afforded crude product, which was subjected to purification by reverse phase HPLC to give 2-(2,2'-dihydroxy-5-(1H-tetrazol-5-yl)-3'-ureidomethylbiphenyl-3-yl]-1H-benzoimidazole-5-carboxamidine (0.008 g) as a brown solid. LCMS calcd. 484.47, obsrvd. (M+H) 485.1, (M−H) 483.1.

Example 9

Synthesis of 2-(5-acetylsulfamoyl-2-hydroxy-3'-sulfamoyl-biphenyl-3-yl)-1H-benzoimidazole-5-carboxamidine (Compound 31)

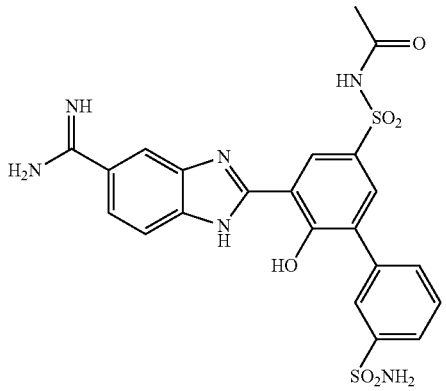

N-acetyl-N-tert-butyl-5-formyl-6-methoxy-biphenyl-3,3'-disulfonamide (100 mg, 0.21 mmol), prepared as in Reference 19, was dissolved in dichloromethane (10 mL). The solution was flushed with nitrogen for 5 minutes and then boron tribromide (1.0 mL, 1M solution in dichloromethane) was added. The mixture was stirred at room temperature for 1 hour and then concentrated under by evaporation under reduced pressure. The residue was partitioned between water and ethyl acetate. The organic layer was washed with brine and dried over anhydrous magnesium sulfate. The residue was passed through a short silica plug with pure ethyl acetate to give N-acetyl 5-formyl-6-hydroxy-biphenyl-3,3'-disulfonamide (74 mg) as a colorless oil.

N-acetyl 5-formyl-6-hydroxy-biphenyl-3,3'-disulfonamide (74 mg, 0.19 mmol) was dissolved in methanol (10 mL) and stirred at room temperature. 3,4-Diaminobenzamidine (39 mg, 0.21 mmol) and 1,4-benzoquinone (20 mg, 0.2 mmol) were added to the solution and the mixture was refluxed for 1 hour. The solvent was removed by rotary evaporation under reduced pressure and the residue was dissolved in water and acetonitrile and purified by reverse phase HPLC (0.02N HCl/ACN) to give 2-(5-acetylsulfamoyl-2-hydroxy-3'-sulfamoyl-biphenyl-3-yl)-1H-benzoimidazole-5-carboxamidine (14.1 mg) as a yellow amorphous powder. MS m/z: 527.4 (M–H$^+$) and 529.3 (M+H$^+$). $^1$H NMR (400 MHz, DMSO-d$_6$): δ 9.36 (bs, 2H), 8.94 (bs, 2H), 8.08 (d, J=2.2 Hz, 1H), 8.22 (bs, 1H), 8.10 (t, J=1.5 Hz, 1H), 7.96 (d, J=2.2 Hz, 1H) 7.89 (d, J=1.8 Hz, 1H), 7.87-7.85 (m, 2H), 7.76 (dd, J=10, 1.5 Hz, 1H), 7.71 (t, J=7.7 Hz, 1H), 7.46 (s, 2H) and 1.96 (s, 3H).

Proceeding as in Example 9, but substituting N-butyl-N'-tert-butyl-5-formyl-6-methoxy-biphenyl-3,3'-disulfonamide (352 mg, 0.69 mmol) gave 2-(5-butylsulfamoyl-2-hydroxy-3'-sulfamoyl-biphenyl-3-yl)-1H-benzoimidazole-5-carboxamidine (Compound 15). MS m/z: 569.2 (M–H$^+$) and 571.2 (M+H$^+$). $^1$H NMR (400 MHz, DMSO-d$_6$): δ 9.35 (bs, 2H), 8.91 (bs, 2H), 8.80 (s, 1H), 8.21 (t, J=1.5 Hz, 1H), 8.16 (d, J=1.8 Hz, 1H), 7.95 (t, J=1.5 Hz, 1H), 7.93 (t, J=1.5 Hz, 1H), 7.87 (t, J=1.5 Hz, 1H), 7.85 (t, J=1.5 Hz, 1H), 7.75 (d, J=12.2 Hz, 1H) 7.70 (t, J=8.0 Hz, 1H), 7.21 (s, 2H), 3.57 (t, J=8.0 Hz, 2H), 1.71 (q, J=11.1, 11.1, 7.6 Hz, 2H), 1.43 (sext, J=22.2, 11.1, 7.6 Hz, 2H), and 0.89 (t, J=7.3 Hz, 3H).

Proceeding as in Example 9, but substituting 3'-formyl-4'-(methoxyethoxymethoxy)-N-tert-butyl-biphenylsulfonamide which was dissolved in neat TFA (5 mL) and stirred overnight to give 3'-formyl-4'-hydroxybiphenyl-3-sulfonic acid amide which was converted to 2-(2-hydroxy-3'-aminosulfonylbiphenyl-3-yl)-1H-benzoimidazole-5-carboxamidine (Compound 14). MS m/z: 406.2 (M–H$^+$) and 408.3 (M+H$^+$). $^1$H NMR (400 MHz, DMSO-d$_6$): δ 9.35 (bs, 2H), 8.97 (bs, 2H), 8.23 (d, J=7.3 Hz, 1H), 8.11 (t, J=1.5 Hz, 1H), 7.85 (t, J=1.5 Hz, 1H), 7.83 (t, J=1.5 Hz, 1H), 7.82 (t, J=1.5 Hz, 1H), 7.80 (t, J=1.5 Hz, 1H), 7.31 (d, J=9.1 Hz, 1H) 7.64 (t, J=8.1 Hz, 1H), 7.54 (dd, J=8.1, 1.5 Hz, 1H), 7.39 (s, 2H) and 7.19 (t, J=7.7 Hz, 1H).

Example 10

Synthesis of 2-[2,2'-dihydroxy-5-(3-phenylpropionylaminosulfonyl)biphenyl-3-yl]-1H-benzoimidazole-5-carboxamidine (Compound 114)

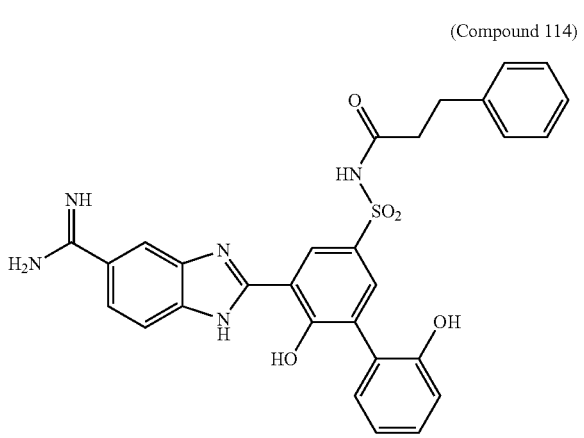 [SMILES: N=C(N)c1ccc2[nH]c(-c3cc(S(=O)(=O)NC(=O)CCc4ccccc4)cc(-c4ccccc4O)c3O)nc2c1]

N-(3-Phenylpropionyl)-5-formyl-6,2'-dihydroxy-biphenyl-3-sulfonamide (0.065 g, 0.15 mmol), prepared as in Reference 22, 3,4-diaminobenzamidine hydrochloride (0.043 g 0.23 mmol) and benzoquinone (0.018 g, 0.16 mmol) were combined in ethanol (15 mL) and the mixture was heated under reflux for 1 hour. The solvent was evaporated in vacuum and the product was purified from the residue by reverse phase HPLC (acetonitrile/0.02N HCl gradient) to give 2-[2,2'-dihydroxy-5-(3-phenylpropionylaminosulfonyl)biphenyl-3-yl]-1H-benzoimidazole-5-carboxamidine (0.033 g). $^1$H NMR (DMSO-d$_6$): δ 2.50 (t, J=7.7 Hz, 2H), 2.63 (t, J=7.7 Hz, 2H), 6.82-7.22 (m, 9H), 7.72 (dd, J$_1$=9.2 Hz, J$_2$=1.7 Hz, 1H), 7.78 (d, J=2.5 Hz, 1H), 7.84 (d, J=9.2 Hz, 1H), 8.18 (s, 1H), 8.68 (d, J=2.5 Hz, 1H), 8.99 (s, 2H), 9.34 (s, 2H), 12.06 (s, 1H). MS. found (M+H$^+$) 556.4, (M–H$^+$) 554.4, calc 555.16.

Proceeding as in Example 10, but substituting 5-formyl-6-methoxy-3'-nitro-N-(4-phenylbutyryl)-biphenyl-3-sulfonamide, gave 2-[2-hydroxy-3'-nitro-5-(4-phenyl-butyrylsulfamoyl)-biphenyl-3-yl]-1H-benzoimidazole-5-carboxamidine, Compound 115. MS. found (M+H$^+$) 600.0, (M–H$^+$) 597.6, calc. 598.16.

Proceeding as in Example 10, but substituting 5-formyl-6-hydroxy-3'-nitro-N-(3-pyridin-3-yl-propionyl)-biphenyl-3-sulfonamide, gave 2-[2-hydroxy-3'-nitro-5-(3-pyridin-3-yl-propionylsulfamoyl)-biphenyl-3-yl]-1H-benzoimidazole-5-carboxamidine (Compound 116). MS. found (M+H$^+$) 586.4, (M–H$^+$) 584.3, calc. 585.14.

Proceeding as in Example 10, but substituting 3'-amino-5-formyl-6-hydroxy-N-(3-pyridin-3-yl-propionyl)-biphenyl-3-sulfonamide, gave 2-[3'-amino-2-hydroxy-5-(3-pyridin-3-yl-propionylsulfamoyl)-biphenyl-3-yl]-1H-benzoimidazole-5-carboxamidine (Compound 117). MS. found (M+H$^+$) 556.2, (M–H$^+$) 554.3, calc. 555.17.

Example 11

Synthesis of 2-[3'-amino-2-hydroxy-5-(4-phenyl-butyrylsulfamoyl)-biphenyl-3-yl]-1H-benzoimidazole-5-carboxamidine (Compound 118)

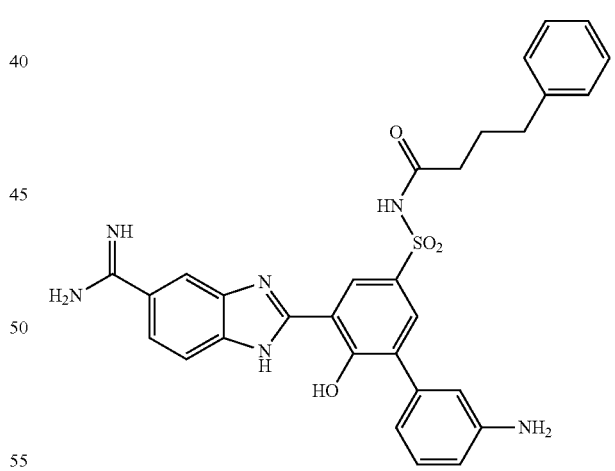

2-[2-Hydroxy-3'-nitro-5-(4-phenyl-butyrylsulfamoyl)-biphenyl-3-yl]-1H-benzoimidazole-5-carboxamidine (0.063 g, 0.1 mmol), prepared as in Example 10 was dissolved in methanol (3 mL) and saturated aqueous ammonium chloride (1 mL) was added to the solution. The mixture was heated with iron powder (1 g) for 5-10 minutes, filtered through celite and concentrated under reduced pressure. Product was purified from the residue by reverse phase HPLC (acetonitrile gradient) to give 2-[3'-amino-2-hydroxy-5-(4-phenyl-butyrylsulfamoyl)-biphenyl-3-yl]-1H-benzoimidazole-5-carboxamidine (0.017 g). MS. found (M+H$^+$) 569.3, (M–H$^+$) 567.4, calc. 568.19.

Example 12

Synthesis of 2-[2-hydroxy-5-(3-pyridin-3-yl-propionylsulfamoyl)-3'-ureido-biphenyl-3-yl]-1H-benzoimidazole-5-carboxamidine (Compound 119)

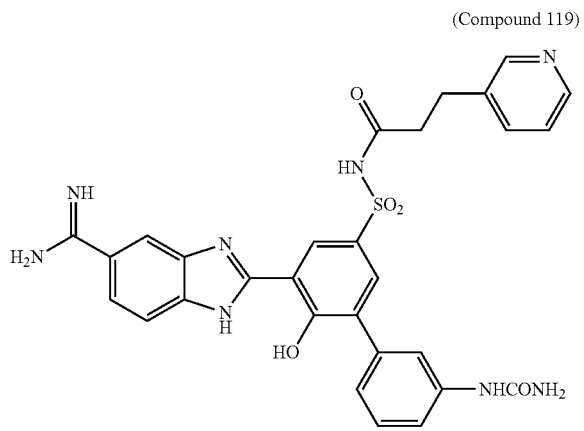

2-[3'-Amino-2-hydroxy-5-(3-pyridin-3-yl-propionylsulfamoyl)-biphenyl-3-yl]-1H-benzoimidazole-5-carboxamidine (0.015 g, 0.023 mmol), prepared as in Example 10, was dissolved in a mixture of methanol and water and then triethylamine was added to bring the solution to pH 9. The mixture was heated with potassium cyanate (0.018 g, 0.23 mmol) for 12 hour at 40° C., concentrated by evaporation under reduced pressure and the crude product was purified by reversed phase HPLC (acetonitrile gradient) to give 2-[2-hydroxy-5-(3-pyridin-3-yl-propionylsulfamoyl)-3'-ureido-biphenyl-3-yl]-1H-benzoimidazole-5-carboxamidine (0.01 g). MS. found (M+H$^+$) 599.5, (M−H$^+$) 597.7, calc. 598.17.

Example 13

Synthesis of 2-[3'-amino-2-hydroxy-5-(3-piperidin-3-yl-propionylsulfamoyl)-biphenyl-3-yl]-1H-benzoimidazole-5-carboxamidine (Compound 120)

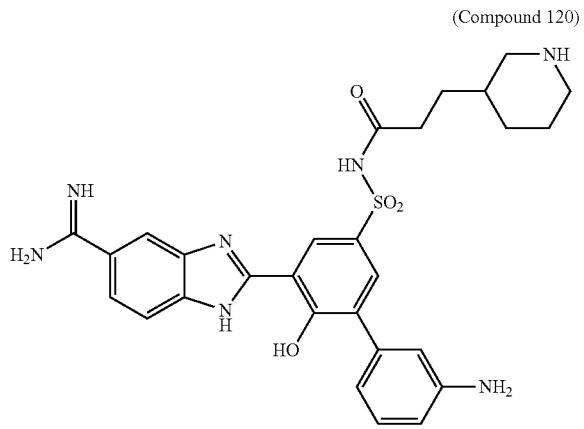 [SMILES: N=C(N)c1ccc2[nH]c(-c3cc(S(=O)(=O)NC(=O)CCC4CCCNC4)cc(-c4cccc(N)c4)c3O)nc2c1]

2-[2-Hydroxy-3'-nitro-5-(3-pyridin-3-yl-propionylsulfamoyl)-biphenyl-3-yl]-1H-benzoimidazole-5-carboxamidine (0.031 g, 0.05 mMol), prepared as in Example 10, was dissolved in trifluoroacetic acid (5 mL) and the solution was subjected to hydrogenation at 50 psi over PtO$_2$ catalyst for 12 hours. The mixture was concentrated in vacuum and product was purified from the residue by reverse phase HPLC (acetonitrile gradient) to give 2-[3'-amino-2-hydroxy-5-(3-piperidin-3-yl-propionylsulfamoyl)-biphenyl-3-yl]-1H-benzoimidazole-5-carboxamidine (0.01 g). MS. found (M+H$^+$) 562.4, (M−H$^+$) 560.6, calc. 561.22.

Example 14

Synthesis of 2-(2,2'-dihydroxy-5-sulfamoyl-5'-ureidomethyl-biphenyl-3-yl)-1H-benzoimidazole-5-carboxamidine (Compound 12)

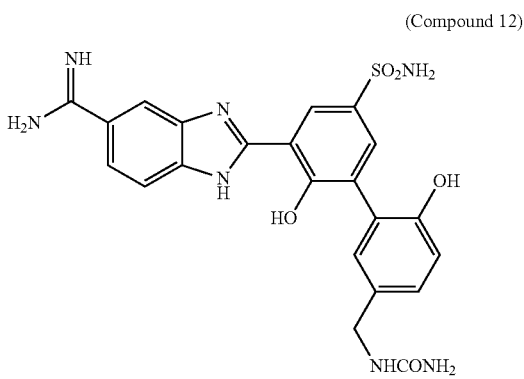

5'-Cyano-5-formyl-6,2'-dimethoxybiphenyl-3-sulfonic acid amide (0.35 g, 1 mmole), prepared as in Reference 19, was heated with pyridine hydrochloride (3.5 g) at 185° C. for 2 hours. The melt was dissolved in 1N hydrochloric acid (15 mL) and the solution was extracted with ethyl acetate. The ethyl acetate layer was washed with water and brine, dried over magnesium sulfate and concentrated. The residue was dissolved in methanol (25 mL) along with 3,4-diaminobenzamidine hydrochloride (0.21 g, 1.1 mmol) and benzoquinone (0.11 g, 1.0 mmol). The mixture was heated for 4 hours and concentrated. The residue was washed with ethyl ether and then dissolved in a 2:1 mixture of methanol and 1N hydrochloric acid (25 mL). The solution was subjected to hydrogenation at atmospheric pressure over Pearlman's catalyst (0.1 g) for 2 hours. The mixture was and the mother liquor was concentrated by evaporation under reduced pressure. The residue was dissolved in 2:1 mixture of methanol and water and triethylamine was added to bring the solution to pH 10.

The mixture was heated with potassium cyanate (0.32 g, 4 mmol) for 16 hours at 40 to 50° C. and then concentrated by evaporation. Product was purified from the residue by reversed phase HPLC (acetonitrile gradient) to give 2-(2,2'-dihydroxy-5-sulfamoyl-5'-ureidomethyl-biphenyl-3-yl)-1H-benzoimidazole-5-carboxamidine (0.035 g). $^1$H NMR (DMSO-d$_6$) δ 4.11 (s, 2H), 6.39 (br.s, 1H), 6.88 (d, J=8.8 Hz, 1H), 7.09-7.11 (m, 2H), 7.32 (br.s, 2H), 7.74 (dd, J$_1$=8.4 Hz, J$_2$=1.5 Hz, 1H), 7.81 (d, J=2.2 Hz, 1H), 7.85 (d, J=8.4 Hz, 1H), 8.18 (s, 1H), 8.61 (d, J=2.2 Hz, 1H), 8.99 (s, 2H), 9.36 (s, 2H), 12.06 (s, 1H). MS. found (M+H$^+$) 496.3, (M−H$^+$) 494.2, calc 495.13.

Example 15

Synthesis of 2-[5-(5-carbamimidoyl-1H-benzoimidazol-2-yl)-5'-fluoro-6,2'-dihydroxy-biphenyl-3-yl]-N-(2-hydroxy-ethyl)-acetamide

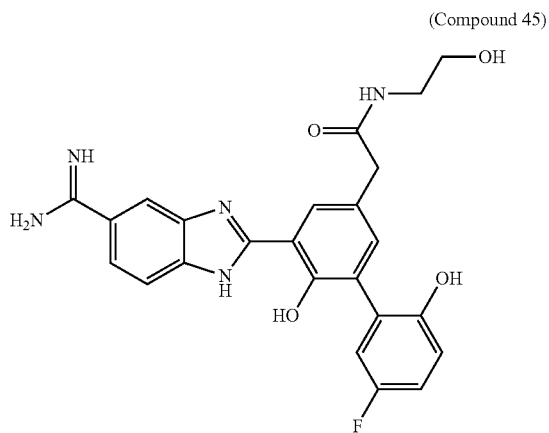 [SMILES: N=C(N)c1ccc2[nH]c(-c3cc(CC(=O)NCCO)cc(-c4cc(F)ccc4O)c3O)nc2c1]

(Compound 45)

3-(5-carbamimidoyl-1H-benzoimidazol-2-yl)-5'-fluoro-6,2'-dihydroxy-biphenyl-2-yl-acetic acid (0.04 g, 0.09 mmol), prepared as in Reference 9, was dissolved in dimethylformamide (1 mL) and then diisopropylethylamine (0.03 mL, 0.18 mmol), 2-aminoethanol (0.008 mL, 0.14 mmol) and bromotripyrrolidinophos-phonium hexafluorophosphate (0.05 g, 0.12 mmol) was added to the solution. The mixture was stirred for 1 hour and then concentrated under vacuum. Product was purified from the residue by reverse phase HPLC to give 2-[5-(5-carbamimidoyl-1H-benzoimidazol-2-yl)-5'-fluoro-6,2'-dihydroxy-biphenyl-3-yl]-N-(2-hydroxy-ethyl)-acetamide (0.025 g, 61%) as an off-white solid. LCMS calcd. 463.47, obsrvd. (M+H) 464.2, (M−H) 462.4.

Proceeding as in Example 15, but substituting 2-aminopropane-1,3-diol (0.013 g, 0.14 mmol), gave 2-[2,2'-dihydroxy-5'-fluoro-5-(N-(1-hydroxymethyl-2-hydroxyethylaminocarbonylmethyl)biphenyl-3-yl]-1H-benzoimidazole-5-carboxamidine (0.015 g, 34%) as an off-white solid. LCMS calcd. 493.49, obsrvd. (M+H) 494.1, (M−H) 492.3.

Example 16

Synthesis of N-[3'-(5-carbamimidoyl-1H-benzoimidazol-2-yl)-6,2'-dihydroxy-biphenyl-3-ylmethyl]-2-hydroxy-acetamide (Compound 79)

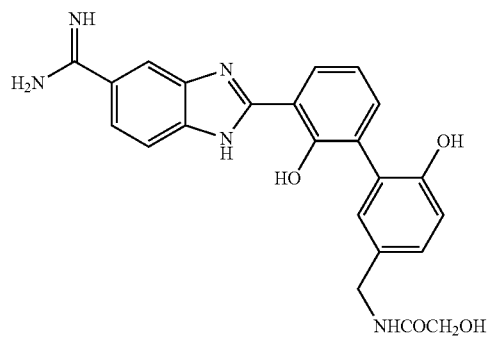

tert-Butyl 1[3'-formyl-6,2'-bis(2-methoxyethoxymethoxy) biphenyl-3-ylmethyl]carbamate (0.284 g, 0.55 mmol) was dissolved in methanol (15 mL) and the solution was treated with diamino-benzamidine hydrocloride (0.112 g, 6.0 mmol) and 1,4-benzoquinone (65 mg, 6.0 mmol). The mixture was refluxed for 3 hours and then concentrated by evaporation. The residue was dissolved in methanol (15 mL) and hydrogen chloride (15 mL, 4M in dioxane) was added to the solution. The mixture was stirred for one hour and then concentrated. Product was purified from the crude by preparative HPLC (2,2,25) (acetonitrile) to give 2-(5'-aminomethyl-2,2'-dihydroxybiphenyl-3-yl)-1H-benzoimidazole-5-carboxamidine (210 mg).

2-(5'-Aminomethyl-2,2'-dihydroxybiphenyl-3-yl)-1H-benzoimidazole-5-carboxamidine (25 mg, 0.056 mmol) was dissolved in dimethylformamide (5 mL) and triethylamine (0.030 g, 0.30 mmol, 0.042 mL) and 2,5-dioxo-pyrrolidin-1-y acetoxyacetate (0.0215 g, 0.10 mmol) were added to the solution. The mixture was stirred for 30 minutes and then concentrated by evaporation. The residue was combined with methanol (5 mL) and potassium carbonate (1.0 mL, 1 M) and the mixture was stirred for 1 hour. The reaction mixture was acidified to pH-3 and then concentrated by evaporation. The residue was prepped at (2,2,25) (acetonitrile) to give N-[3'-(5-carbamimidoyl-1H-benzoimidazol-2-yl)-6,2'-dihydroxy-biphenyl-3-ylmethyl]-2-hydroxy-acetamide (17 mg). LCMS: Calcd=431.5; Obsd, (MH+)=432.2, (MH−)=430.2. NMR (DMSO-$d_6$) d 3.80 (s, 2H), 4.22 (d, J=6 Hz, 2H), 6.84 (d, J=8 Hz, 1H), 7.07 (m, 2H), 7.33 (d of d, J=1.5, 8 Hz, 1H), 7.72 (d of d, J=3, 8 Hz, 1H), 7.83 (d, J=8 Hz, 1H), 8.12 (m, 2H), 8.16 (br s, 1H), 8.98, 9.35 (2s, 4H).

Example 17

2-[5-(5-carbamimidoyl-1H-benzoimidazol-2-yl)-6,2'-dihydroxy-5'-sulfamoyl-biphenyl-3-yl]-N-(2-morpholin-4-yl-ethyl)-acetamide (Compound 43)

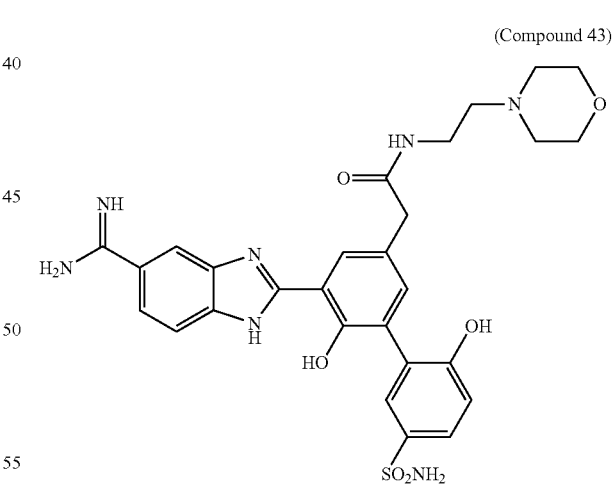

[5-(5-carbamimidoyl-1H-benzoimidazol-2-yl)-6,2'-dihydroxy-5'-sulfamoyl-biphenyl-3-yl]-acetic acid (96 mg, 0.20 mmol), prepared as in Reference 9, was dissolved in dry N,N-dimethylformamide (20 mL) and the solution was treated with O-(7-azabenzotriazol-1-yl)-N,N,N',N'-tetramethyluronium hexafluorophosphate (84 mg, 0.22 mmol) and 2,3,4-trimethyl-pyridine (0.106 mL, 0.80 mmol). The mixture was stirred for one hour and then 4-(2-aminoethyl)-morpholine (29 uL, 0.22 mmol) was added. The mixture was stirred until the reaction was complete (½ to 1 hours) and then neutralizated with 1N hydrochloric acid to pH~3. The solvents were evaporated at 30° C. to give an oily residue. The crude amide then was prepped at 2:30 (acetonitrile/20 mmol HCl) and the solvents were lyophilized to give 2-[5-(5-carbamimidoyl-1H-benzoimidazol-2-yl)-6,2'-dihydroxy-5'-sulfamoyl-biphenyl-3-yl]-N-(2-morpholin-4-yl-ethyl)-acetamide (63.0 mg, 53%). LCMS: (MH+)=594.3; (MH−)=592.2. NMR (DMSO-d6) d 2.78 (m, 4H), 3.12 (m, 2H), 3.26 (t, J=3 Hz, 2H), 3.57 (m, 4H), 3.59 (s, 2H), 7.17 (d, J=5 Hz, 1H), 7.23 (br s, 1H), 7.37 (d, J=1.5 Hz, 1H), 7.70 (m, 2H), 7.79 (d of d, J=1.5 Hz, 1H), 7.88 (d, J=5 Hz, 1H), 8.22 (d, J=1 Hz, 1H), 8.24 (s, 1H), 8.59 (t, J=3 Hz, 1H), 9.18, 9.43 (2s, 4H).

Proceeding as in Example 17, but substituting lithium 2-aminoethanesulfonate (54 mg), prepared as in Reference 4, in hot dimethyl sulfoxide (4 mL) and triethylamine (200 uL), gave 2-{2-[5-(5-carbamimidoyl-1H-benzoimidazol-2-yl)-6, 2'-dihydroxy-5'-sulfamoyl-biphenyl-3-yl]-acetylamino}-ethanesulfonic acid (55 mg, 45%) (Compound 234). LCMS: (MH+)=589.1. (MH−)=587.2, NMR (DMSO-d6) d 2.71 (t, J=6 Hz, 2H), 3.43 (t, J=6 Hz, 2H), 3.46 (t, J=6 Hz, 1H), 7.03 (d, J=5 Hz, 1H), 7.18 (br s, 1H), 7.24 (d, J=1 Hz, 1H), 7.63 (d of d, J=1, 5 Hz, 1H), 7.68-7.75 (m, 2H), 7.85 (d, J=5 Hz, 1H), 8.19 (s, 1H), 8.26 (d, J=1 Hz, 1H), 8.43 (t, J=5 Hz, 1H), 8.86, 9.37 (2s, 4H).

Proceeding as in Example 17, but substituting tert-butyl 6-amino-2-tert-butoxycarbonylamino-hexanoate (0.65 g), prepared as in Reference 5, gave 2-amino-6-{2-[5-(5-carbamimidoyl-1H-benzoimidazol-2-yl)-6,2'-dihydroxy-5'-sulfamoyl-biphenyl-3-yl]-acetylamino}-hexanoic acid (68 mg, 53%) (Compound 112). LCMS: (MH+)=610.4. (MH−)=608.6, NMR (DMSO-d6) d 1.3-1.5 (m, 2H), 1.8 (m, 2H), 3.08 (q, J=6 Hz, 2H), 3.51 (s, 2H), 3.89 (q, J=6 Hz, 1H), 7.05 (d, J=5 Hz, 1H), 7.18 (br s, 1H), 7.31 (d, J=1 Hz, 1H), 7.65 (m, 2H), 7.77 (d of d, J=1, 5 Hz, 1H), 7.83 (d, J=5 Hz, 1H), 8.14 (d, J=1 Hz, 1H), 8.21 (s, 1H), 8.38 (d, J=5 Hz, 2H), 9.15, 9.42 (2s, 4H).

Proceeding as in Example 17, but substituting 1-methylpiperazine (25 uL) and triethylamine (40 uL), gave 2-{2,2'-dihydroxy-5-[2-(4-methyl-piperazin-1-yl)-2-oxo-ethyl]-5'-sulfamoyl-biphenyl-3-yl}-1H-benzoimidazole-5-carboxamidine (55 mg, 48%), Compound 113. LCMS: (MH+)=564.2; (MH−)=562.1; NMR (DMSO-d6) d 2.79 (s, 3H), 2.9-3.2 (m, 2H), 3.43 (t, J=6 Hz, 2H), 3.55 (t, J=14 Hz, 1H), 3.70 (m, 1H), 3.80 (s, 2H), 4.33 (d, J=14 Hz, 1H), 4.47 (d, J=14 Hz, 1H), 7.12 (d, J=5 Hz, 1H), 7.20 (br s, 1H), 7.24 (d, J=1 Hz, 1H), 7.6-7.8 (m, 2H), 7.75 (d, J=5 Hz, 1H), 7.84 (d, J=5 Hz, 1H), 8.13 (d, J=1 Hz, 1H), 8.21 (s, 1H), 9.02, 9.41 (2s, 4H).

Proceeding as in Example 17, but substituting (2-aminoethyl)-trimethylammonium chloride (73 mg, 0.41 mmol) in a mixture of dimethyl sulfoxide (4 mL) and triethylamine (57 uL) heated to 80° C. which mixture was added in a dropwise fashion to the reaction mixture, gave (2-{2-[5-(5-carbamimidoyl-1H-benzoimidazol-2-yl)-6,2'-dihydroxy-5'-sulfamoyl-biphenyl-3-yl]-acetylamino}-ethyl)-trimethyl-ammonium (53 mg, 43%), Compound 105. NMR (DMSO-d6) d 3.05 (s, 9H), 3.42 (q, J=6 Hz, 2H), 3.55 (m, 6H), 7.12 (d, J=5 Hz, 1H), 7.20 (br s, 1H), 7.30 (d, J=1 Hz, 1H), 7.67 (m, 2H), 7.78 (d of d, J=1, 5 Hz, 1H), 7.83 (d, J=5 Hz, 1H), 8.20 (m, 2H), 8.61 (t, J=6 Hz, 1H), 9.11, 9.41 (2s, 4H).

Proceeding as in Example 17, but substituting 5-(5-carbamimidoyl-1H-benzoimidazol-2-yl)-6,2'-dihydroxy-5'-sulfamoylbiphenyl-3-carboxylic acid, prepared as in Reference 10, gave N-(2-morpholin-4-yl-ethyl) 5-(5-carbamimidoyl-1H-benzoimidazol-2-yl)-6,2'-dihydroxy-5'-sulfamoyl-biphenyl-3-carboxamide as a yellow solid, Compound 110. RP-HPLC (1-90S) RT=2.26 min. $^1$H NMR (400 MHz, d$_6$-DMSO, selected signals): δ 10.40* (1H, v br s), 10.27* (1H, v br s), 9.36* (2H, s), 8.96* (3H, m), 8.80* (1H, br t, J=5.7 Hz), 8.18 (1H s), 7.94 (1H, d, J=2.0 Hz), 7.85 (1H, d, J=8.4 Hz), 7.74 (1H, dd, J=8.4, 1.6 Hz), 7.69 (1H, d, J=2.0 Hz), 7.68 (1H, dd, J=8.4, 1.6 Hz), 7.18* (2H, s), 7.08 (1H, d, J=8.4 Hz), 3.99 (2H, br m), 3.79 (2H, br m), 3.71 (2H, br m), 3.58 (2H, m), 3.15 (2H, m); m/z (LCMS-ESI): Q$^+$ 580 (M+H); Q$^+$ 578 (M−H).

Proceeding as in Example 17, but substituting 5-(5-carbamimidoyl-1H-benzoimidazol-2-yl)-6,2'-dihydroxy-5'-sulfamoylbiphenyl-3-carboxylic acid (20 mg, 40 μmol), prepared as in Reference 10, and lithium 2-aminoethanesulfonate, prepared as in Reference 4, gave 2-{[5-(5-carbamimidoyl-1H-benzoimidazol-2-yl)-6,2'-dihydroxy-5'-sulfamoyl-biphenyl-3-carbonyl]-amino}-ethanesulfonic acid as a yellow solid, Compound 111. RP-HPLC (1-90S) RT=2.21 min; $^1$H NMR (400 MHz, d$_6$-DMSO, selected signals): δ 9.36* (2H, s), 8.98* (2H, s), 8.74 (1H, J=1.6 Hz), 8.74 (1H, d, J=2.0 Hz), 8.49* (1H, br t, J=5.0 Hz), 8.17 (1H, s), 7.85 (1H, d, J=8.4 Hz), 7.81 (1H d, J=2.0 Hz), 7.75 (1H, dd, J=8.4 Hz, 0.8 Hz), 7.70 (1H, dd, J=2.4 Hz), 7.67 (1H, dd, J=8.4, 2.4 Hz); 7.16* (2H, br s), 7.07 (1H, d, J=8.4 Hz); m/z (LCMS-ESI): Q$^+$ 575 (M+H); Q$^-$ 573 (M−H).

Proceeding by analogous methods provided in the Examples set forth herein gave:

2S-{2-[5-(5-carbamimidoyl-1H-benzoimidazol-2-yl)-6, 2'-dihydroxy-5'-sulfamoyl-biphenyl-3-yl]-acetylamino}-succinamic acid hydrochloride, Compound 121, $^1$H NMR: 9.30 (2H, br s), 8.87 (2H, br s), 8.23 (d, 1H, J=7.6 Hz), 8.09 (1H, br s), 7.92 (1H, br s), 7.76 (d, 1H, J=7.2 Hz), 7.65 (1H, d, J=8.4 Hz), 7.6-7.57 (2H, m), 7.38 (1H, s), 7.20 (1H, d, J=2.4 Hz), 7.08 (1H, br s), 6.97 (1H, d, J=9.2 Hz), 6.865 (1H, br s), 4.47 (1H, dd, J=7.6 and 5.6 Hz), 3.62 (2H br s), 2.48 (2H, d of ABq, J=15.2 and 5.6 Hz);

2R-{2-[5-(5-carbamimidoyl-1H-benzoimidazol-2-yl)-6, 2'-dihydroxy-5'-sulfamoyl-biphenyl-3-yl]-acetylamino}-succinic acid, Compound 123, H$^1$ NMR (CD$_3$DO-d4) 9.33 (s, 2H) 8.94 (s, 2H) 8.46 (d, 1H, J=7.8 Hz) 7.99 (d, 1H, J=1.6 Hz) 7.839 (d, 1H, J=8.6 Hz) 7.73 (dd, 1H, J=1.2 Hz, 8.6 Hz) 7.66 (d, 1H, J=2.3 Hz) 7.661 (dd, 1H, J=2.7 Hz, 8.6 Hz) 7.285 (d, 1H, J=2.3 Hz) 7.051 (d, 1H, 8.2 Hz) 4.57 (q, 1H, J=7.0 Hz, 14.1 Hz) 3.542 (s, 2H) 2.741 (m, 1H);

1-{2-[5-(5-carbamimidoyl-1H-benzoimidazol-2-yl)-6,2'-dihydroxy-5'-sulfamoyl-biphenyl-3-yl]-acetyl}-pyrrolidine-2R-carboxamide, Compound 124, $^1$H NMR (400 MHz, DMSO-d$_6$) δ 10.24 (br-s, 1H), 9.30 (br-s, 1H), 8.85 (br-s, 1H), 8.15 (br-s, 1H), 7.98 (d, 1H, J=1.75, 1H), 7.83 (br-d, J=9.3, 1H), 7.70 (br-d, J=9.17, 1H), 7.64 (m, 2H), 7.36 (br-s, 1H), 7.25 (d, J=2.02, 1H), 7.15 (s, 1H), 7.03 (d, J=8.08, 1H), 6.94 (br-s, 1H), 4.25 (dd, J=5.64, 3.16, 1H), 3.72 (s, 2H), 3.59 (m, 1H), 3.30 (obsc-m, 1H), 2.03 (m, 2H), 1.85 (m, 2H). ESIMS m/z: M$^+$ 578.5;

2-[5-(5-carbamimidoyl-1H-benzoimidazol-2-yl)-6,2'-dihydroxy-5'-sulfamoyl-biphenyl-3-yl]-acetamide, Compound 126, H$^1$ NMR (CD$_3$DO-d4) 3.621 (s, 2H) 7.07 (d, J=8 Hz, 1H) 7.15 (br s, 2H) 7.27 (d, J=2 Hz, 1H) 7.63 (d, J=2 Hz, 1H) 7.65 (m, 2H) 7.73 (d of d, J=2, J=8, 1H) 7.83 (d, J=8 Hz, 1H) 8.08 (d, J=2 Hz, 1H) 8.17 (s, 1H) 9.10 (s, 2H) 9.39 (s, 2H);

2-[5-(5-carbamimidoyl-1H-benzoimidazol-2-yl)-6,2'-dihydroxy-5'-sulfamoyl-biphenyl-3-yl]-N,N-dimethyl-acetamide, Compound 127, H$^1$ NMR (CD$_3$DO-d4) 9.49 (s, 1H), 9.00 (s, 1H), 8.30 (s, 1H), 8.03 (d, 1H, J=8.7 Hz), 7.95 (m, 2H, J=10.4 Hz), 7.87 (m, 2H, J=10.4 Hz), 7.51 (d, 1H, J=2 Hz), 7.12 (d, 1H, J=8.7 Hz), 3.93 (s, 2H), 3.23 (s, 3H), 3.05 (s, 3H); MS: calc 508.55. found 509.2 (M+1), 507.3 (M−1).

2-[5-(5-carbamimidoyl-1H-benzoimidazol-2-yl)-6,2'-dihydroxy-5'-sulfamoyl-biphenyl-3-yl]-N-(2-hydroxy-1-hydroxymethyl-ethyl)-acetamide, Compound 128, ¹H NMR (400 MHz, DMSO-d₆) δ 9.36 (s, 1H), 8.97 (s, 1H), 8.17 (s, 1H), 8.03 (d, 1H), 7.86 (t, 1H), 7.73 (dd, 1H), 7.67 (t, 1H), 7.64 (d, 1H), 7.30 (d, 1H), 7.16 (br-s, 1H), 7.06 (d, 1H), 3.72 (m, 4H), 3.52 (s, 2H) ESIMS m/z: M⁺ 555.2, M⁻ 553.4;

2-[5-(5-carbamimidoyl-1H-benzoimidazol-2-yl)-6,2'-dihydroxy-5'-sulfamoyl-biphenyl-3-yl]-N-(2-dimethylamino-ethyl)-acetamide (Compound 131), LCMS Calcd: 551; Obsd (MH) 551, H'-NMR: DMSO-d₆: 2.7 (d, 6H), 3.1 (q, 2H), 3.4 (q, 2H), 3.45 (s, 2H), 7.0 (d, 1H), 7.1 (s, 1H), 7.25 (s, 1H), 7.6 (d, 2H), 7.7 (d, 1H), 7.8 (d, 1H), 8.1 (s, 1H), 8.15 (s, 1H), 8.4 (t, 1H), 9.0 (s, 2H), 9.3 (s, 2H), 10.2 (s, 1H);

2-[5-(5-carbamimidoyl-1H-benzoimidazol-2-yl)-6,2'-dihydroxy-5'-sulfamoyl-biphenyl-3-yl]-N-(3-dimethylamino-propyl)-acetamide, Compound 132, LCMS Calcd: 565; Obsd (MH+) 566, H'-NMR: DMSO_d6: 1.85 (m, 2H), 2.5 (s, 6H), 2.8 (m, 2H), 3.1 (m, 2H), 3.2 (m, 2H), 4.6 (s, 2H), 7.1 (d, 1H), 7.2 (s, 1H), 7.3 (s, 1H), 7.7 (s, 1H), 7.75 (d, 1H), 7.85 (d, 1H), 8.1 (s, 1H), 8.2 (s, 1H), 8.3 (t, 1H), 9.0 (s, 2H), 9.4 (s, 2H), 10.4 (s, 1H);

2-[5-(5-carbamimidoyl-1H-benzoimidazol-2-yl)-6,2'-dihydroxy-5'-sulfamoyl-biphenyl-3-yl]-N-methyl-N-{2-[2-(2-methylamino-ethoxy)-ethoxy]-ethyl}-acetamide (Compound 134), LC-MS: Calcd. 639.25, Observed. 640.6 (M+1), 638.5 (M−1);

2-[5-(5-carbamimidoyl-1H-benzoimidazol-2-yl)-6,2'-dihydroxy-5'-sulfamoyl-biphenyl-3-yl]-N-(3S,4S,5R,6S-tetrahydroxy-tetrahydro-pyran-2R-ylmethyl)-acetamide (Compound 135), RP-HPLC (1-90S) RT=2.17 min; ¹H NMR (400 MHz, d₆-DMSO+D₂O, selected signals, as a 40:60 mixture of α:β anomers): δ 8.14 (1H, br s), 7.94 (1H, br d, J=2.0 Hz), 7.84 (1H, d, J=8.4 Hz), 7.71 (1H, m), 7.68-7.66 (2H, m), 7.28 (1H, d, J=2.0 Hz), 7.05 (1H, d, J=8.4 Hz), 4.91 (0.4H, d, J=3.6 Hz, α-anomer), 4.30 (0.6H, d, J=8.0 Hz, β-anomer; m/z (LCMS-ESI): Q⁺ 643.4 (M+H, calc. 643.2); Q⁻ 641.5 (M−H, calc. 641.2); 2-[5-(5-carbamimidoyl-1H-benzoimidazol-2-yl)-6,2'-dihydroxy-5'-sulfamoyl-biphenyl-3-yl]-N-(2,4R,5S-trihydroxy-6R-hydroxymethyl-tetrahydro-pyran-3-yl)-acetamide (Compound 136), LCMS: Calcd 642.65; Obsd (MH+)=643.4, (MH−)=641.3.

NMR (DMSO-d6) d 3.18 (m, 1H), 3.4-3.8 (m, 8H), 4.8-5.3 (br s, 7H), 7.11 (d, J=8 Hz, 1H), 7.20 (br s, 1H), 7.32 (d, J=2 Hz, 1H), 7.65 (d, J=2 Hz, 1H), 7.68 (m, 2H), 7.77 (d of d, J=2, J=8 Hz, 1H), 7.85 (d, J=8 Hz, 1H), 8.12 (d of d, J=2, J=8 Hz, 1H), 8.22 (s, 1H), 9.11, 9.42 (2s, 4H);

2-[5-(5-carbamimidoyl-1H-benzoimidazol-2-yl)-6,2'-dihydroxy-5'-sulfamoyl-biphenyl-3-yl]-N-methyl-N-(2R,3R,4R,5S,6-pentahydroxy-hexyl)-acetamide (Compound 137), RP-HPLC (1-90S) RT=2.20 min; ¹H NMR (400 MHz, d₆-DMSO+D₂O, selected signals, as 60:40 mixture of amide rotamers): δ 8.14 (1H, s), 7.88 (1H, m), 7.84 (1H, d, J=8.8 Hz), 7.70 (1H, dd, J=8.4, 1.6 Hz), 7.69-7.66 (2H, m), 7.25 (0.4H, d, J=2.0 Hz, 1st rotamer), 7.20 (0.6H, d, J=2.0 Hz, 2nd rotamer), 7.05 (1H, m), 3.68-3.40 (8H, m), 3.14 (1.2H, s, 1st rotamer), 2.88 (1.8H, s, 2nd rotamer); m/z (LCMS-ESI): Q⁺ 659.6 (M+H, calc. 659.2); Q⁺ 657.6 (M−H, calc. 657.2);

2-[5-(5-carbamimidoyl-1H-benzoimidazol-2-yl)-6,2'-dihydroxy-5'-sulfamoyl-biphenyl-3-yl]-N-(2-hydroxy-1,1-bis-hydroxymethyl-ethyl)-acetamide (Compound 138), ¹H NMR (400 MHz, DMSO-d₆) δ 9.36 (s, 1H), 8.98 (s, 1H), 8.17 (d, 1H), 8.03 (d, 1H), 7.86 (d, 1H), 7.73 (dd, 1H), 7.67 (dd, 1H), 7.50 (s, 1H), 7.30 (d, 1H), 7.16 (br-s, 1H), 7.06 (d, 1H), 4.21 (t, 1H), 3.98 (m, 6H), 3.83 (s, 2H), ESIMS m/z: M⁺ 585.4, M⁻ 583.4;

2-[5-(5-carbamimidoyl-1H-benzoimidazol-2-yl)-6,2'-dihydroxy-5'-sulfamoyl-biphenyl-3-yl]-N-methyl-acetamide (Compound 139), LCMS: Calcd 494.53; Obsd (MH+) =495.1, (MH−)=493.1, NMR (DMSO-d6) d 2.62 (s, 3H), 3.49 (s, 2H), 7.08 (d, J=8 Hz, 1H), 7.18 (br s, 2H), 7.30 (d, J=2 Hz, 1H), 7.67 (d, J=2 Hz, 1H), 7.69 (m, 1H), 7.78 (d of d, J=2, J=8 Hz, 1H), 7.83 (d, J=8 Hz, 1H), 8.04 (m, 1H), 8.10 (d, J=2 Hz, 1H), 8.21 (s, 1H), 9.08, 9.41 (2s, 4H);

2S-{2-[2-[5-(5-carbamimidoyl-1H-benzoimidazol-2-yl)-6,2'-dihydroxy-5'-sulfamoyl-biphenyl-3-yl]-acetylamino}-succinamide (Compound 140), 1H NMR (DMSO-d6): 10.23 (br s, 1H), 9.33 (s, 2H), 8.94 (s, 2H), 8.32 (d, 1H, J=8.4 Hz), 8.16 (s, 1H), 8.00 (s, 1H), 8.83 (d, 1H, J=8.4 Hz), 7.71 (d, 1H, J=8.8 Hz), 7.66 (m, 2H), 7.62 (d, 1H, J=2.4 Hz), 7.44 (s, 1H), 7.27 (d, 2H, J=2.0 Hz), 7.15 (s, 2H), 7.04 (d, 1H, J=8.4 Hz), 6.94 (s, 1H), 4.53 (dd, 1H, J=7.6, 8.4 Hz), 3.53 (br s, under water peak), 2.56 (dd, 1H, J=5.2, 15.6 Hz), 2.42 (dd, 1H, J=8.4, 15.6 Hz). LC-MS: Calcd. 594.16, Observed. 595.3 (M+1), 593.1 (M−1);

2-[5-(5-carbamimidoyl-1H-benzoimidazol-2-yl)-6,2'-dihydroxy-5'-sulfamoyl-biphenyl-3-yl]-N-{3-[2-(2-ethoxy-ethoxy)-ethoxy]-propyl}-acetamide hydrochloride (Compound 141), ¹H NMR: 9.40 (2H, br s), 9.07 (2H, br s), 8.20 (1H, br s), 8.14-8.05 (2H, m), 7.87 (1H, d, J=8 Hz), 7.76 (1H, dd, J=8 and 2 Hz), 7.70-7.65 (3H, m), 7.31 (1H, d, J=2.4 Hz), 7.09 (8.4 Hz), 3.58-3.38 (14H, m), 3.14 (2H, q, J=6.8 Hz), 1.67 (2H, quintet, J=6.4 Hz), 1.10 (3H, t, J=7.2 Hz).

3'-(5-carbamimidoyl-1H-pyrrolo[3,2-b]pyridin-2-yl)-6,2'-dihydroxy-biphenyl-3-carbox amide (Compound 239), Mass: Observed m/z. 417 (M+1) Calculated m/z 416 (M+); and 2-(2,2'-dihydroxy-5'-ureido-biphenyl-3-yl)-1H-pyrrolo[3,2-b]pyridine-5-carboxamidine, Mass: Observed m/z 402 (M+2) Calculated m.z 401 (M+).

Biological Examples

Example 1

In Vitro Factor VIIa Inhibitor Assay

Mixtures of human Factor VIIa (typically supplied at 7 nM) and test compound (present at varying concentrations) in assay medium (comprising: NaCl, 150 mM (pH 7.4); CaCl₂, 5 mM; Tween-20, 0.05%; Dade Innovin tissue factor [Dade Behring, Newark, Del., USA]; EDTA, 1.5 mM; and dimethylsulfoxide, 10%) were incubated for 30 minutes at room temperature. Next, reactions were initiated with the addition of substrate[500 μM of CH-₃SO₂-D-Cha-But-Arg-pNA (from Centerchem, Norwalk, Conn., USA)]. Hydrolysis of the chromogenic substrate was followed spectrophotometrically at 405 nm for five minutes. Initial velocity measurements calculated from the progress curves by a kinetic analysis program (Batch Ki; BioKin, Ltd., Pullman, Wash.) were used to determine apparent inhibition constants (apparent $K_i$'s).

Compounds of the invention tested by the above-described assay exhibited inhibition of Factor VIIa.

Example 2

In Vitro Factor Xa Inhibitor Assay

Mixtures of human Factor Xa (typically supplied at 3 nM) (from Haematologic Technologies, Essex Junction, VT, USA) and test compound (varying concentrations) in assay medium (comprising: Tris, 50 mM (pH 7.4); NaCl, 150 mM; CaCl₂, 5 mM; Tween-20, 0.05%; EDTA, 1 mM; and dimethylsulfoxide, 10%) were incubated for 30 minutes at room temperature. Next, reactions were initiated with the addition of substrate[500 μM of CH-$_3$CO$_2$-D-Cha-Gly-Arg-pNA (from Centerchem, Norwalk, Conn., USA]. Hydrolysis of the chromogenic substrate was followed spectrophotometrically at (405 nm) for five minutes. Apparent inhibition constants (apparent K$_i$'s) were calculated from the enzyme progress curves using standard mathematical models.

Compounds of the invention tested by the above-described assay exhibited inhibition of Factor Xa.

Example 3

Pharmacokinetic Assay

Rats with pre-implanted jugular vein catheters, which were filled with heparin/saline/PVP lock prior to shipment, were bought from Charles River. Three rats were selected for each study, weighed, and injected with test compound by tail vein injection. Any residual test compound was retained and stored at −70° C. for later analysis.

Blood samples (0.25 mL each) were collected from the indwelling catheters at specified times over 120 h. The catheters were flushed with physiological saline immediately after each collection and filled with heparinized saline after each 8, 24 and 48 h collection. In the event that a catheter failed, blood samples were collected via the retro-orbital sinus under isoflurane anesthesia at the appropriate time.

Blood samples were placed in 0.5 mL Microtainer® tubes (lithium heparin), shaken gently and stored on wet ice. The samples were centrifuged for 10 minutes at 2400 rpm in a refrigerated centrifuged. Plasma samples (0.1 mL) from each tube were transferred to 0.5 mL Unison polypropylene vials (Sun-500210) and stored below −70° C. for later analysis by LC/MS-MS.

Example 4

In Vitro Clotting Assays . . . aPTT and PT

Coagulation assays, activated partial thromboplastin time (aPTT) and prothrombin time (PT) were carried out based on the procedure described in Hougie, C. *Hematology* (Williams, W. J., Beutler, B., Erslev, A. J., and Lichtman, M. A., Eds.), pp. 1766-1770 (1990), McGraw-Hill, New York.

Briefly, the assays were performed using normal human citrated plasma and were performed at 37° C. on a coagulometer (Electra 800) in accordance with the manufacturer's instructions (Medical Laboratory Automation-Pleasantville, N.Y.). The instrument was calibrated with plasma immediately prior to collecting clotting times for samples with inhibitors. The aPTT and PT doubling concentrations were calculated by fitting inhibitor dose response curves to a modified version of the Hill equation.

Pharmaceutical Composition Examples

The following are representative pharmaceutical formulations containing a compound of Formula I.

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

Injectable Formulation

The following ingredients are mixed to form an injectable formulation.

| Ingredient | Amount |
|---|---|
| compound of this invention | 1.2 g |
| sodium acetate buffer solution, 0.4M | 2.0 mL |
| HCl (1N) or NaOH (1N) | q.s. to suitable pH |
| water (distilled, sterile) | q.s. to 20 mL |

All of the above ingredients, except water, are combined and heated to 60-70° C. with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| compound of the invention | 500 mg |
|---|---|
| Witepsol ® H-15 | balance |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

We claim:

1. A composition comprising human Factor IXa and a compound of Formula I:

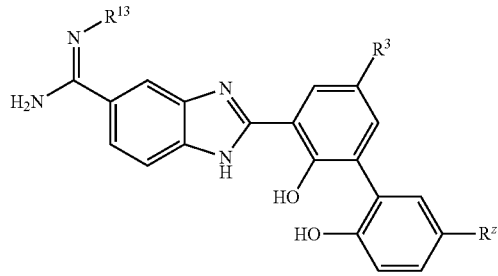

Formula I wherein:
R$^3$ is —CONR$^7$R$^8$, —CH$_2$CONR$^9$R$^{10}$ or —C(CH$_3$)$_2$CONR$^9$R$^{10}$;
R$^7$ is hydrogen or methyl;
R$^9$ is hydrogen or methyl;
R$^8$ is aminocarbonylmethyl, 1,2-diaminocarbonylethyl, 2-aminocarbonyl-1-carboxyethyl, 5-amino-5-carboxypentyl, 2-carboxyethyl, carboxymethyl, 2-carboxy-3-[2-(2-ethoxy-ethoxy)-ethoxy]-propyl, dimethylaminomethyl, 3-dimethylaminopropyl, 2-hydroxy-1,1-bis-hydroxymethyl-ethyl, 2-hydroxy-1-hydroxymethylethyl, 1,2-dicarboxyethyl, methyl, 2-[2-(2-methylaminoethoxy)ethoxy]ethyl, 2-(4-methylpiperazin-1-yl)ethyl, 2-morpholin-4-ylethyl, 2,3,4,5,6-pentahydroxy-hexyl, 2-piperazin-1-ylethyl, 2-sulfoethyl, 3,4,5,6-tetrahydroxy-tetrahydro-pyran-2-ylmethyl, 2,4,5-trihydroxy-6-hydroxymethyl-tetrahydro-pyran-3-yl, 2,4,5-trihydroxy-6-hydroxymethyl-tetrahydro-pyran-3-ylcarbamoyl-methyl, trimethylammonioethyl or 2-phosphonoethyl;
R$^{10}$ is aminocarbonylmethyl, 1,2-diaminocarbonylethyl, 2-aminocarbonyl-1-carboxyethyl, 5-amino-5-carboxypentyl, 2-carboxyethyl, carboxymethyl, 2-carboxy-3-[2-(2-ethoxy-ethoxy)-ethoxy]-propyl, dimethylaminomethyl, 3-dimethylaminopropyl, 2-hydroxy-1,1-bis-hydroxymethyl-ethyl, 2-hydroxy-1-hydroxymethylethyl, 1,2-dicarboxyethyl, methyl, 2-[2-(2-methylaminoethoxy)ethoxy]ethyl, 2-(4-methylpiperazin-1-yl)ethyl, 2-morpholin-4-ylethyl, 2,3,4,5,6-pentahydroxy-hexyl, 2-piperazin-1-ylethyl, 2-sulfoethyl, 3,4,5,6-tetrahydroxy-tetrahydro-pyran-2-ylmethyl, 2,4,5-trihydroxy-6-hydroxymethyl-tetrahydro-pyran-3-yl, 2,4,5-trihydroxy-6-hydroxymethyl-tetrahydro-pyran-3-ylcarbamoyl-methyl, trimethylammonioethyl or 2-phosphonoethyl;
R$^z$ is aminosulfonyl or ureidomethyl;
R$^{13}$ is hydrogen;
or a pharmaceutically acceptable salt thereof.

2. The composition of claim 1, wherein:
R$^3$ is —CONR$^7$R$^8$, —CH$_2$CONR$^9$R$^{10}$ or —C(CH$_3$)$_2$CONR$^9$R$^{10}$;
R$^7$ is hydrogen;
R$^9$ is hydrogen;
R$^8$ is 2,4,5-trihydroxy-6-hydroxymethyl-tetrahydro-pyran-3-yl, 2,4,5-trihydroxy-6-hydroxymethyl-tetrahydro-pyran-3-ylcarbamoyl-methyl, aminocarbonylmethyl, 2-aminocarbonyl-1-carboxyethyl, 5-amino-5-carboxypentyl, 2-carboxyethyl, carboxymethyl, or 1,2-dicarboxyethyl;
R$^{10}$ is aminocarbonylmethyl, 2-aminocarbonyl-1-carboxyethyl, 5-amino-5-carboxypentyl, 2-carboxyethyl, carboxymethyl, or 1,2-dicarboxyethyl; and
R$^z$ is aminosulfonyl.

3. A composition comprising human Factor IXa and a compound having the structure:

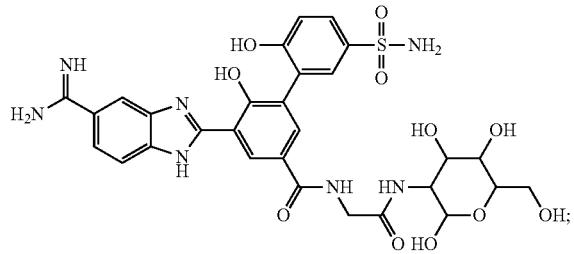 [SMILES: N=C(N)c1ccc2[nH]c(-c3cc(C(=O)NCC(=O)NC4C(O)OC(CO)C(O)C4O)cc(-c4cc(S(N)(=O)=O)ccc4O)c3O)nc2c1]

or a pharmaceutically acceptable salt thereof.

* * * * *